(12) United States Patent
Fan et al.

(10) Patent No.: US 11,337,643 B2
(45) Date of Patent: *May 24, 2022

(54) MACHINE LEARNING SYSTEMS AND TECHNIQUES FOR MULTISPECTRAL AMPUTATION SITE ANALYSIS

(71) Applicant: SPECTRAL MD, INC., Dallas, TX (US)

(72) Inventors: Wensheng Fan, Plano, TX (US); John Michael DiMaio, Dallas, TX (US); Jeffrey Thatcher, Irving, TX (US)

(73) Assignee: Spectral MD, Inc., Dallas, TX (US)

( * ) Notice: Subject to any disclaimer, the term of this patent is extended or adjusted under 35 U.S.C. 154(b) by 75 days.

This patent is subject to a terminal disclaimer.

(21) Appl. No.: 17/000,810

(22) Filed: Aug. 24, 2020

(65) Prior Publication Data

US 2021/0169400 A1   Jun. 10, 2021

Related U.S. Application Data

(63) Continuation of application No. 16/670,911, filed on Oct. 31, 2019, now Pat. No. 10,750,992, which is a
(Continued)

(51) Int. Cl.
*A61B 5/00*      (2006.01)
*A61B 5/02*      (2006.01)
*G06V 10/75*     (2022.01)

(52) U.S. Cl.
CPC ............ *A61B 5/445* (2013.01); *A61B 5/0077* (2013.01); *A61B 5/02007* (2013.01);
(Continued)

(58) Field of Classification Search
CPC ... A61B 5/445; A61B 5/0077; A61B 5/02007; A61B 5/443; A61B 5/7267;
(Continued)

(56) References Cited

U.S. PATENT DOCUMENTS 4,170,987 A    10/1979  Anselmo et al.
4,693,255 A     9/1987  Beall
(Continued)

FOREIGN PATENT DOCUMENTS

CA    2287687    5/2000
CN    1543325   11/2004
(Continued)

OTHER PUBLICATIONS

Blanpain et al., "Epidermal homeostasis: A balancing act of stem cells in the skin", Nature Reviews Molecular Cell Biology, Mar. 2009, vol. 10, pp. 207-217.
(Continued)

*Primary Examiner* — Serkan Akar
*Assistant Examiner* — Aminah Asghar
(74) *Attorney, Agent, or Firm* — Knobbe Martens Olson & Bear, LLP

(57) ABSTRACT

Certain aspects relate to apparatuses and techniques for non-invasive and non-contact optical imaging that acquires a plurality of images corresponding to both different times and different frequencies. Additionally, alternatives described herein are used with a variety of tissue classification applications including assessing the presence and severity of tissue conditions, such as necrosis and small vessel disease, at a potential or determined amputation site.

20 Claims, 30 Drawing Sheets

Related U.S. Application Data continuation of application No. 16/489,955, filed as application No. PCT/US2018/020661 on Mar. 2, 2018.

(60) Provisional application No. 62/465,956, filed on Mar. 2, 2017.

(52) U.S. Cl.
CPC ............ A61B 5/443 (2013.01); A61B 5/7267 (2013.01); G06V 10/751 (2022.01)

(58) Field of Classification Search
CPC . A61B 5/0075; A61B 5/14551; A61B 5/0064; A61B 5/026; A61B 5/0261; A61B 5/441; A61B 5/7264; G06V 10/751; G16H 50/20
See application file for complete search history.

(56) References Cited

U.S. PATENT DOCUMENTS

| | | |
|---|---|---|
| 5,074,306 A | 12/1991 | Green et al. |
| 5,701,902 A | 12/1997 | Vari et al. |
| 5,982,497 A | 11/1999 | Hopkins |
| 6,008,889 A | 12/1999 | Zeng et al. |
| 6,058,352 A | 5/2000 | Lu et al. |
| 6,081,612 A | 6/2000 | Gutkowicz-Krusin et al. |
| 6,352,517 B1 | 3/2002 | Flock et al. |
| 6,353,753 B1 | 3/2002 | Flock et al. |
| 6,381,488 B1 | 4/2002 | Dickey et al. |
| 6,411,907 B1 | 6/2002 | Lu et al. |
| 6,638,668 B2 | 10/2003 | Buchsbaum et al. |
| 6,640,132 B1 | 10/2003 | Freeman et al. |
| 6,889,075 B2 | 5/2005 | Marchitto et al. |
| 7,433,042 B1 | 10/2008 | Cavanaugh et al. |
| 7,612,822 B2 | 11/2009 | Ajito et al. |
| 7,648,808 B2 | 1/2010 | Buchsbaum et al. |
| 7,729,750 B2 | 6/2010 | Tromberg et al. |
| 7,733,389 B2 | 6/2010 | Kurosawa et al. |
| 7,835,002 B2 | 11/2010 | Muhammed et al. |
| 7,860,554 B2 | 12/2010 | Leonardi et al. |
| 8,081,311 B2 | 12/2011 | Themelis |
| 8,233,148 B2 | 7/2012 | Bodkin et al. |
| 8,488,024 B2 | 7/2013 | Yano et al. |
| 8,509,879 B2 | 8/2013 | Dukin et al. |
| 8,583,216 B2 | 11/2013 | Pershing et al. |
| 8,605,172 B2 | 12/2013 | Nikkanen et al. |
| 8,692,912 B2 | 4/2014 | Fish et al. |
| 8,704,917 B2 | 4/2014 | Rodrigues et al. |
| 8,812,083 B2 | 8/2014 | Papazoglou et al. |
| 8,838,211 B2 | 9/2014 | Melendez et al. |
| 8,892,192 B2 | 11/2014 | Cuccia et al. |
| 9,078,619 B2 | 7/2015 | Panasyuk et al. |
| 9,295,402 B1 | 3/2016 | Arbab et al. |
| 9,372,118 B1 | 6/2016 | Tablin et al. |
| 9,547,178 B2 | 1/2017 | Erdogan et al. |
| 9,648,254 B2 | 5/2017 | Darty et al. |
| 9,717,417 B2 | 8/2017 | DiMaio et al. |
| 9,766,382 B2 | 9/2017 | Darty |
| 9,962,090 B2 | 5/2018 | DiMaio et al. |
| 10,066,997 B2 | 9/2018 | Körner et al. |
| 10,740,884 B2 | 8/2020 | McCall et al. |
| 10,750,992 B2 | 8/2020 | Fan et al. |
| 10,783,632 B2 | 9/2020 | Fan et al. |
| 11,182,888 B2 | 11/2021 | McCall et al. |
| 2002/0016533 A1 | 2/2002 | Marchitto et al. |
| 2005/0025118 A1 | 2/2005 | Hao et al. |
| 2005/0033145 A1 | 2/2005 | Graham et al. |
| 2006/0155193 A1 | 7/2006 | Leonardi et al. |
| 2006/0184043 A1 | 8/2006 | Tromberg et al. |
| 2006/0241495 A1 | 10/2006 | Kurtz |
| 2007/0016079 A1 | 1/2007 | Freeman et al. |
| 2007/0024946 A1 | 2/2007 | Panasyuk et al. |
| 2007/0038042 A1 | 2/2007 | Freeman et al. |
| 2007/0179482 A1 | 8/2007 | Anderson |
| 2007/0232930 A1 | 10/2007 | Feeman et al. |
| 2007/0249913 A1 | 10/2007 | Freeman et al. |
| 2008/0194928 A1 | 8/2008 | Bandic et al. |
| 2008/0278602 A1 | 11/2008 | Otsu |
| 2009/0072142 A1 | 3/2009 | Blitzer |
| 2009/0118600 A1 | 5/2009 | Ortiz et al. |
| 2009/0118622 A1 | 5/2009 | Dukin et al. |
| 2009/0275808 A1 | 11/2009 | DiMaio et al. |
| 2009/0275841 A1 | 11/2009 | Melendez et al. |
| 2010/0042004 A1 | 2/2010 | Dhawan |
| 2010/0210931 A1 | 8/2010 | Cuccia |
| 2010/0292549 A1 | 11/2010 | Shuler |
| 2011/0117025 A1 | 5/2011 | Dacosta et al. |
| 2011/0124987 A1 | 5/2011 | Papazoglou et al. |
| 2011/0124988 A1 | 5/2011 | Cuccia |
| 2011/0205052 A1 | 8/2011 | Clawson |
| 2012/0078088 A1 | 3/2012 | Whitestone et al. |
| 2012/0141000 A1 | 6/2012 | Jeanne et al. |
| 2012/0172243 A1 | 7/2012 | Davicioni et al. |
| 2012/0190944 A1 | 7/2012 | Thaveeprungsriporn et al. |
| 2012/0195486 A1 | 8/2012 | Kirenko et al. |
| 2012/0200700 A1 | 8/2012 | Bennett et al. |
| 2012/0209095 A1 | 8/2012 | Huiku |
| 2012/0245473 A1 | 9/2012 | Mycek et al. |
| 2012/0288230 A1 | 11/2012 | Pologe et al. |
| 2012/0307056 A1 | 12/2012 | Zuzak et al. |
| 2012/0321759 A1 | 12/2012 | Marinkovich et al. |
| 2013/0027543 A1 | 1/2013 | Boeykens et al. |
| 2013/0064441 A1 | 3/2013 | Kask |
| 2013/0274612 A1 | 10/2013 | Cuccia et al. |
| 2013/0342670 A1 | 12/2013 | Kyal et al. |
| 2014/0012225 A1 | 1/2014 | Yoo et al. |
| 2014/0092288 A1 | 4/2014 | Hattery et al. |
| 2014/0128744 A1 | 5/2014 | Cuccia et al. |
| 2014/0155757 A1 | 6/2014 | Yang et al. |
| 2014/0155818 A1 | 6/2014 | Salinas et al. |
| 2014/0193050 A1 | 7/2014 | Miller |
| 2014/0213910 A1 | 7/2014 | Durkin et al. |
| 2015/0011892 A1 | 1/2015 | Sostek |
| 2015/0025342 A1 | 1/2015 | Papazoglou et al. |
| 2015/0044098 A1 | 2/2015 | Smart et al. |
| 2015/0080742 A1 | 3/2015 | Andre et al. |
| 2015/0141839 A1 | 5/2015 | Cuccia et al. |
| 2015/0190061 A1 | 7/2015 | Godavarty et al. |
| 2015/0208923 A1 | 7/2015 | Akl et al. |
| 2015/0285685 A1 | 10/2015 | Wax et al. |
| 2015/0369664 A1 | 12/2015 | Garsha et al. |
| 2015/0374276 A1 | 12/2015 | Farkas et al. |
| 2015/0374309 A1 | 12/2015 | Farkas et al. |
| 2016/0100790 A1 | 4/2016 | Cantu et al. |
| 2016/0321414 A1 | 11/2016 | Salganicoff et al. |
| 2016/0345888 A1 | 12/2016 | Wu et al. |
| 2017/0079530 A1 | 3/2017 | DiMaio et al. |
| 2017/0084024 A1 | 3/2017 | Gurevich |
| 2017/0135646 A1 | 5/2017 | Chin |
| 2017/0150903 A1 | 6/2017 | Barnes et al. |
| 2017/0262984 A1 | 9/2017 | Barnes et al. |
| 2017/0299435 A1 | 10/2017 | Rhoads et al. |
| 2017/0319073 A1 | 11/2017 | DiMaio et al. |
| 2017/0354358 A1 | 12/2017 | Rajab |
| 2017/0367580 A1 | 12/2017 | DiMaio et al. |
| 2018/0028079 A1 | 2/2018 | Gurevich et al. |
| 2018/0061046 A1 | 3/2018 | Bozorgtabar et al. |
| 2018/0184015 A1 | 6/2018 | Richarte et al. |
| 2018/0226154 A1 | 8/2018 | Gurcan et al. |
| 2018/0245978 A1 | 8/2018 | Wang et al. |
| 2018/0247153 A1 | 8/2018 | Ganapati et al. |
| 2018/0310828 A1 | 11/2018 | DiMaio et al. |
| 2019/0082998 A1 | 3/2019 | Nowroozi et al. |
| 2019/0277753 A1 | 9/2019 | Waxman et al. |
| 2019/0290117 A1 | 9/2019 | Wang et al. |
| 2020/0138360 A1 | 5/2020 | Fan et al. |
| 2020/0193580 A1 | 6/2020 | McCall et al. |
| 2020/0193597 A1 | 6/2020 | Fan et al. |

(56) References Cited

U.S. PATENT DOCUMENTS

| | | | |
|---|---|---|---|
| 2021/0082094 | A1 | 3/2021 | McCall et al. |
| 2021/0201479 | A1 | 7/2021 | Fan et al. |

FOREIGN PATENT DOCUMENTS

| | | |
|---|---|---|
| CN | 1745294 | 3/2006 |
| CN | 1784185 | 6/2006 |
| CN | 101394782 | 3/2009 |
| CN | 101627902 | 1/2010 |
| CN | 101784227 | 7/2010 |
| CN | 102099671 | 6/2011 |
| CN | 102641126 | 8/2012 |
| CN | 103228205 | 7/2013 |
| CN | 103815875 | 6/2015 |
| CN | 105143448 | 12/2015 |
| CN | 103327894 | 5/2016 |
| CN | 105636512 | 6/2016 |
| EP | 2944930 | 11/2015 |
| JP | H05-505117 | 8/1993 |
| JP | H10-505768 | 6/1998 |
| JP | 2000-139846 | 5/2000 |
| JP | 2001-503645 | 3/2001 |
| JP | 2008-525158 | 7/2008 |
| JP | 2010-043979 | 2/2010 |
| JP | 2010-503475 | 2/2010 |
| TW | 512058 | 12/2002 |
| WO | WO 2004/005895 | 1/2004 |
| WO | WO 2014/041543 | 3/2014 |
| WO | WO 2014/125250 | 8/2014 |
| WO | WO 2015/116823 | 8/2015 |
| WO | WO 2016/069788 | 5/2016 |
| WO | WO 2017/053609 | 3/2017 |
| WO | WO 2017/074505 | 5/2017 |
| WO | WO 2018/160963 | 9/2018 |
| WO | WO 2018/217162 | 11/2018 |
| WO | WO 2020/123722 | 6/2020 |
| WO | WO 2020/123724 | 6/2020 |
| WO | WO 2020/123724 A4 | 6/2020 |
| WO | WO 2021/173763 | 9/2021 |
| WO | WO 2022/015597 | 1/2022 |

OTHER PUBLICATIONS

Devagn et al., "Modalities for the Assessment of Burn Wound Depth", Journal of Burns and Wounds, Feb. 2006, vol. 5, pp. 7-15.
Garcin et al., "Hair Follicle Bulge Stem Cells Appear Dispensable for the Acute Phase of Wound Re-epithelialization", Stem Cells, Jan. 2016, vol. 34, pp. 1377-1385.
Gurtner et al., "Wound repair and regeneration", Nature, May 2008, vol. 453, pp. 314-321.
Heimbach et al., "Burn depth: A review", World Journal of Surgery, Jan.-Feb. 1992, vol. 16, pp. 10-15.
Huot et al., "Time-resolved multispectral imaging of combustion reaction", Proc. SPIE 9485, Thermosense: Thermal Infrared Applications XXXVII, 94851C, May 2015.
Ito et al., "Stem cells in the hair follicle bulge contribute to wound repair but not to homeostasis of the epidermis", Nature Medicine, Dec. 2005, vol. 11, pp. 1351-1354.
Meyerholz et al., "Morphological Parameters for Assessment of Burn Severity in an Acute Burn Injury Rat Model", International Journal of Experimental Pathology, 2009, vol. 90, pp. 26-33.
Monstrey et al., "Assessment of Burn Depth and Burn Wound Healing Potential", Burns, 2008, vol. 34, pp. 761-769.
Papp et al., "The progression of burn depth in experimental burns: A histological and methodological study", Burns, 2004, vol. 30, pp. 684-690.
Rittie, L., "Cellular mechanisms of skin repair in humans and other mammals", Journal of Cell Communication and Signaling, 2016, vol. 10, pp. 103-120.
Rowan et al., "Burn wound healing and treatment: review and advancements", Critical Care, 2015, vol. 19, in 12 pages.
Sheng et al., "BurnCalc assessment study of computer-aided individual three-dimensional burn area calculation", Journal of Translational Medicine, Sep. 2014, vol. 12, p. 242, in 12 pages.
Singer et al., "Standardized Burn Model Using a Multi para metric Histologic Analysis of Burn Depth", Academic Emergency Medicine, Jan. 2000, vol. 7, pp. 1-6.
Takeo et al., "Wound Healing and Skin Regeneration", Cold Spring Harbor Perspectives Medicine, 2015, vol. 5, in 13 pages.
Tiwari, V.K., "Burn wound: How it differs from other wounds?" Indian Journal of Plastic Surgery, May-Aug. 2012, vol. 45, pp. 364-373.
Xie et al., "Skin appendage-derived stem cells: cell biology and potential for wound repair", Burns and Trauma, 2016, vol. 4(38), in 6 pages.
2011 National Burn Repository: Report of Data from 2001-2010. American Burn Association (2011) pp. 134.
Afromowitz et al., "Clinical Evaluation of Burn Injuries Using an Optical Reflectance Technique," IEEE Transactions on Biomedical Engineering, 1987; 34(2):114-27.
Afromowitz et al., "Multispectral imaging of burn wounds: a new clinical instrument for evaluating burn depth". IEEE transactions on bio-medical engineering, 1988; 35(10):842-850.
Aldrich, John, "R. A. Fisher and the Making of Maximum likelihood 1912-1922", Statistical Science, 1997; 12(3):162-176.
Alian et al., "Photoplethysmography," Best Pract. Res. Clin. Anaesthesiol., 2014; 28(4):395-406; ePub Sep. 9, 2014.
Allen, John, "Photoplethysmography and its application in clinical physiological measurement.," Physiol. Meas., 2007; 28:R1-R39.
Anselmo et al., "Multispectral Photographic Analysis—A New Quantitative Tool to Assist in the Early Diagnosis of Thermal Burn Depth." Annals Of Biomed Engin. 1977; 5:179-193.
Antonutto et al., "Noninvasive assessment of cardiac output from arterial pressure profiles during exercise," Eur J Appl Physiol. 1995; 72:18-24.
Arsenault et al., "The Use of Transcutaneous Oximetry to Predict Healing Complications of Lower Limb Amputations: A Systematic Review and Meta-Analysis," Eur J Vasc Endovasc Surg. 2012; 43:329-336.
Badrinarayanan et al., "SegNet: A Deep Convolutional Encoder-Decoder Architecture for Robust Semantic Pixel-Wise Labelling", Computer Science, CVPR 2015, https://arxiv.org/abs/1505.07293, May 2015.
Bajwa et al., "Assessment of Tissue Perfusion in the Lower Limb: Current Methods and Techniques Under Development," Circ Cardiovasc Imag. Sep. 2014; 7:836-843.
Bak et al., "Hemodynamic Changes During Resuscitation After Burns Using The Parkland Formula". J Trauma-Injury Infect Crit Care, 2009; 66(2):329-336.
Benitez et al., "Contemporary assessment of foot perfusion in patients with critical limb ischemia," Semin Vasc Surg. Mar. 2014; 27:3-15.
Branski et al., "A porcine model of full-thickness burn, excision, and skin autografting," Burns 2008; 34(8):1119-1127.
Burgess et al., "Segmental Transcutaneous Measurements of PO2 in Patients Requiring Below-The-Knee Amputation for Peripheral Vascular Insufficiency," J Bone Jt Surg Am 1982; 64:378-82.
Cancio et al., "Burn Support for Operation Iraqi Freedom and related operations, 2003 to 2004", J Burn Care Rehabil. (2005) 26(2): 151-161.
CDC, Diabetes Public Health Resource, "Number (in Thousands) of Hospital Discharges for Non-Traumatic Lower Extremity Amputation with Diabetes as a Listed Diagnosis, United States, 1988-2006," Centers for Disease Control and Prevention, Oct. 20, 2016, Available at: http://www.cdc.gov/diabetes/statistics/lea/fig1.htm; 3 pages.
Cheong et al., "A Review of the Optical Properties of Biological Tissues", IEEE J Quantum Electronics; 1990; 26(12): 2166-2185.
Cortes et al., "Support-Vectors Networks," Machine Learning 1995; 20:273-297.
Cousineau et al., "Outliers detection and treatment: a review," Inter J Psycholog Res. 2010; 3(1):58-67.
Cover et al., "Nearest Neighbor Pattern Classification", IEEE Transactions on Information Theory; 1967; 13(1):21-27.

(56) References Cited

OTHER PUBLICATIONS

Cross et al., "Near infrared point and imaging spectroscopy for burn depth assessment", Int'l Congress Series (2005) 1281: 137-142.
Cross et al., "Clinical Utilization of Near-infrared Spectroscopy Devices for burn depth assessment", Wound Rep Reg. (2007) 15: 332-340.
Cuccia et al., "Quantitation and mapping of tissue optical properties using modulated imaging," J Biomed Opt., 2009; 14(2): 1-31.
Desai et al., "Early Burn Wound Excision Significantly Reduces Blood Loss," Ann. Surg. 1990; 211(6):753-762.
Dillingham et al., "Reamputation, Mortality, and Health Care Costs Among Persons with Dysvascular Lower-Limb Amputations," Arch Phys Med Rehabil. 2005; 86:480-486.
Duda et al., *Pattern Classification*, Second Edition, John Wiley & Sons, Nov. 2000.
Eisenbeiss et al., "Reflection-optical multispectral imaging method for objective determination of burn depth," Burns. 1999; 25:697-704.
Elmasry et al., "Chapter 1: Principles of Hyperspectral Imaging Technology", *Hyperspectrai Imaging for Food Quality Analysis and Control*, Dec. 2010, pp. 3-43.
Eneroth, M., "Factors affecting wound healing after major amputation for vascular disease: a review," Prosth Ortho Internat. 1999; 23:195-208.
Engrav et al., "Early Excision and Grafting vs. Nonoperative Treatment of Burns of Indeterminant Depth: A Randomized Prospective Study," J of Trauma, 1983; 23(11):1001-1004.
Fischer et al., "Multispectral and Hyperspectral imaging technologies in conservation: current research and potential applications," Stud Conserv. 2006; 7: 3-16.
Franklin et al., "Cost of lower-limb amputation in US veterans with diabetes using health services data in fiscal years 2004 and 2010," J Rehabil Res Dev (JRRD) 2014; 51(8):1325-1330.
Graham et al., "Wound Healing of Cutaneous Sulfur Mustard Injuries: Strategies for the Development of Improved Therapies," J Burns and Wounds. 2005; 4:1-45.
Grubbs, Frank E., "Procedures for detecting outlying observations in samples", Ballistic Research Laboratories, Aberdeen Proving Ground, 1974; BRL Report No. 1713; 53 pages.
Grubbs, Frank E., "Procedures for Detecting Outlying Observations in Samples", Technometrics, vol. 11(1), Feb. 1969, pp. 1-21.
Guo et al., "Factors Affecting Wound Healing," J Dent Res. 2010; 89(3):219-229.
Gurfinkel et al., "Development of a Novel Animal Burn Model Using Radiant Heat in Rats and Swine," Acad Emerg Med. 2010; 17(5):514-520.
Gurfinkel et al., "Histological assessment of tangentially excised burn eschars," Can J Plast Surg. 2010; 18(3):e33-e36.
Guyon et al., "An Introduction to Variables and Feature Selection", J Machine Learn Res. 2003; 3:1157-1182.
HCUP Nationwide Inpatient Sample (NIS)—2009, Healthcare Cost and Utilization Project—HCUP, A Federal-State-Industry Partnership in Health Data Issued May 2011, Updated Nov. 2015, 89 pages, Retrievable at http://www.hcup-us.ahrq.gov; 89 pages.
Haberal et al., "Fluid management in major burn injuries", Indian J. Plast. Surg., Sep. 2010, vol. 43(Suppl), S29-S36.
Heimbach et al., *Surgical management of the burn wound*, Cover and Table of Contents, New York: Raven Press, 1984; TOC only.
Heimbach, David M., "Early Burn Excision and Grafting," Surgical Clinics of North America [Burns], 1987; 67(1):93-107.
Heredia-Juesas et al., "Non-Invasive Optical Imaging Techniques for Burn-Injured Tissue Detection for Debridement Surgery," Conf Proc IEEE/EMBS, Aug. 2016; 2893-2896.
Hu et al., "Development of Effective Photoplethysmographic Measurement Techniques: From Contact to Non-Contact and from Point to Imaging." 31st Annual International Conference of the IEEE/EMBS. 2009; 6550-6553.
HyperMed Imaging Inc., FDA-DHHS Reply to 510(k), "Hyperview Hyperspectral Tissue Oxygenation Measurement System" dated Dec. 16, 2016 with enclosures; in 15 pages.
HyperMed Medical Spectral Imaging, Product Overview "HyperView", 2017 in 4 pages.
IMEC, "Hyperspectral Imaging", downloaded from https://www.imec-int.com/en/hyperspectral-imaging on Jul. 24, 2018 in 10 pages.
Imms et al., "A high performance biometric signal and image processing method to reveal blood perfusion towards 3D oxygen saturation mapping", Progress Biomed Optics & Imaging [SPIE] (2014) 8947:89470 in 11 pages.
Israel et al., "Variations in Burn Excision and Grafting: A Survey of the American Burn Association", J Burn Care Res. (2017) 38(1): 125-132.
Ioffe et al., "Batch Normalization: Acceleration Deep Network Training by Reducing Internal Covariate Shift", 2015, arXiv:1502.03167v3, https://arxiv.org/abs/1502.03167.
Jackson D. "The diagnosis of the depth of burning." Br J Surg. 1953; 40:588-596.
Jacques et al., "Absorption spectra for biological tissues," ECE532 Biomedical Optics, 1998, Available from: http://omlc.org/education/ece532/class3/muaspectra.html; 1 page.
Jacques, Steven L., "Optical properties of biological tissues: A review", Phys Med. Biol., 2013, 58 (12), R37-61 and Corrigendum 2013 58:5007-5008.
Jaskille et al., "Critical Review of burn depth assessment techniques: Part II. Review of Laser Doppler Technology", J Burn Care Res. (2010) 31(1): 151-157.
Jolivot et al., "Skin Parameter Map Retrieval from a Dedicated Multispectral Imaging System Applied to Dermatology/Cosmetology", International Journal of Biomedical Imaging, Sep. 2013; vol. 3:978289, in 16 pages.
Jones et al., "Snapshot Spectral Imaging Technologies for On-Site Inspection", Presentation given at CTBTO Science and Technology 2015 (SnT2015) Jun. 26, 2015; Vienna, Austria; in 20 pages.
Kaiser et al., "Noninvasive assessment of burn wound severity using optical technology: A review of current and future modalities." Burns. 2011; 37(3): 377-386.
Kauvar et al., "Comparison of Combat and Non-Combat Burns from Ongoing U.S. Military Operations", J Surg Res. (2006) 132(1): 195-200.
Kearns et al., "Disaster planning: The past, present, and future concepts and principles of managing a surge of burn injured patients for those involved in hospital facility planning and preparedness," J Burn Care Res. Jan./Feb. 2014; 35(1):e33-e42.
Kendall et al., "Bayesian SegNet: Model Uncertainty in Deep Convolutional Encoder-Decoder Architectures for Scene Understanding", Oct. 2016, https://arxiv.org/abs/1511.02680.
King, Paul, Book Reviews; "*Design of Pulse Oximeters*," IEEE Eng. Med. Biol. Mag., 1998; p. 117.
King et al., "Surgical wound debridement sequentially characterized in a porcine burn model with multispectral imaging," Burns, 2015; 41:1478-1487.
Kono et al., "Identifying the incidence of and risk factors for reamputation among patients who underwent foot amputation," Ann Vase Surg 2012; 26:1120-1126.
Lee et al., "Operative wound management," Chapter 13, ©2012 Elsevier Ltd, Inc, BV, DOI: 10.1016/B978-1-4377-2786-9I00013-8, pp. 157-172e2.
Li et al., "Review of spectral imaging technology in biomedical engineering: achievements and challenges," J Biomed Optics. 2013; 18(10):100901; 29 pages.
Li et al., "Burn injury diagnostic imaging device's accuracy improved by outlier detection and removal," Proc. Of SPIE, vol. 9472, 2015 SPIE, pp. 947206-1 to 947206-11.
Li et al., "Outlier detection and removal improves accuracy of machine learning approach to multispectral burn diagnostic imaging," J. Bio. Optics. Dec. 2015; 20(12):121305-1 to 121305-9.
Lieberman, J.I. et al., National Preparedness: Countermeasures for Thermal Burns. United States Government Accountability Office. GAO-12-304R, Feb. 22, 2012.
Liu et al., "Toward integrating feature selection algorithms for classification and clustering." IEEE Transactions on Knowledge and Data Engineering. 2005. 17(4): 491-502; 35 pages.
Lu et al., "Medical hyperspectral imaging: A review," J Biomed Optics Jan. 2014; 19(1):0101901, 24 pages.

(56) References Cited

OTHER PUBLICATIONS

Macri et al., "Immediate burn excision fails to reduce injury progression," J Burn Care Res. 2013; 34(3):153-160.
Marimont et al., "Nearest Neighbor searches and the curse of Dimensionality," J Inst Math Applies 1979; 24 (1): 59-70.
Mertens et al., "Outpatient Burn Management," Nursing Clinics of North America, Burn Mgmt. 1997; 32(2):343-364.
Middelkoop et al., "Porcine wound models for skin substitution and burn treatment," Biomaterials. 2004; 25:1559-1567.
Mo et al., "The importance of illumination in a non-contact photoplethysmography imaging system for burn wound assessment", Proc. SPIE 9303 Photonic Therapeutics and Diagnostics XI, 93030M, Feb. 2015; 10 pages.
Mohler, Emile R., "Screening for Peripheral Artery Disease", Circulation, Aug. 2012, vol. 126:e111-e112, in 2 pages.
Mook et al., "Instruments and techniques: Spectrophotometric determination of oxygen saturation of blood independent of the presence of indocyanine green," Cardiovascular Research, 1979; 13:233-237.
MOOR Instruments, "Early and Accurate Burn Assessment with Laser Doppler Imaging", Product Brochure; Dec. 2014; 16 pages.
Moza et al., "Deep-Tissue Dynamic Monitoring of Decubitus Ulcers: Wound Care and Assessment," IEEE Eng Med Biol Mag. 2010; 29(2):71-77.
National Limb Loss Information Center, "Fact Sheet: Amputation Statistics by Cause: Limb Loss in the United States," National Limb Loss Information Center, Fact Sheet. Revised 2008, 3 pages.
Nehler et al., "Functional outcome in a contemporary series of major lower extremity amputations," J Vasc Surg. 2003; 38:7-14.
Nguyen et al., "Spatial frequency domain imaging of burn wounds in a preclinical model of graded burn severity." J Biomed Optics. 2013; 18(6): 066010; 8 pages.
Nilsson, Lena M. "Respiration Signals from Photoplethysmography.," Anesth Analg. 2013; 117(4):859-65.
Norgren et al., Inter-Society Consensus for the Management of Peripheral Arterial Disease (Tasc II), J Vasc Surg. 2007; 45(Supp 1):S5A-S67A.
Nouri et al., "Colour and multispectral imaging for wound healing evaluation in the context of a comparative preclinical study", Proc Opt Diagnostics of Living Cells II, (2013) 8669:866923 in 11 pages.
Obermeyer et al., "Predicting the Future—Big Data, Machine Learning, and Clinical Medicine", N Engl J Med. (Sep. 2016) 375(13): 1216-1219.
Optics.org—The business of photonics, IMEC Launches TDI, multispectral and hyperspectral sensors; News-Release of Feb. 8, 2017; SPIE Europe in 4 pages.
Orgill, D., "Excision and skin grafting of thermal burns," New Eng J Med. 2011; 360:893-901.
Ortiz-Pujols et al., "Burn care: Are there sufficient providers and facilities?" Chapel Hill, North Carolina. American College of Surgeons Health Policy Research Institute, Nov. 2011; 9:4 pages.
Pape et al., "An audit of the use of laser Doppler imaging (LDI) in the assessment of burns of intermediate depth," Burns 2001; 27:233-239.
Peng et al., "Feature Selection Based on Mutual Information: Criteria of Max-Dependency, Max-Relevance, and Min-Redundancy," IEEE Trans. on Pattern Analysis and Machine Intelligence, 2005; 27(8):1226-1238.
Perkins et al., "GENIE: A Hybrid Genetic Algorithm for Feature Classification in Multi-Spectral Images", in *Applications and science of neural networks, fuzzy systems, and evolutionary computation III*; Inter'l Society of Optics and Photonics (2000) 4120:52-63.
Petricoin et al., "SELDI-TOF-based serum proteomic pattern diagnostics for early detection of cancer", Curr Opin Biotechnol. (2004) 15(1): 24-30.
Regensteiner et al., "The impact of peripheral arterial disease on health-related quality of life in the Peripheral Arterial Disease Awareness, Risk, and Treatment: New Resources for Survival (PARTNERS) Program", Vascular Medicine, Feb. 2008, vol. 13:15-24.
Reisner et al., "Utility of the Photoplethysmogram in Circulatory Monitoring", Anesthesiol. 2008; 108:950-958.
Resch et al., "Estimation of burn depth at burn centers in the United States: a survey." J Burn Care Res. Nov./Dec. 2014; 35: 491-497.
RESURGE International, "Burns: The Neglected but Solvable Health Crisis" from Reconstructive Surgery for the World's Poor since 1969; accessed <http://www.resurge.org/transforming_lives/story_burns.cfm> Accessed Feb. 9, 2015; 3 pages.
Rogers et al., "The right to bear legs—An amendment to healthcare: how preventing amputations can save billions for the US health-care system," J Am Podiatr Med Assoc 2008; 98:166-168.
Rousseeuw, Peter J. "Least Median of Squares Regression". J Am Stat Assoc. 1984; 79(388):871-880.
Severinghaus et al., "History of Blood Gas Analysis. VII. Pulse Oximetry." J Clin Monitor. 1987; 3(2):135-138.
Siew, Ronian [Ed.], Multiple-Field Multispectral Imaging Using Wide-Angle Lenses, Inopticalsolutions Notebook Series (2018); Chapter 1, pp. 1-12.
Singer et al., "A porcine burn model," Meth Mol Med. 2003; 78:107-119.
Sokolova et al., "A systematic analysis of performance measures for classification tasks." Info Proc Manag. 2009; 45: 427-437.
Sowa et al., "Near infrared spectroscopic assessment of hemodynamic changes in the early post-burn period", Burns (2001) 27: 241-249.
Sowa et al., "Classification of burn injuries using near-infrared spectroscopy", J Biomed Optics. (Sep. 2006) 11(5): 6 pages.
Spectral MD, Inc., "DeepView Digital Video Physiological Portable Imaging System", FDA Traditional 510(k) Application as filed Dec. 28, 2012; 528 pages.
Spigulis et al., "A Device for Multimodal Imaging of Skin", Multimodal Biomedical Imaging VIII, Proc. SPIE, vol. 8574, p. 857403, Feb. 2013, in 7 pages.
Squiers et al., "Multispectral imaging burn wound tissue classification system: a comparison of test accuracies between several common machine learning algorithms," Proc. Of SPIE, 2016; 9785:97853L-1 to 97853L-10.
Steinberg et al., "Sample size for positive and negative predictive value in diagnostic research using case-control designs", Biostatistics, vol. 10, No. 1, pp. 94-105, 2009.
Thatcher et al., "Dynamic tissue phantoms and their use in assessment of a noninvasive optical plethysmography imaging device," SPIE Sensing Technology + Applications, May 2014; 910718, 18 pages.
Thatcher et al., "Imaging Techniques for Clinical Burn Assessment with a Focus on Multispectral Imaging," Advan Wound Care, Mar. 2016; 5(8):360-378.
Thatcher et al., "Multispectral and Photophlethysmography Optical Imaging Techniques Identify Important Tissue Characteristics in an Animal Model of Tangential Burn Excision," J Burn Care & Res., Jan./Feb. 2016, 37(1):38-52.
Themelis et al., "Multispectral Imaging Using Multiple-bandpass filters", Opt Lett., May 2008; 33(9):1023-1025.
Li et al., "Simultaneous measurement of deep tissue blood flow and oxygenation using noncontact diffuse correlation spectroscopy flow-oximeter", Scientific Reports, Feb. 2013, 3:1358, pp. 1-10.
Tuchin, Valery V., "Light-Tissue Interactions", Biomedical Photonics Handbook, CRC Press, Boca Raton, Florida 2003; Chapter 3; pp. 123-167.
Usman et al., "Second Derivative of Photoplethysmogram in Estimating Vascular Aging Among Diabetic Patients," in Internet Conf for Technical Postgraduates 2009, TECHPOS 2009, 3 pages.
Vemulapalli et al., "Peripheral arterial testing before lower extremity amputation among Medicare beneficiaries, 2000 to 2010," Circ Cardiovasc Qual Outcomes, Jan. 2014, 7:142-150.
Vogel et al., "Using Non-Invasive Multi-Spectral Imaging to Quantitatively Assess Tissue Vasculature", J Biomed Optics (2007) 12(5): 051604 in 32 pages.
Waters et al., "Energy cost of walking of amputees: the influence of level of amputation," J Bone Joint Surg. 1975; 58(1):42-46.
Watts et al., "Burn depth and its histological measurement," Burns 27 (2001) 154-160.
Webb, Steve [Ed.], The physics of medical imaging, © 1988, IOP Publishing Ltd., TOC only.

(56) References Cited

OTHER PUBLICATIONS

Webster, J.G. [Ed.], Design of Pulse Oximeters, Medical Science Series, © IOP Publishing Ltd. 1997; TOC only.

Worsley et al., "Back to basics: biophysical methods in tissue viability research," (Draft); J Wound Care, 2013; 22(8):434-439.

Wütschert et al., "Determination of Amputation Level in Ischemic Limbs—Reappraisal of the measurement of $TcPo_2$", Diabetes Care, 1997; 20(8):1315-1318.

Ziegler-Graham et al., "Estimating the Prevalence of Limb Loss in the United States: 2005 to 2050," Arch Phys Med Rehabil. 2008; 89:422-429.

Zonios et al., "Skin melanin, hemoglobin, and light scattering properties can be quantitatively assessed in vivo using diffuse reflectance spectroscopy", J Invest Dermatol. (2001) 117(6): 1452-1457.

Chinese Office Action in CN Application No. 201680076887.X, dated Jun. 3, 2020.

International Search Report and Written Opinion dated Jun. 20, 2018 for PCT/US2018/020661.

International Search Report and Written Opinion dated Feb. 20, 2020 for PCT/US2019/065818.

- Viable     - Small Vessel Disease     - Necrosis

MACHINE LEARNING SYSTEMS AND TECHNIQUES FOR MULTISPECTRAL AMPUTATION SITE ANALYSIS

CROSS-REFERENCE TO RELATED APPLICATIONS

The present application is a continuation of U.S. patent application Ser. No. 16/670,911, filed on Oct. 31, 2019, entitled "MACHINE LEARNING SYSTEMS AND TECHNIQUES FOR MULTISPECTRAL AMPUTATION SITE ANALYSIS," which is a continuation of U.S. patent application Ser. No. 16/489,955, filed on Aug. 29, 2019, entitled "MACHINE LEARNING SYSTEMS AND TECHNIQUES FOR MULTISPECTRAL AMPUTATION SITE ANALYSIS," which is the U.S. National Phase of PCT/US2018/020661, filed Mar. 2, 2018, entitled "MACHINE LEARNING SYSTEMS AND TECHNIQUES FOR MULTISPECTRAL AMPUTATION SITE ANALYSIS," which claims the benefit under 35 U.S.C. § 119(e) of U.S. Provisional Patent Application No. 62/465,956, filed on Mar. 2, 2017, entitled "SYSTEMS AND MACHINE LEARNING TECHNIQUES FOR AMPUTATION SITE ANALYSIS," the contents of which are hereby incorporated by reference herein in their entirety.

STATEMENT REGARDING FEDERALLY SPONSORED R&D

Some of the work described in this disclosure was made with United States Government support under Contract No. HHSO100201300022C, awarded by the Biomedical Advanced Research and Development Authority, within the Office of the Assistant Secretary for Preparedness and Response in the U.S. Department of Health and Human Services, and under Grant No. 1R43HL142428-01A1, awarded by the National Institutes of Health, within the U.S. Department of Health and Human Services. The United States Government may have certain rights in this invention.

TECHNICAL FIELD

The systems and methods disclosed herein are directed to non-invasive clinical imaging, and, more particularly, to noninvasive imaging of subdermal blood flow, diffuse reflectance spectroscopy, and computer-aided diagnosis.

BACKGROUND

Optical imaging is an emerging technology with potential for improving disease prevention, diagnosis, and treatment at the scene of an emergency, in the medical office, at the bedside, or in the operating room. Optical imaging technologies can noninvasively differentiate among tissues, and between native tissues and tissue labeled with either endogenous or exogenous contrast media, measuring their different photon absorption or scattering profiles at different wavelengths. Such photon absorption and scattering differences offers potential for providing specific tissue contrasts, and enables studying functional and molecular level activities that are the basis for health and disease.

SUMMARY

Aspects of the invention described herein relate to devices and methods that can be used to classify tissue regions at or near an amputation site using non-contact, non-invasive, and non-radiation optical imaging. Such devices and methods may, for example, identify tissue regions corresponding to different tissue health classifications relating to small vessel disease and can output a mapping of the identified regions for use by a clinician in determining a level or tissue position for amputation. Such devices and methods may, in some alternatives, identify a recommended amputation level or region of predicted optimal amputation sites and output the recommendation, for example with the tissue classification mapping. There has been a long felt need for non-invasive imaging techniques that can provide physicians with information for quantitatively selecting the appropriate level of amputation.

Approximately 185,000 lower extremity amputations occur every year in the US, and over 2 million American adults are amputees. The most significant risk factor for amputation is severe peripheral artery disease (PAD), called critical limb ischemia (CLI), with or without diabetes mellitus (DM), which accounts for well over half of all amputations, termed dysvascular amputations. Patients with DM have a 10-fold increased risk for lower extremity amputation over the general population, with over 60,000 amputations occurring annually for diabetic lower-extremity ulcers. Approximately 30 people per 100,000 individuals per year require amputation secondary to dysvascular disease, and due to the aging population of the US, this incidence is expected to increase by 50% over the next decade.

The costs, fiscal and otherwise, of limb amputation on the US healthcare system annually are immense. In one study of the Veterans Affairs (VA) system alone, the cost burden associated with diabetes-related limb loss was over 200 million (60,647/patient) in a single year (FY2010). The hospital-associated costs for all lower extremity limb amputation in the US cost totaled S8.3 billion in FY2009, with the lifetime cost of a major amputation, including rehabilitation and prosthetics costs, approximately $500,000/patient. In addition to the heavy fiscal burden of limb amputations, patients experience significant morbidities and reduction in quality of life as a result of their amputations. Most importantly, the functional status of these patients is challenged, with only 25% of major lower extremity CLI amputees able to ambulate with a prosthetic outside of their home. With progressively proximal levels of amputation, likelihood of successful rehabilitation to ambulatory status decreases due to the increased energy cost associated with increasing tissue loss.

Despite the obvious preference to salvage as much limb tissue as possible during amputation, surgeons must balance against the likelihood of primary wound healing at a given level of amputation (LOA), which decreases with more distal amputations. Selection of appropriate LOA is determined primarily by clinical judgment of the surgeon (using patient history and physical exam, including color, temperature, peripheral pulses, and wound bleeding during procedure with knowledge of clinical factors such as diabetes, smoking, nutrition, etc.), possibly in conjunction with a variety of non-invasive tests designed to quantitate tissue blood flow and/or oxygenation (ankle-brachial index [ABI], transcutaneous oxygen measurement [TCOM], or skin perfusion pressure [SPP]). However, one study demonstrated that 30% of patients with normal ABIs required re-amputation after primary forefoot amputation. This suggests that assessing macrovascular flow alone is not sufficient to predict amputation success. In the same study, nearly 50% of patients who received concurrent revascularization required reamputation as well, despite the extra effort to revascularize the distal extremity. This suggests that assessing macrovascular flow alone is not sufficient to predict amputation success. Therefore, several tests (i.e., transcutaneous oxygen measurement [TCOM]) have been developed to evaluate local tissue microcirculation and have been used clinically in an attempt to guide selection of LOA. Although TCOM initially showed promise in identifying likelihood of primary wound healing after amputation, controversy still remains regarding its utility because no sufficiently large, powered studies have been completed to define TCOM's role in clinical practice. Moreover, TCOM measurements are affected by physiologic conditions such as temperature, and TCOM electrodes are only able to analyze a small area of skin. Thus, TCOM has not been adopted into routine clinical practice even though this technology been available for decades. These modalities have had limited success as the sensitivity of perfusion assessment has never been demonstrated to supersede clinical judgment alone.

Given the challenging balance between maximizing tissue preservation and minimizing risk for non-healing primary wounds as well as a primary reliance on clinical judgment to determine the appropriate LOA, reported rates of re-amputation are in no way optimal. Re-amputation rates vary depending on initial level of amputation, from approximately 10% of above-the-knee (AKA) amputations to 35% of amputations at the foot reamputation to a more proximal level. Limited data capturing the direct costs of re-amputation are currently available, but clearly a significant portion of the billions of dollars spent annually on care associated with CLI amputation is accounted for by costs associated with reamputation, hospital readmission, and essentially ineffective wound care efforts between the index procedure and reamputation. Delayed and failed primary healing expose patients to increased risks, including infection, for morbidity and mortality. Moreover, delayed and failed primary wound healing after the index amputation procedure severely impacts patient quality of life. Patients requiring amputation revision are delayed to physical rehabilitation and in acquiring prosthetics to allow for a return to ambulatory status. These patients also have increased contact with the healthcare system and often undergo additional wound care therapy prior to revision, efforts that could have been avoided with proper initial selection of LOA. Finally, although rates of re-amputation are abundantly reported, no investigations have been published regarding how often physician awareness of the risk for re-amputation leads to overly aggressive selection of LOA to more proximal levels. Indeed, it is feasible that certain patients may receive amputations at a level more proximal to that which is necessary because their surgeon could not confidently predict a high likelihood of healing at the more distal level. A device to guide decision-making regarding LOA therefore has the potential to reduce rates of re-amputation as well as to spare tissue for patients facing major amputations.

There are currently no gold-standard tests to determine the healing capacity of the primary wound after amputation in patients with CLI. Many have attempted to find such a gold-standard by local evaluation of the tissue microcirculation alone. Several instruments that are known to accurately determine the perfusion and oxygenation of the skin tissue have been tested in this setting, including TCOM, SPP, and laser Doppler. Yet, microcirculation assessment alone has not resulted in a sufficiently accurate assessment of tissue healing capacity to replace clinical judgment when selecting LOA. Therefore, characterizing the local perfusion and oxygenation of the skin is clearly not enough information to quantify the healing potential of the tissue. What these technologies have all failed to include in their prognostics are the systemic effects of comorbidities that also impact wound healing potential. In fact, nearly two decades ago, one author concluded, regarding selection of appropriate level of amputation in a review of factors affecting wound healing after major CLI amputation that, "there will be no 'golden standard test' to predict the likelihood of healing after a major amputation, since it is not only the tissue blood flow that is related to wound healing. All other factors mentioned in this review [smoking, nutrition, diabetes mellitus, and infection] may also be of importance. The combination of clinical judgment and various tests therefore will be the commonest approach."

Despite that author's prediction, the disclosed technology includes an imaging device with the capability to integrate information gleaned from objective tests characterizing the physiology of tissue blood flow with important patient health metrics. The aforementioned problems, among others, are addressed in some embodiments by the machine learning techniques (also known as artificial intelligence, computer vision, and pattern recognition techniques) of the present disclosure that combine optical microcirculatory assessment with overall patient health metrics to generate prognostic information. Using this method, the disclosed devices can provide a quantitative assessment of wound healing potential whereas the current clinical practice standards are only capable of qualitative assessment. The disclosed technology can accurately identify the tissue healing potential at the amputation site to assist the physician's selection of the optimal LOA.

Accordingly, one aspect relates to a tissue classification system comprising at least one light emitter configured to emit light sequentially at each of a plurality of wavelengths to illuminate a tissue region, each of the at least one light emitter being configured to emit spatially-even light; at least one light detection element configured to collect the light reflected from the tissue region after being emitted from the at least one light emitter; one or more processors in communication with the at least one light emitter and the at least one light detection element and configured to: select, based on at least one patient health metric value, a classifier from a plurality of classifiers each trained from a different subset of a set of training data, the training data of the selected classifier including data from other patients having the at least one patient health metric value; control the at least one light emitter to sequentially emit each of the plurality of wavelengths of light; receive a plurality of signals from the at least one light detection element, a first subset of the plurality of signals representing light sequentially emitted at the plurality of wavelengths reflected from the tissue region, and a second subset of the plurality of images representing light of a same wavelength reflected from the tissue region at a plurality of different times; generate, based on at least some of the plurality of signals, an image having a plurality of pixels depicting the tissue region; for each pixel of the plurality of pixels depicting the tissue region determine, based on the first subset of the plurality of signals, a reflectance intensity value at the pixel at each of the plurality of wavelengths, determine, based on the second subset of the plurality of signals, a PPG amplitude value at the pixel, and determine a classification of the pixel by inputting the reflectance intensity value and PPG amplitude value into the selected classifier, the classification associating the pixel with one of a plurality of tissue categories; and generate, based on the classification of each pixel, a mapping of the plurality of tissue categories over the plurality of pixels depicting the tissue region.

In some embodiments, the one or more processors are configured to output a visual representation of the mapping for display to a user. In some embodiments, the visual representation comprises the image having each pixel displayed with a color selected based on the classification of the pixel, wherein pixels associated with each of the plurality of tissue categories are displayed in different colors.

In some embodiments, the plurality of tissue categories comprise a viable tissue category, a necrotic tissue category, and a tissue having small vessel disease category. In some embodiments, generating the mapping comprises identifying regions of the plurality of pixels depicting the tissue region associated with each of the viable tissue category, the necrotic tissue category, and the tissue having small vessel disease category. In some embodiments, the one or more processors are configured to output the image for display, wherein the plurality of pixels depicting the tissue region are displayed in different colors corresponding to the identified regions. In some embodiments, the one or more processors are configured to determine, based on the identified regions, a recommended location of an amputation.

In some embodiments, the one or more processors are configured to determine, based on the plurality of signals, a melanin index of the tissue region. In some embodiments, the one or more processors are configured to select the classifier based on at least the melanin index.

Another aspect relates to a tissue classification method comprising selecting, based on at least one patient health metric value, a classifier from a plurality of classifiers each trained from a different subset of a set of training data, the training data of the selected classifier including data from other patients having the at least one patient health metric value; receiving a plurality of signals from at least one light detection element positioned to receive light reflected from a tissue region, a first subset of the plurality of signals representing light sequentially emitted at a plurality of wavelengths reflected from the tissue region, and a second subset of the plurality of images representing light of a same wavelength reflected from the tissue region at a plurality of different times; generating, based on at least a portion of the plurality of signals, an image having a plurality of pixels depicting the tissue region; for each pixel of the plurality of pixels depicting the tissue region determining, based on the first subset of the plurality of signals, a reflectance intensity value at the pixel at each of the plurality of wavelengths, determining, based on the second subset of the plurality of signals, a PPG amplitude value at the pixel, and determining a classification of the pixel by inputting the reflectance intensity value and PPG amplitude value into the selected classifier, the classification associating the pixel with one of a plurality of tissue categories; and generating, based on the classification of each pixel, a mapping of the plurality of tissue categories over the plurality of pixels depicting the tissue region.

Some embodiments further comprise determining, based on the plurality of signals, a melanin index of the tissue region. Some embodiments further comprise selecting the classifier based on at least the melanin index.

In some embodiments, wherein generating the mapping comprises identifying regions of the plurality of pixels depicting the tissue region associated with each of the viable tissue category, the necrotic tissue category, and the tissue having small vessel disease category. Some embodiments further comprise outputting the image for display, wherein the plurality of pixels depicting the tissue region are displayed in different colors, patterns, or other suitable visual representations corresponding to the identified regions.

Another aspect relates to a method of identifying a recommended location of an amputation, the method comprising selecting a patient having a tissue region in need of amputation; programmatically controlling, via one or more hardware processors, an imaging system to capture data representing a plurality of images of the tissue region, the data representing the plurality of images including a first subset each captured using light of a different one of a number of different wavelengths reflected from the tissue region, and a second subset sequentially captured at a number of times; generating, based on at least one of the plurality of images, an image having a plurality of pixels depicting the tissue region; for each pixel of the plurality of pixels depicting the tissue region determining, based on the first subset of the data representing the plurality of images, a reflectance intensity value at the pixel at each of the plurality of wavelengths, determining, based on the second subset of the data representing the plurality of images, a PPG amplitude value at the pixel, and determining a classification of the pixel by at least inputting the reflectance intensity value and PPG amplitude value into a classifier, the classification associating the pixel with one of a plurality of tissue categories; and identifying, based on the classification of each pixel, the recommended location of the amputation within the tissue region.

Some embodiments further comprise identifying a value of at least one patient health metric of the patient. Some embodiments further comprise inputting the value of the at least one patient health metric into the classifier to determine the classification of each pixel. Some embodiments further comprise selecting, based on the value of the at least one patient health metric, the classifier from a plurality of classifiers each trained from a different subset of a set of training data, the training data of the selected classifier including data from other patients having a same value for the at least one patient health metric.

Some embodiments further comprise generating, based on the classification of each pixel, a mapping of the plurality of tissue categories over the plurality of pixels depicting the tissue region. Some embodiments further comprise outputting a visual representation of the mapping to a user, wherein identifying the recommended location for the amputation is based at least partly on the visual representation of the mapping.

In some embodiments, identifying the recommended location for the amputation is performed programmatically by the one or more hardware processors.

Another aspect relates to a method of training a convolutional neural network to classify tissue regions of an amputation site, the method comprising: receiving training data representing a plurality of images of the amputation site, the data representing the plurality of images including a first subset each captured using light of a different one of a number of different wavelengths reflected from the amputation site, and a second subset sequentially captured at a number of times under a same wavelength as one another; providing the training data as a three-dimensional volume to an input layer of the convolutional neural network, the three-dimensional volume having a height and width corresponding to a number of pixels of a height and a width of each of the plurality of images and having a depth corresponding to a number of the plurality of images; performing a plurality of convolutions at plurality of encoder convolutional stages and a plurality of decoder convolutional stages of the convolutional neural network, wherein a first encoder convolutional stage of the plurality of encoder convolutional stages includes the input layer as a first convolutional layer;

providing an output of a last decoder convolutional stage of the plurality of decoder convolutional stages to a softmax layer of the convolutional neural network; based on an output of the softmax layer, generating a classification value for each pixel across the height and width of the plurality of images; comparing the classification value to each pixel to a ground truth classification of the pixel in a ground truth image, wherein the ground truth classification is based on physician analysis of the amputation site; based on results of the comparing, identifying any errors in the classification values of the pixels; and adjusting at least one weight of the plurality of convolutions based at least partly on back propagating the errors through the convolutional neural network.

In some embodiments, generating the classification comprises classifying each pixel as one of background, healthy tissue, diseased tissue, or necrotic tissue.

In some embodiments, the first subset of the plurality of images includes eight images each captured using light of a different one of eight different wavelengths, and wherein the second subset of the plurality of images includes hundreds of images captured sequentially at the same wavelength at a rate of 30 frames per second.

In some embodiments, each of the plurality of encoder convolutional stages and each of the plurality of decoder convolutional stages comprises at least two convolutional layers each followed by a rectified linear unit layer.

In some embodiments, performing the plurality of convolutions comprises, at each encoder convolutional stage of the plurality of encoder convolutional stages, performing at least a first encoder convolution, providing an output of the first encoder convolution to a rectified linear unit layer, and downsampling an output of the rectified linear unit layer using a max pooling layer; and, at each decoder convolutional stage of the plurality of decoder convolutional stages, receiving a pool mask from the max pooling layer of a corresponding one of the plurality of encoder convolutional stages, and performing at least a first decoder convolution based at least partly on the pool mask.

Another aspect relates to a method of using a convolutional neural network to classify tissue regions of a potential amputation site, the method comprising receiving data representing a plurality of images of the potential amputation site, the data representing the plurality of images including a first subset each captured using light of a different one of a number of different wavelengths reflected from the potential amputation site, and a second subset sequentially captured at a number of times under a same wavelength as one another; providing the data as a three-dimensional volume to an input layer of the convolutional neural network, the three-dimensional volume having a height and width corresponding to a number of pixels of a height and a width of each of the plurality of images and having a depth corresponding to a number of the plurality of images; performing at least one convolution on the three-dimensional volume; providing an output of the at least one convolution to a softmax layer of the convolutional neural network; based on an output of the softmax layer, generating a classification value for each pixel across the height and width of the plurality of images; and based on the classification value for each pixel, generating a mapping of a plurality of tissue classifications of tissue at the potential amputation site.

In some embodiments, generating the classification comprises classifying each pixel as one of background, healthy tissue, diseased tissue, or necrotic tissue.

In some embodiments, the first subset of the plurality of images includes eight images each captured using light of a different one of eight different wavelengths, and wherein the second subset of the plurality of images includes hundreds of images captured sequentially at the same wavelength at a rate of 30 frames per second.

In some embodiments, performing at least one convolution comprises performing a plurality of convolutions at plurality of encoder convolutional stages and a plurality of decoder convolutional stages of the convolutional neural network, wherein a first encoder convolutional stage of the plurality of encoder convolutional stages includes the input layer as a first convolutional layer. In some embodiments, performing the plurality of convolutions comprises, at each encoder convolutional stage of the plurality of encoder convolutional stages, performing at least a first encoder convolution, providing an output of the first encoder convolution to a rectified linear unit layer, and downsampling an output of the rectified linear unit layer using a max pooling layer; and, at each decoder convolutional stage of the plurality of decoder convolutional stages, receiving a pool mask from the max pooling layer of a corresponding one of the plurality of encoder convolutional stages, and performing at least a first decoder convolution based at least partly on the pool mask. In some embodiments, each of the plurality of encoder convolutional stages and each of the plurality of decoder convolutional stages comprises at least two convolutional layers each followed by a rectified linear unit layer.

In some embodiments, the convolutional neural network is trained using the method described above.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements. The patent or application file contains at least one drawing executed in color. Copies of this patent or patent application publication with color drawing(s) will be provided by the Office upon request and payment of the necessary fee.

DETAILED DESCRIPTION

Introduction

Figure 1A:
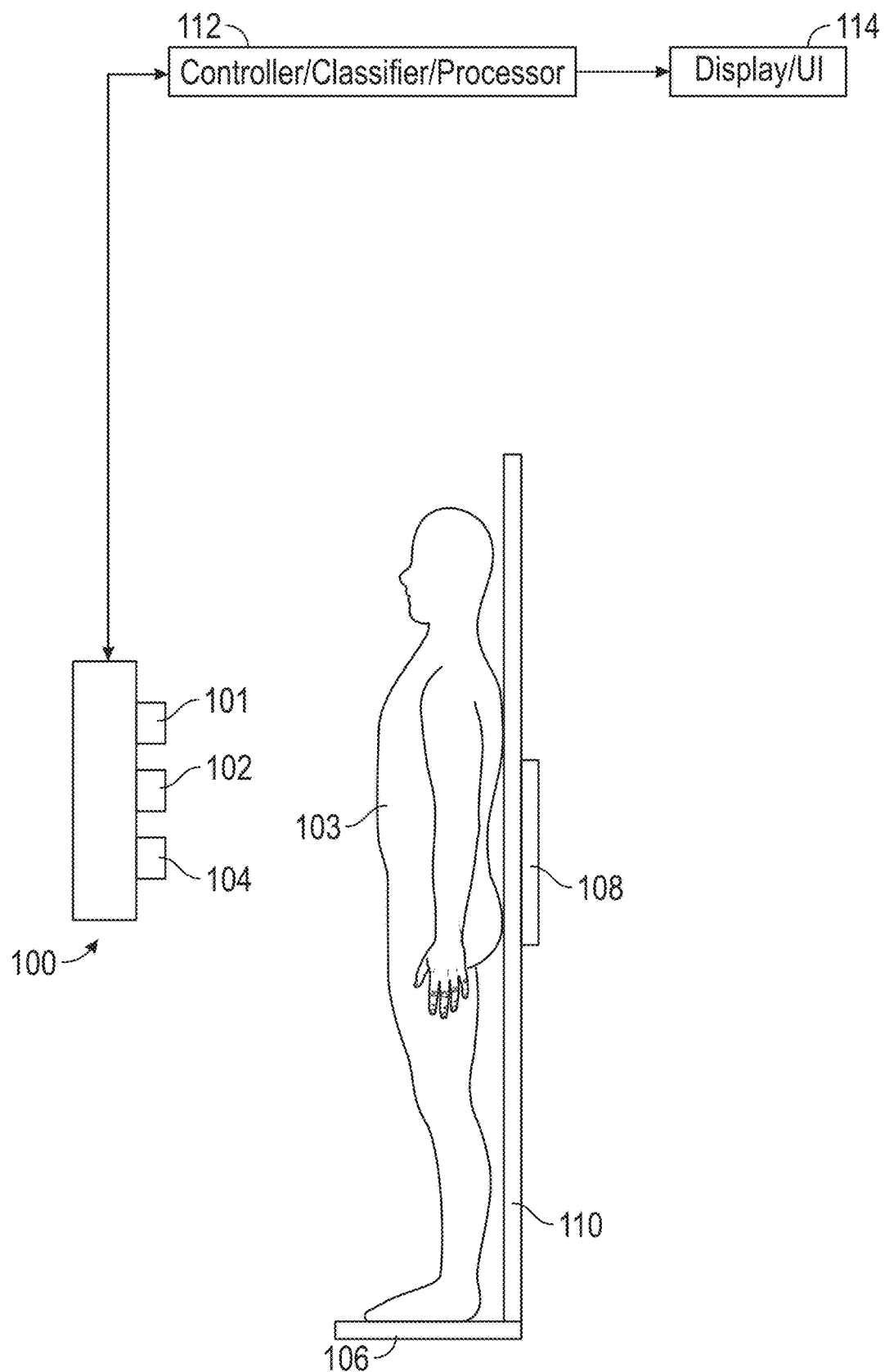
FIG. 1A illustrates example components of an imager that is imaging a subject.

Aspects of the disclosure relate to a non-contact, non-invasive, non-radiation imaging device for classifying tissue at an amputation site and/or quantitatively selecting the appropriate level or region of amputation (LOA), for example for patients with peripheral arterial disease (PAD). More than 150,000 patients in the United States undergo lower extremity amputations every year secondary to peripheral arterial disease (PAD). Surgeons prefer to salvage as much limb tissue as possible during amputation to increase patient mobility while decreasing morbidity and mortality. However, clinicians must balance this preference against the likelihood of primary wound healing at a given LOA, which decreases with more distal amputations. As used herein, "distal" can refer to a tissue region farther from the LOA into the tissue region being amputated from the patient, while "proximal" can refer to a tissue region at the LOA or closer to tissue that is not being amputated from the patient. There are no gold-standard tests for selection of LOA in patients with PAD, therefore reported rates of re-amputation in current practice are significant. Around 10% of above-the-knee amputations and around 35% of foot amputations require revision to a more proximal level. Furthermore, physician awareness of the risk for re-amputation may lead to overly aggressive selection of LOA to more proximal levels in some cases. Indeed, certain patients may receive amputations at a level more proximal than is necessary because their surgeon could not confidently predict a high likelihood of healing at a more distal level. In current practice, selection of LOA is determined qualitatively by clinical judgment of the surgeon using patient history and physical exam. Accordingly, there is a need for systems that provide physicians with quantitative information regarding patient tissue health and healing potential in the LOA selection process. The disclosed devices and techniques provide a quantitative assessment for selection of LOA by integrating photoplethysmography, multispectral imaging, and/or patient-specific health metric values to classify tissue based on microvascular blood flow using a machine learning model.

A diagnostic device as described herein provides a point of care perfusion imaging system that provides diagnostic images derived from optical measurements of tissue perfusion. The device is non-contact, non-invasive, non-laser, and non-radiation. The device can simultaneously or sequentially perform two optical imaging methods to obtain blood flow assessment: photoplethysmographic (PPG) imaging and multispectral imaging (MSI). These optical measurements are integrated using a machine learning model, and in some embodiments patient health metric values are integrated as well, in order to quantitate likelihood of amputation site healing at a given LOA. Nursing staff can be easily trained to perform the imaging test on this user-friendly device. The imaging of multiple limb levels with the device can take approximately ten minutes in total. Results are immediately available and stored electronically for physician review at a later time.

If used for routine assessment of patients prior to amputation at this sensitivity and specificity, the disclosed diagnostic devices and techniques can reduce the rate of re-amputation by around 67%, which would result in 10,000 fewer re-amputations per year while both improving quality of life for amputees and reducing health costs associated with their care. For example, quality of life can be improved for amputees using the disclosed technology by reducing the rate of secondary amputations due to failed healing and/or by selecting LOA locations that can provide improved healing time compared to qualitatively assessed LOA locations.

The PPG imaging of the disclosed devices and techniques can capture over one million unique photoplethysmogram signals across a large area of tissue. The PPG signal can be generated by measuring light's interaction with dynamic changes in vascularized tissue. Vascularized tissue expands and contracts in volume by approximately 1-2% with each incoming systolic blood pressure wave at the frequency of the cardiac cycle. This influx of blood increases the volume of the tissue and brings additional hemoglobin proteins that strongly absorb light. Therefore, the total absorbance of light within the tissue oscillates with each heartbeat. In order to generate images from PPG signals detected by the disclosed imaging devices, the techniques described herein can take advantage of light's pathway through the tissues. For example, a small portion of light incident on the tissue surface scatters into the tissue. A fraction of this scattered light exits the tissue from the same surface it initially entered. Using a sensitive digital camera, this back-scattered light can be collected across an area of tissue so that each pixel in the image data contains a unique PPG waveform determined by changes in intensity of the scattered light. To generate a 2-D visual map of relative tissue blood flow, the average amplitude of each unique waveform over many heart beat samples can be measured. Therefore, a major benefit of this technology is that it allows for measurement and mapping of microvascular blood flow, which is critical for wound healing.

The multispectral imaging (MSI) of the disclosed devices and techniques can measure the reflectance of select wavelengths of visible and near-infrared (NIR) light (400 nm-1,100 nm) from a tissue's surface. MSI can be effective for quantifying key tissue properties relevant to a number of pathologies, such as amputation, burns, diabetic ulcers, and skin cancers (e.g., melanoma, squamous cell carcinoma, and basal cell carcinoma), to name a few examples, because it can quantify the volume fraction of hemoglobin and the presence of oxygenated hemoglobin, among other tissue characteristics. The wavelengths of light employed by the disclosed devices can be selected based on well-established characterizations of light-tissue interaction. For example, melanin within the stratum corneum and the epidermis mainly absorbs UV and visible wavelengths. NIR wavelengths (700-5000 nm) are the least absorbed by melanin and have been found to be the best at penetrating through the dermis to determine its depth. Hemoglobin is largely contained by vessels coursing through the dermis, and its concentration determines the degree of dermal absorption of wavelengths greater than 320 nm. Hemoglobin absorption of light also changes depending on whether the molecule is oxygenated for deoxygenated. As tissue melanin, hemoglobin concentration, and the oxygenated hemoglobin fraction are altered by disease states, MSI is able to detect changes in the resulting reflectance spectrum.ABnormal skin tissue can be identified by changes in its reflectance spectrum as compared to healthy tissue. Thus, MSI allows for the quantitative differentiation and mapping of viable versus non-viable skin tissue, which is important for healing of amputation or excision sites.

Alternatives of the disclosure relate to systems and techniques for identifying, evaluating, and/or classifying a subject's tissue. Some alternatives relate to apparatuses and methods for classifying a tissue, wherein such devices include optical imaging components. Some of the alternatives described herein comprise reflective mode multi-spectral time-resolved optical imaging software and hardware, which when implemented allow for several of the methods of tissue classification provided herein.

Alternatives described herein allow one to assess and classify in an automated or semi-automated manner tissue regions of subjects that may require amputation, and may also provide treatment recommendations. Some of the alternatives described herein are particularly suited for amputation level assessment because they allow doctors to quickly and quantitatively evaluate the status of tissue around an amputation site so that a level of amputation decision can be made quickly and accurately. Some alternatives may also assist a surgeon in selecting nearby healthy tissue to cover the amputation site.

Throughout this specification reference is made to a wound or wounds. It is to be understood that the term "wound" is to be broadly construed and encompasses open and closed wounds in which skin is torn, cut, punctured, or diseased, or wherein trauma causes a contusion, a superficial lesion, or a condition or imperfection on the skin of a subject, for example a human or animal, in particular a mammal. A "wound" is also intended to encompass any damaged region of tissue, wherein fluid may or may not be produced as a result of an injury or disease. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers, skin cancer (e.g., melanoma, squamous cell carcinoma, basal cell carcinoma) or the like are also referred to herein as wounds in some contexts. It will be appreciated that the machine learning classifier described herein can be trained to categorize tissue states of tissue regions including (or suspected of including) any of these types of wounds, based on identifying ground-truth classification of similar images in a training data set.

Various alternatives will be described below in conjunction with the drawings for purposes of illustration. It should be appreciated that many other implementations of the disclosed concepts are possible, and various advantages can be achieved with the disclosed implementations. All possible combinations and subcombinations are intended to fall within the scope of this disclosure. Many of the alternatives described herein include similar components, and as such, these similar components can be interchanged in different aspects of the invention.

Headings are included herein for reference and to aid in locating various sections. These headings are not intended to limit the scope of the concepts described with respect thereto. Such concepts may have applicability throughout the entire specification.

Overview of Example Imaging System Alternatives

Figure 1B:
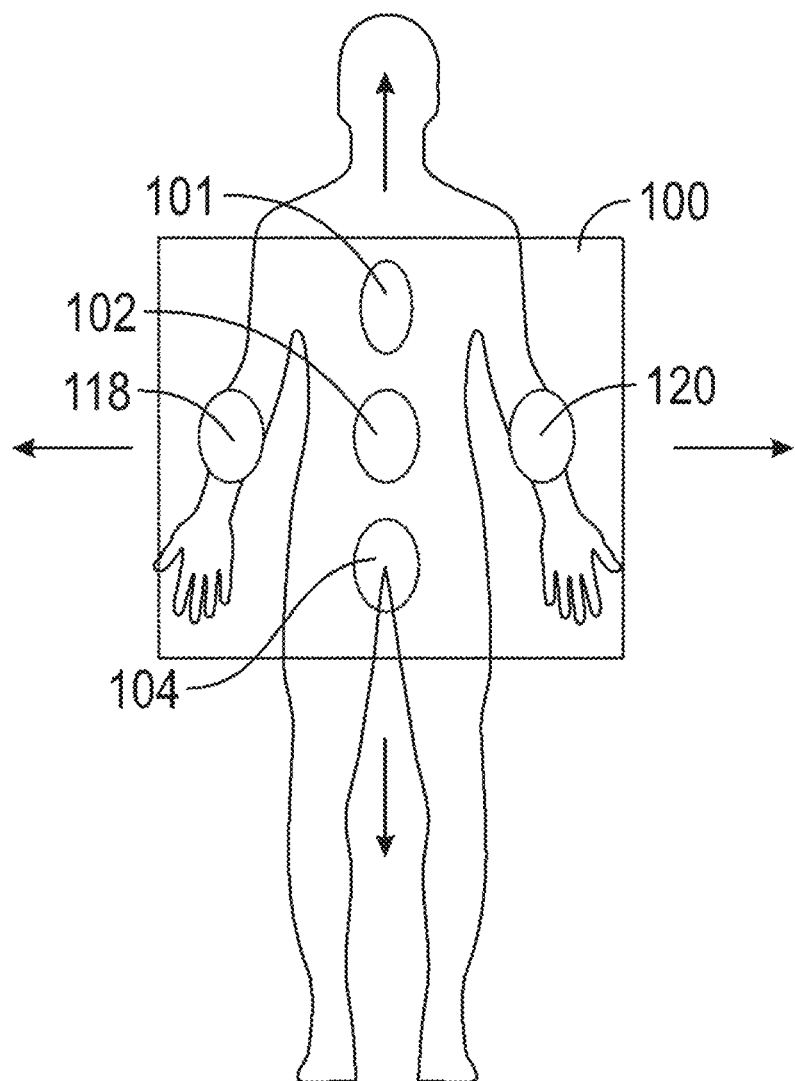
FIG. 1B is an illustration of example movements of an example imaging probe.

FIGS. 1A and 1B illustrate an example of one alternative of the present invention. The apparatus shown in these figures is especially suited for whole or partial body assessment of patients awaiting amputation. This apparatus is especially useful for amputation level assessment functions, where clinical decisions related to amputation locations are being made. In this example, probe 100 comprises one or more light sources, in this case four light sources 101, 104, 118 and 120, and image acquisition device 102. Light sources 101, 104, 118, and 120 illuminate the tissue region, in this case, tissue 103, which advantageously includes the entire body surface of the subject facing the probe 100. In some alternatives, the one or more light sources may be light-emitting diodes (LEDs), halogen lamps, tungsten lamps, or any other illumination technology. The one or more light sources may emit white light or light that falls in one or more spectral bands that can be selected as desired by a user.

Many LEDs produce light in narrow bandwidths (e.g., full-width at half-maximum of 50 nm or less), wherein the specific LEDs can be chosen to illuminate at specific bandwidths. In general, the one or more spectral bands may be chosen in view of the light measurements most relevant to the kind of data sought and/or the clinical application. The one or more light sources may also be coupled to one or more drivers to power the light sources and control them. These drivers may be part of the light sources themselves, or separate. Multiple narrowband light sources or broadband light sources with selectable filters (e.g. filter wheels) may be used to serially or simultaneously illuminate the tissue 103 with light in multiple spectral bands. The center wavelength of the chosen spectral bands typically reside in the visible and near-infrared wavelengths, such as between 400 nm to 1100 nm e.g., less than (but not zero), at least, or equal to 400, 500, 600, 700, 800, 900, 1000, or 1100 nm or a range defined by any wavelength between any two of the aforementioned wavelengths.

In some alternatives, the light sources illuminate the tissue region with substantially uniform intensity over the area of the illuminated tissue region (referred to herein as "spatially-even" light or illumination). For example, substantially uniform intensity can be achieved by using light diffusers provided as part of the light sources 101, 104, 118 and 120 that create an approximately uniform distribution of the light intensity applied to the tissue 103. Light diffusers also have the additional benefit of reducing undesirable specular light reflection. In some instances, significant improvements to signal-to-noise ratios of the signals obtained by the image acquisition device 102 can be achieved by utilizing broad spectral spatially-even illumination patterns with high powered LEDs, for example cross polarization filters. In some cases, patterned light systems, such as checkerboard patterned illumination may be used as well. In certain such alternatives, the field of view of the image acquisition device is directed to tissue regions that have not been directly illuminated by the light sources, but are adjacent to the illuminated areas. For example, where light of substantially uniform intensity is used, an image acquisition device, such as image acquisition device 102, may read light from outside the illuminated region. Similarly, where checkerboard-patterned illumination is used, for example, the acquisition device 102 may read light from the non-illuminated portions of the checkerboard.

Moreover, even though light of substantially uniform intensity was effective in some alternatives described herein, other alternatives may also use non-uniform light, wherein the one or more lights are positioned so as to minimize differences in light intensity across the surface. In some cases, these differences may also be accounted for during data acquisition or by backend software or hardware logic. For example, top-hat transformations or other image processing techniques may be used to compensate for non-uniform background illumination.

In certain alternatives, the light may be desirably polarized. In some cases, the light is polarized using reflection, selective absorption, refraction, scattering and/or any method of polarizing light known in the art. For example, the polarization may utilize prisms (such as a Nicol prism), mirrors and/or reflective surfaces, filters (such as a Polaroid filter), lens, and/or crystals. The light may also be cross-polarized or co-polarized. In some alternatives, the light from the one or more light sources is polarized before the light illuminates the subject. For example, polarizing filters may be provided as part of the light sources 101, 104, 118, and 120. In some alternatives, reflected light from the tissue is polarized after it has been reflected from the tissue. For example, polarized filters may be provided as part of acquisition device 102. In other alternatives the light is polarized both before it illuminates the subject and after it is reflected. For example, polarizing filters may be provided as part of light sources 101, 104, 118, and 120, as well as part of data acquisition device 102.

The type of polarization technique used may depend on factors such as the angle of illumination, the angle of reception, the kind of illumination source used, the kind of data desired (e.g., measurements of light scattered, absorbed, reflected, transmitted, and/or fluoresced), and the depth of tissue imaged. For example, when tissue is illuminated, some light may be reflected off the top layer of skin directly as surface glare and reflectance. This reflected light often has a different polarity than the light that diffuses into dermal tissue, where the light may be scattered (e.g., reflected) and change direction and polarity. Cross-polarization techniques may be used to minimize the amount of glare and reflectance read by an acquisition device while maximizing the amount of backscattered light read. For example, polarization filters may be provided as part of light sources 101, 104, 118, and 120, as well as part of data acquisition device 102. In such a setup, the light is first polarized before it illuminates the target 103. After the light is reflected from target 103, the reflected light may then be polarized in a direction orthogonal to the first polarization in order to measure the backscattered light while minimizing the amount of incident light reflected off the surface of the target 103 that is read.

In some circumstances, it may also be desirable to image tissue at certain depths. For example, imaging tissue at particular depths can be used in evaluating particular wounds at particular depths, locating and/or identifying the presence or absence of a cancerous tumor or determining the stage of a tumor or progression of cancer, or any of the other therapeutic applications mentioned in this disclosure. Certain polarization techniques known in the art may be used to selectively image tissue at certain depths based on optical properties and/or mean free path lengths.

In certain alternatives, other techniques for controlling imaging depth may be used. For example, the optical scattering properties of tissue change with temperature while the light penetration depth in skin increases with cooling. As such, the depth of imaging may be controlled by controlling the temperature of the imaged tissue region. Also, for example, the depth of imaging may be controlled by pulsing (or flashing) light sources at various frequencies. Pulsing light penetrates deeper into the skin than non-pulsing light: the longer the pulse widths, the deeper the light penetration. As another example, the imaged depth may also be changed by adjusting the intensity of light, where the penetration of more intense light is greater than less intense light.

As further illustrated in FIG. 1A, image acquisition device 102 is configured to receive reflected light from the tissue 103. The image acquisition device 102 can detect light from the illuminated region, a sub-region of the illuminated region, or a non-illuminated region. As illustrated further below, the field of view of the image acquisition device 102 may include the entire body surface of the subject facing the probe 100. When the entire subject facing the probe is illuminated and the entire subject facing the probe is in the field of view of the image acquisition device, the speed and ease of classification is enhanced. The image acquisition device 102 may be a two-dimensional charge-coupled device (CCD) or complementary metal-oxide semiconductor (CMOS) image acquisition device with appropriate optics for imaging all or part of the illuminated tissue 103.

Module 112 is a controller, classifier, and processor that may be coupled with probe 100 in some alternatives. Module 112 controls the probe, which may include setting such parameters as its physical location, light intensity, resolution, filter color, or any parameter of the camera and/or light sources described in this disclosure. Module 112 also receives and processes data obtained by the probe, as will be described later in this disclosure.

Module 112 may be further coupled with a module 114 in some alternatives, where module 114 is a display and user interface ("UI"). The display and UI shows information and/or data to the user, which in certain alternatives includes the presence of a tissue condition, the severity of the tissue condition, and/or additional information about the subject, including any of the information mentioned in this specification. Module 114 receives user inputs, which in certain alternatives includes information about the patient such as age, weight, height, gender, race, skin tone or complexion, and/or blood pressure. Module 114 may also receive user inputs with calibration information, user selections of locations to scan, user selections of tissue conditions, and/or additional information for diagnoses, including any of the information mentioned in this disclosure. In certain alternatives, some or any of the aforementioned user inputs may be sent automatically to module 112 without the user entering information using module 114.

As illustrated in FIG. 1B, the probe 100 may in some alternatives be moved in any direction or combination of directions, such as up, down, left, right, diagonally up-right, diagonally up-left, diagonally down-right, diagonally down-left, or any combination of these directions. In some alternatives, the probe may also be moved in a direction normal to the subject, where the probe gets closer or farther away from the subject. The probe may, for example, be coupled to rails or an articulating arm with position controlled manually or automatically by the controller 112 or a combination of both. In some alternatives, either the light sources or the image acquisition device may be fixed, and in other alternatives, either may be movable independently. Certain alternatives couple the image acquisition device with a motor to automate the movement of the image acquisition device so as to allow the camera to image each section of the subject. The camera can also be coupled to rails, tracks, guides, and/or actuatable arms. The light source(s) may illuminate the entire tissue area 103 while the image acquisition device moves, or the light source(s) may be controlled during a scanning process to only illuminate a desired tissue portion that the camera is imaging.

In the alternative shown in FIG. 1A, the subject stands in an upright position against a backdrop 110 as images of the subject or a portion thereof (e.g., the entire body of the subject or a desired tissue location) are acquired. In some alternatives, the backdrop 110 is a support structure that the subject lies on or against in a horizontal or angled position as the images are acquired. Scales 106 and 108 may be provided to weigh the subject as the images are acquired. In addition or alternatively to scales, other biometric readers for measuring heart rate, temperature, body composition, body mass index, body shape, blood pressure and other physiological data may be provided.

Figure 2:
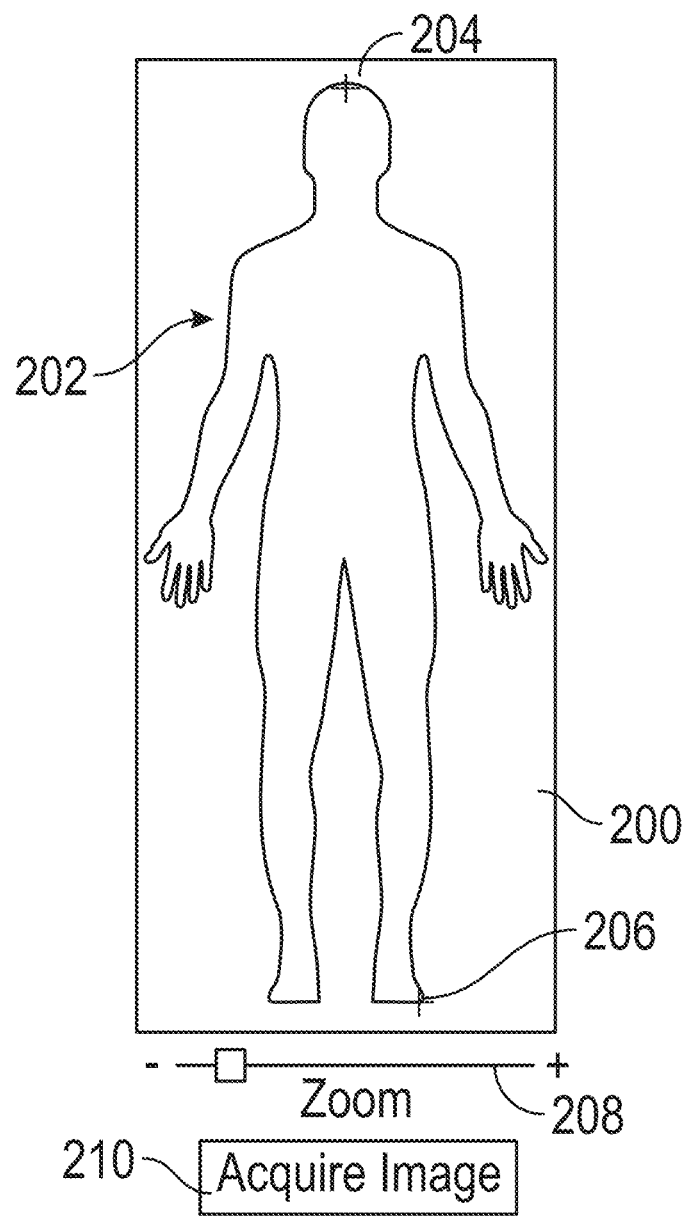
FIG. 2 is an illustration of an example user interface for acquiring an image.

FIG. 2 shows an example UI 200 presented on display/UI 114 for acquiring an image with the apparatus. In this alternative, the user interface displays the field of view of the image acquisition device when the tissue 103 is being illuminated by the light sources. In certain alternatives, the user may position the field of view of the image acquisition device 102 so as to include the entire subject 202. The user may use zoom component 208 to adjust the image acquisition device 102 so that the subject nearly fills the field of view. In some alternatives, the user may use the user interface to obtain other information about the subject 202. For example, the user may select position 204 and position 206 in order to measure the height of the subject. In some cases, the user instructs the image acquisition device to acquire images of the subject using the user interface, such as by pushing an acquire image button 210.

When acquiring images of the subject to perform tissue classification using those images, the light sources (with associated filters if provided) and image acquisition device are controlled to acquire multiple images of the subject, with the separate images being associated with different spectral bands of reflected light and/or separated in time. Images acquired at different spectral bands may be processed according to image processing techniques for spectral domain data (e.g., MSI techniques) to classify tissue regions, and images separate in time may be processed according to image processing techniques for time domain data (e.g., PPG techniques) to classify tissue. In some alternatives, both types of image sets are acquired, and the results are merged to perform a more accurate classification, as described further below.

For amputation patients, image acquisition may be performed with the subject in multiple orientations, such as front facing, rear facing, left side facing, and right side facing. The patient may stand in these various orientations against the backdrop 110, or if the backdrop 110 is a support structure in a horizontal orientation, the patient may lay in different orientations on the backdrop 110. The data from the acquired images is then used to classify different areas of the skin of the subject as likely to heal after amputation or not, and may classify specific types of tissue in potential amputation areas as well.

Following image acquisition in different orientations, the controller/classifier/processor 112 may process the image data for each subject orientation. When the backdrop 110 is a characteristic color different from skin tissue, the controller/classifier/processor may separate the subject from the background, assigning each pixel in each acquired image as either background or subject. As another alternative, the UI can be used to trace the outline of the subject (with a stylus on a touchscreen or a mouse and cursor for example) in the initial image (e.g., such as shown in FIG. 2) to distinguish the background from the subject. When the pixels of the image associated with the subject are identified, these may be analyzed using MSI and/or PPG techniques to classify areas of the skin of the subject according to microvascular status.

Turning now to specific apparatus and methods that may be used for illuminating tissue, acquiring images, and analyzing the image data, it will be appreciated that in some instances, PPG alone does not fully classify tissue because it only makes volumetric measurements. Also, multispectral imaging (MSI) has been used to discern differences in skin tissue but this technique does not fully classify tissue. With current MSI technology, it can often be challenging to account for variations due to skin types, differences of skin in different body areas, and possible pre-treatment of wounds. MSI alone may also not give an overall assessment of a skin condition because it only measures skin appearance or the constituents of the skin, and not dynamic variables important to skin classification, such as the availability of nutrients and oxygen to the tissue.

Some alternatives described herein combine MSI and PPG to improve the speed, reliability, and accuracy of skin classification. The alternatives described herein can use, for example, image data to measure the contributions of blood, water, collagen, melanin, and other markers to develop a more refined view of the skin's structure and ability to properly function, as in a normal state, as opposed to skin that has suffered disease or trauma. In addition, alternatives described herein also detect variations in light reflected from the skin over time, which allows one to gain significant physiological information allowing a clinician to rapidly assess tissue viability and features such as blood perfusion and oxygenation at a tissue site.

Figure 3:
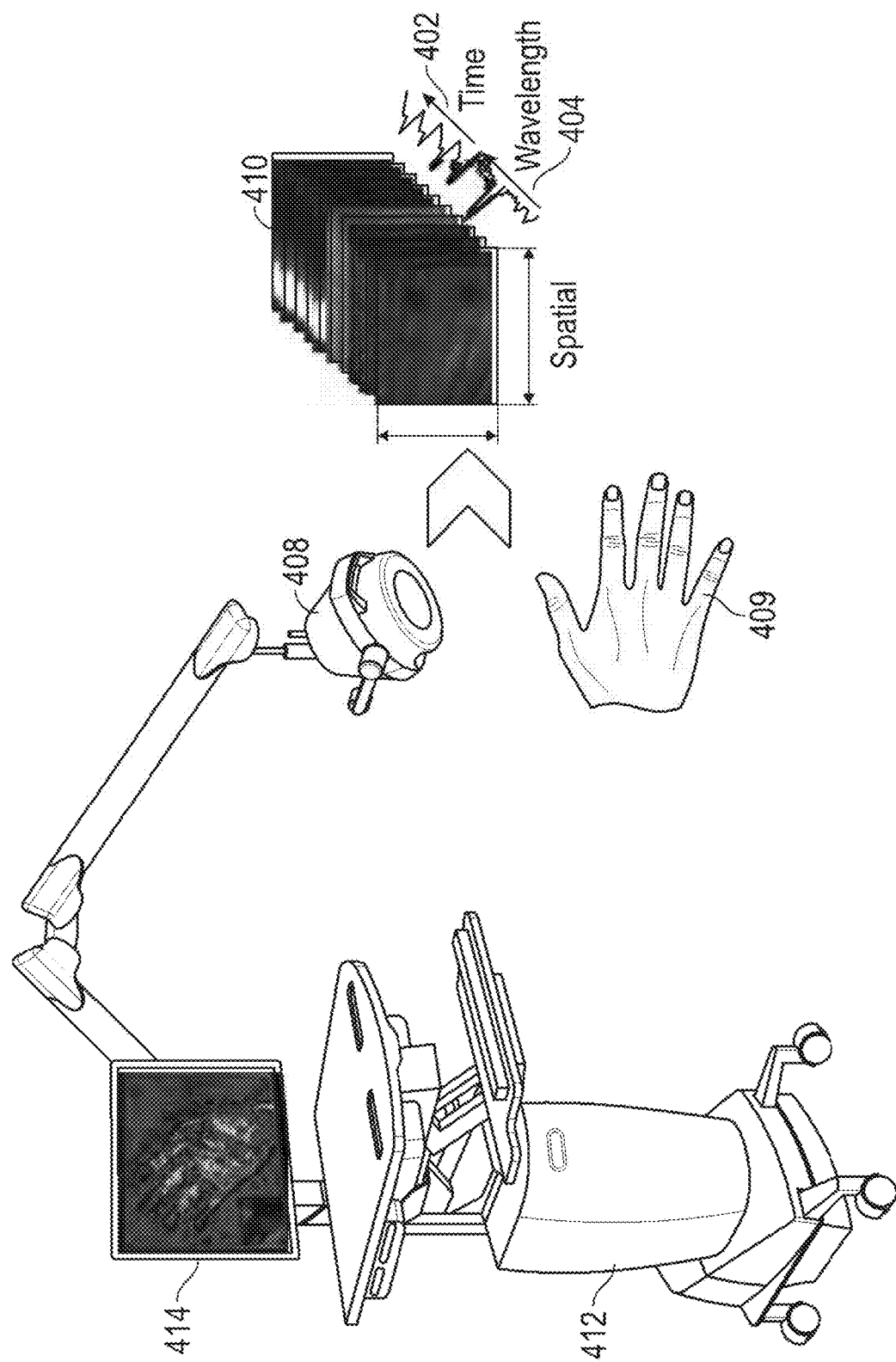
FIG. 3 is an example illustration of the high resolution multi-spectral video camera used in some alternatives described herein, and the data that can be obtained.

FIG. 3 illustrates a system that can be (but is not necessarily) used as the probe 100, controller/classifier/processor 112 and display/UI 114 in some alternatives. The system of FIG. 3 described below, with its combination of MSI and PPG technologies, can also be used to analyze and classify tissue regions of smaller areas as well with higher accuracy than previously available, and need not be used only in association with the whole body analysis systems and methods described above.

In the system of FIG. 3, probe 408 includes one or more light sources and one or more high resolution multi-spectral cameras that record a target tissue region 409 with a plurality of images while maintaining temporal, spectral, and spatial resolutions to perform highly accurate tissue classifications. Probe 408 can comprise multiple cameras and imagers, prisms, beam-splitters, photodetectors, and filters, as well as light sources of multiple spectral bands. The camera(s) can measure scattering, absorption, reflection, transmission, and/or florescence of different wavelengths of light over time from the tissue region. The system also comprises a display/UI 414, and a controller/classifier/processor 412 that controls the operation of the probe 408, receives inputs from the user, controls the display outputs, and performs the analysis and classification of image pixels.

Data set 410 is an example output of probe 408, which contains data regarding reflected light of different wavelengths and at different times for imaged spatial locations. An example of data regarding light of different wavelengths for imaged spatial locations is shown in data subset 404. Data subset 404 may include multiple images of the tissue region, each measuring light reflected from the tissue region in a different selected frequency band. The multiple images of data subset 404 may be acquired simultaneously or essentially simultaneously, where essentially simultaneously means within one second of each other. An example of data regarding reflected light from the tissue region at different times for imaged spatial locations is shown in data subset 402. Data subset 402 includes multiple images taken at different times over a period longer than one second, usually longer than two seconds. The multiple images of data subset 402 may be acquired at a single selected frequency band. In some cases, the multiple images of data subset 404 may be acquired over a time period longer than one second, and the multiple images of data subset 402 may be taken at multiple frequency bands. However, the combined data set including subset 404 and subset 402 includes images taken that correspond to both different times and different frequency bands.

To collect the images of data subset 404, in some alternatives, the one or more cameras are coupled to a filter wheel with a plurality of filters with different passbands. As the one or more cameras acquire images of the tissue region of the subject, the wheel of filters rotates, allowing the one or more cameras to record the subject in different spectral bands by acquiring images synchronized with filter positions of the filter wheel as it rotates. In this way, the camera receives the light reflected at each pixel of the tissue region in different frequency bands. Indeed, in many cases, the filters allow the devices described herein to analyze light in spectrums that would not be distinguishable by the human eye. In many cases, the amount of light reflected and/or absorbed in these various spectrums can give clues about the chemical and physical composition of the subject's tissue or a specific region of the tissue. In some cases, the data obtained using the filters forms three-dimensional data arrays, wherein the data arrays have one spectral and two spatial dimensions. Each pixel in the two spatial dimensions can be characterized by a spectral signature defined by reflected light intensity in each acquired spectral band. The intensity of light at the various wavelengths gives information about the composition of the target because different compositions scatter, absorb, reflect, transmit, and/or fluoresce different frequencies of light differently. By measuring light in these various wavelengths, probe 408 captures this composition information at each spatial location corresponding to each image pixel.

In certain alternatives for acquiring the images at multiple spectral bands for the data set 404, the one or more cameras comprise a hyperspectral line-scan imager. A hyperspectral line-scanner has continuous spectral bands instead of the discrete bands of each filter in a filter wheel. The filters of the hyperspectral line-scanner can be integrated with a CMOS image sensor. In some instances, the filters are monolithically integrated optical interference filters, wherein the plurality of filters is organized in step-wise lines. In some cases, the filters form a wedge and/or a staircase shape. In some instances there may be dozens to hundreds of spectral bands corresponding to wavelengths between 400 to 1100 nm, such as at 400, 500, 600, 700, 800, 900, 1000, or 1100 nm or a range defined by any wavelength that is between any two of the aforementioned wavelengths. The imager scans the tissue using each filter line and senses the light reflected from the tissue through each of those filters.

In still other alternatives, there are other filter systems that can be implemented to filter light in different spectral bands. For example, a Fabry-Perot filter is used in some alternatives, as well as, other filter organization approaches, for example by putting the filters in a tile structure or by depositing the filter directly onto the imaging sensor (CMOS, CCD, etc.) in a pattern such as a Bayer-array or multi-sensor array.

In any case, the passbands of the filters are selected based on the type of information sought. For example, amputation sites might be imaged with wavelengths between 400-1100 nm (such as at 400, 500, 600, 700, 800, 900, 1000, or 1100 nm or a range defined by any wavelength that is between any two of the aforementioned wavelengths) in order to capture the contributions of blood, water, collagen, and melanin from the amputation site and surrounding tissue. In some embodiments, absorbance spectra of approximately or at 515 nm, 750 nm, and/or 972 nm wavelengths can be used, while in other embodiments the absorbance spectra of approximately or at 542 nm, 669 nm, and/or 960 nm wavelengths can be used for distinguishing between tissue classifications.

Healthy skin can include areas of skin that did not have an injury associated with a vascular disease or microcirculatory issue. Hyperemia corresponded to areas of high perfusion, typically tissue that can be expected to heal without treatment. The graftable or tissue flap categorization can correspond to skin that is has greater than a threshold level of microvascular activity. The vascularly diseased category can correspond to a zone of ischemia with decreased perfusion, but potentially salvageable tissue. The necrotic categorization can correspond to regions of irreversible tissue loss where amputation can be desirable.

Alternatives of this disclosure were used to measure light reflected from the tissue samples at various wavelengths in the range 400 nm to 1100 nm (such as at 400, 500, 600, 700, 800, 900, 1000, or 1100 nm or a range defined by any wavelength between any two of the aforementioned wavelengths) in order to determine which sets of wavelengths provided higher amounts of variability between the light reflected from tissues of different type. This variability could be used to effectively separate tissue classes by at least the categories of healthy tissue, hyperemia, suitable skin flaps, vascularly diseased (e.g., small vessel disease), and necrotic. The optimal sets can sometimes be identified as the wavelength sets that contained the maximally relevant wavelengths with the minimum amount of redundancy. In this context, maximum relevance was sometimes found when wavelengths could effectively separate one particular tissue class from the other classes Minimum redundancy was sometimes found by including only one of a plurality of wavelengths that measured the same information. After sets of wavelengths were used to classify the tissue samples, the classifications were compared to accurate assessments of the tissue samples by practitioners.

Data splits across different experiments were used to test classification accuracy. In a first set of experiments, the wavelengths 475, 515, 532, 560, 578, 860, 601, and 940 nm were measured. In a second set of experiments, the wavelengths 420, 542, 581, 726, 800, 860, 972, and 1064 nm were measured. In a third set of experiments, the wavelengths 420, 542, 581, 601, 726, 800, 972, and 860 nm were measured. And in a fourth set of experiments, the wavelengths 620, 669, 680, 780, 820, 839, 900, and 860 nm were measured.

The wavelengths that provided the best variability for tissue classification from the first and second experiment sets were used in order to categorize tissue with 83% accuracy. These wavelengths were (in order of relative weight) 726, 420, 515, 560, 800, 1064, 972, and 581 nm. Similarly, the wavelengths that provided the best variability for tissue classification from the third and fourth experiments were used in order to categorize tissue with 74% accuracy. These wavelengths were (in order of relative weight) 581, 420, 620, 860, 601, 680, 669, and 972 nm. Also, noticeably, the wavelength of 860 nm was particularly effective for both MSI and PPG analysis, and thus, for the combination device. These experimental sets show that wavelengths in the range 400 to 1100 nm (such as at 400, 500, 600, 700, 800, 900, 1000, or 1100 nm or a range defined by any wavelength that is between any two of the aforementioned wavelengths) can be used for effective tissue classification. As previously noted, other sets of wavelengths may be effective as well. For example, the effective wavelength sets in the experiment minimized redundancy. As such, other wavelengths may be used to classify some aspects of the tissue effectively. Also, using the experiment described above, other wavelengths for effectively classifying necrotic tissue and/or any other tissue condition described in this disclosure may be found.

Overall, the experiment described above found that wavelengths in the range 400 to 900 nm (including 400, 500, 600, 700, 800, or 900 nm or a range defined by any wavelength that is between any two of the aforementioned wavelengths) were particularly effective in imaging amputation sites. More particularly, of that range, a set of wavelengths could be constructed to image amputation sites where: at least one (1) wavelength was less than 500 nm; at least two (2) wavelengths were between 500-650 nm; and at least three (3) were between 700-900 nm. This set was effective at imaging amputation sites and separating imaged amputation site tissue into categories.

Also based on the experiment, the below ranking lists each tested wavelength in order of their apparent significance in classification:

TABLE 1

| Rank | Wavelength |
| --- | --- |
| 1 | 420 |
| 2 | 560 |
| 3 | 860 |
| 4 | 620 |
| 5 | 726 |
| 6 | 800 |
| 7 | 581 |
| 8 | 542 |
| 9 | 578 |
| 10 | 601 |
| 11 | 972 |
| 12 | 532 |
| 13 | 475 |
| 14 | 515 |
| 15 | 940 |
| 16 | 680 |
| 17 | 900 |
| 18 | 1064 |
| 19 | 669 |
| 20 | 780 |
| 21 | 839 |
| 22 | 820 |

To collect the images of data subset 402, the one or more cameras are also configured to acquire a selected number of images having temporal spacing between each image short enough to measure temporal variations in reflected light intensity due to motions of the tissue region that correspond to physiological events or conditions in the patient. In some cases, the data obtained from the multiple time separated images form three-dimensional data arrays, wherein the data arrays have one time and two spatial dimensions. Each pixel in the three-dimensional array can be characterized by a time domain variation in reflected light intensity. This time domain signal has different energies at different frequency components related to blood pressure, heart rate, vascular resistance, nervous stimuli, cardiovascular health, respiration, temperature, and/or blood volume. In certain alternatives, a filter may be used to filter out noise. For example, an 860 nm bandpass filter may be used to filter out light wavelengths that correspond to the predominant wavelength spectrum of the ambient lighting in the room, so that the acquired images correspond to reflected light that originates with the light sources in the probe 408. This can reduce and/or prevent aliasing of ambient light fluctuations, such as the 60 Hz fluctuations present in ambient lighting due to the AC power line frequency.

Figure 4:
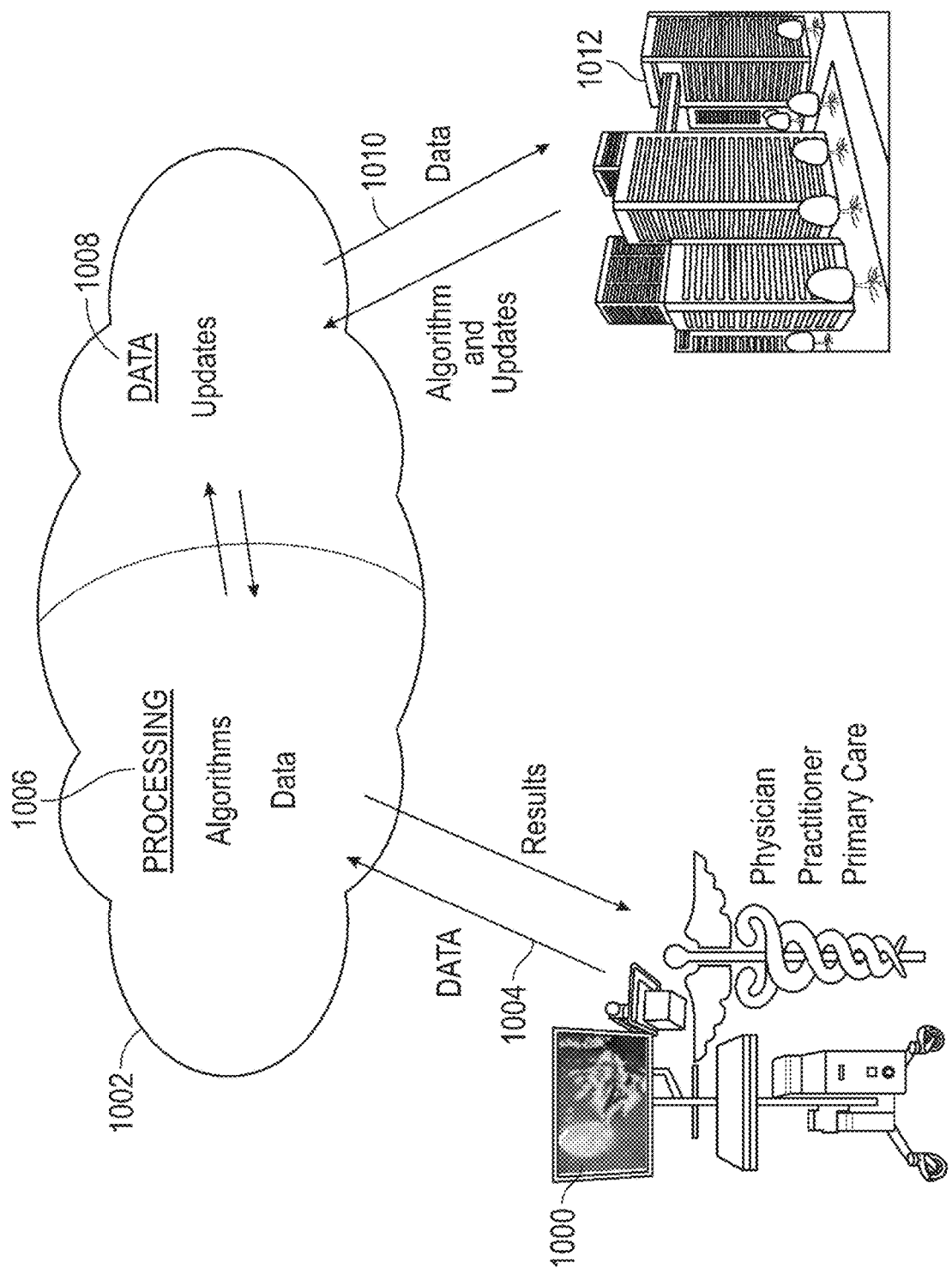
FIG. 4 is an example diagram showing how certain alternatives described herein interact with a remote computing center for data storage and processing (i.e., cloud computing environment).

FIG. 4 shows one example of the dynamic library. In the figure, example imaging device 1000 is connected to example cloud 1002. The example imaging device 1000 may be a device as described herein, or it may be any other computer or user device also connected to the dynamic library. In some cases, the cloud 1002 may comprise of a program execution service (PES) that includes a number of data centers, each data center including one or more physical computing systems configurable to execute one or more virtual desktop instances, each virtual desktop instance associated with a computing environment that includes an operating system configurable to execute one or more applications, each virtual desktop instance accessible by a computing device of a user of the PES via a network. The cloud may also comprise other approaches to synchronize computing and storage.

Data paths 1004 illustrate bi-directional connections between imaging device 1000 and cloud 1002. Cloud 1002 itself has processing components 1006, which is where cloud 1002 receives signals, processes data, performs sorting, and generates metadata, which indicates whether the dynamic library is to be synchronized with one or more computing devices.

In some alternatives, data analysis and classification is performed in the cloud. Such analysis can involve collecting data on sample signals for comparison to obtained signals. Such sampling may be used for generating or refining one or more machine learning models for use in classifying tissue regions in obtained signals, for example using the machine learning techniques described herein. In other alternatives, processing components may be located onboard imaging device 1000 to perform processing locally at data collection sites. Other alternatives can split processing requirements between the cloud and imaging device 1000.

In addition to collecting and analyzing data in a dynamic library, the processing component may also contain general error data and calculations. Errors can be calculated at local sites and aggregated in the cloud and/or be calculated in the cloud. In some circumstances error thresholds for particular classification models can be established. The threshold values consider the consequences for type I and type II errors (e.g., false positives and false negatives), and the standards for clinical reliability.

The processing components 1006 may also perform analysis on the data. Cloud 1002 also has data components 1008, which includes the information in the dynamic library itself, and also receives updates. Data components 1008 and processing components 1006 are coupled to each other.

There may be other sources and repositories also connected to the cloud. In this example, entity 1012 is also connected to cloud 1002. Entity 1012 is an entity that might provide system updates and/or updated tissue classification models to improve system functionality for any device or system, such as system 1000, which is connected to cloud 1002. Through learning and experience, the methods at each stage may be updated to reduce total error. Entity 1012 may quickly assess changes on multiple classification models simultaneously and provide systemic improvements. It may also upload new data sets and models for new clinical applications. In addition, entity 1012 may update system 1000, or any device or system connected to cloud 1002, to acquire data and analyze that data for new therapeutic uses, such as, for example, analyzing frost bite. This expands functionality and allows the system to adapt due to improvements in scientific knowledge.

Additionally, various aspects of alternatives described in this disclosure have been the subject of experiments demonstrating their efficacy in tissue phantoms and animal models. These experiments demonstrated that alternatives of this disclosure may be effective at treating at least amputation sites. The following non-limiting examples are presented for illustrative purposes. The examples provide further details on the experiments performed.

Figure 5B:
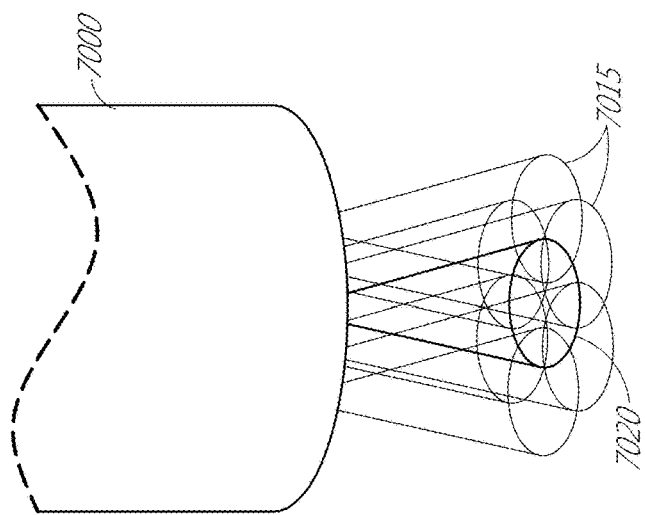
FIGS. 5A, 5B, and 6 illustrate an example fiber optic system that can be used to obtain the image data described herein.
Figure 5A:
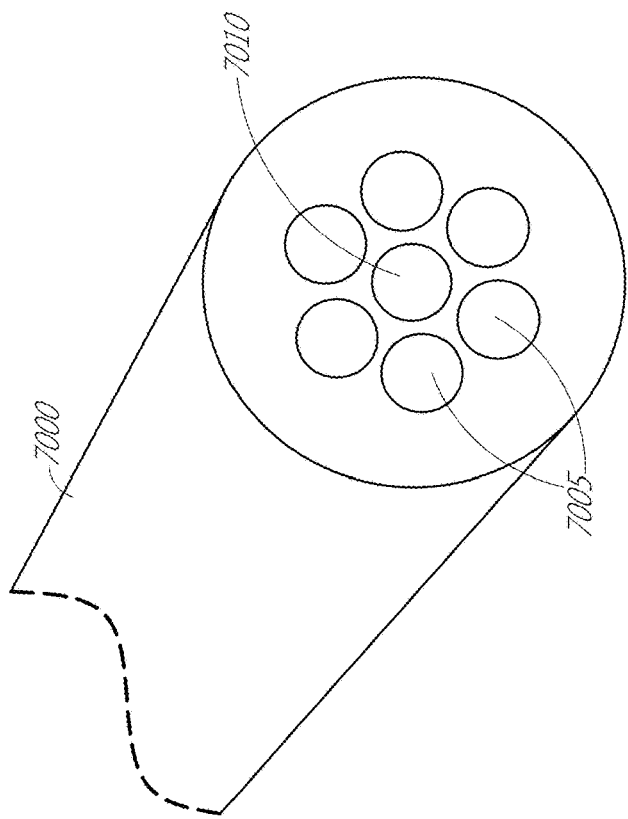
Figure 6:
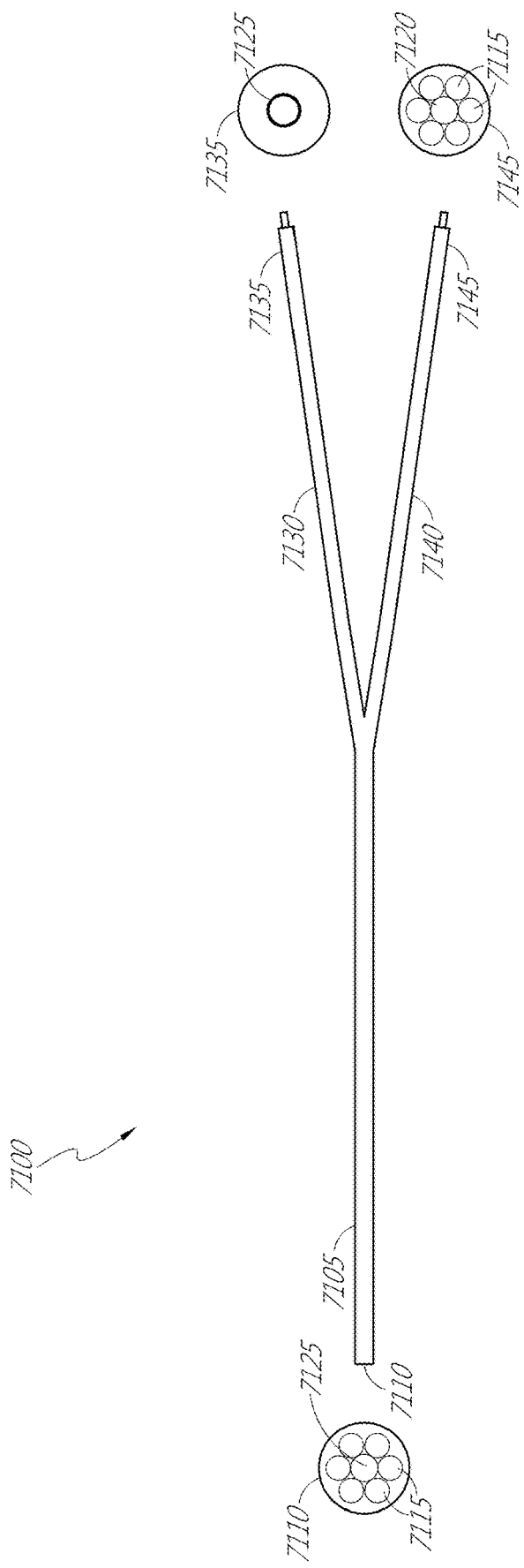

FIGS. 5A, 5B, and 6 illustrate an example fiber optic system that can be used to obtain the image data described herein. As shown in FIG. 5A, a fiber optic probe 7000 can include a number of light emitting fibers 7005 around a light collection fiber 7010. Each of the light emitting fibers 7005 can illuminate one of a plurality of overlapping regions 7015, and the light emitted from the light emitting fibers 7005 can be reflected from the tissue of a subject and collected from an evenly illuminated area 7020 by the light collection fiber 7010. The light emitting fibers can be controlled to sequentially emit one of 1,000 different wavelengths between 400 nm and 1100 nm in some implementations, and signals received by the light collection fiber 7010 can be used to generate images of the illuminated tissue at the emitted wavelengths.

In some embodiments the probe 7000 can be a fiber optic spectrophotometer equipped with a co-axial light source for reflection and backscattering measurements. The probe can be configured for blocking ambient light with a sheath (not illustrated) so that the tissue is imaged using only the emitted wavelengths, leading to more accurate classification than tissue illuminated with both ambient light and select emitted wavelengths.

As shown in FIG. 6, a probe 7100 can include a first cable 7105 having a light emitting and detecting end 7110. The light emitting and detecting end 7110 can include a number of light emitting fibers 7115 around a light collection fiber 7125. The light emitting fibers 7115 can pass through the first cable 7105 and split off into a second cable 7140, a cross-section 7145 of which is shown including the light emitting fibers 7115 around a core 7120. This multi-fiber second cable 7140 can be coupled to a light source for providing the desired wavelengths of light through the second cable 7140 to the light emitting and detecting end 7110 of the first cable 7105. The light detecting fiber 7125 can pass through the first cable 7105 and split off into a third cable 7130, a cross-section 7135 of which is shown including only the light detecting fiber 7125. This single-fiber third cable 7130 can provide signals from the light detecting fiber 7125 to an image sensor configured for capture of image data (for example a CMOS or CCD image sensor) or to a spectrometer. The fiber core size can range from 200-600 µm, such as 200 µm, 250 µm, 300 µm, 350 µm, 400 µm, 450 µm, 500 µm, 550 µm, or 600 µm or within a range defined by any two of the aforementioned wavelengths.

Figure 7:
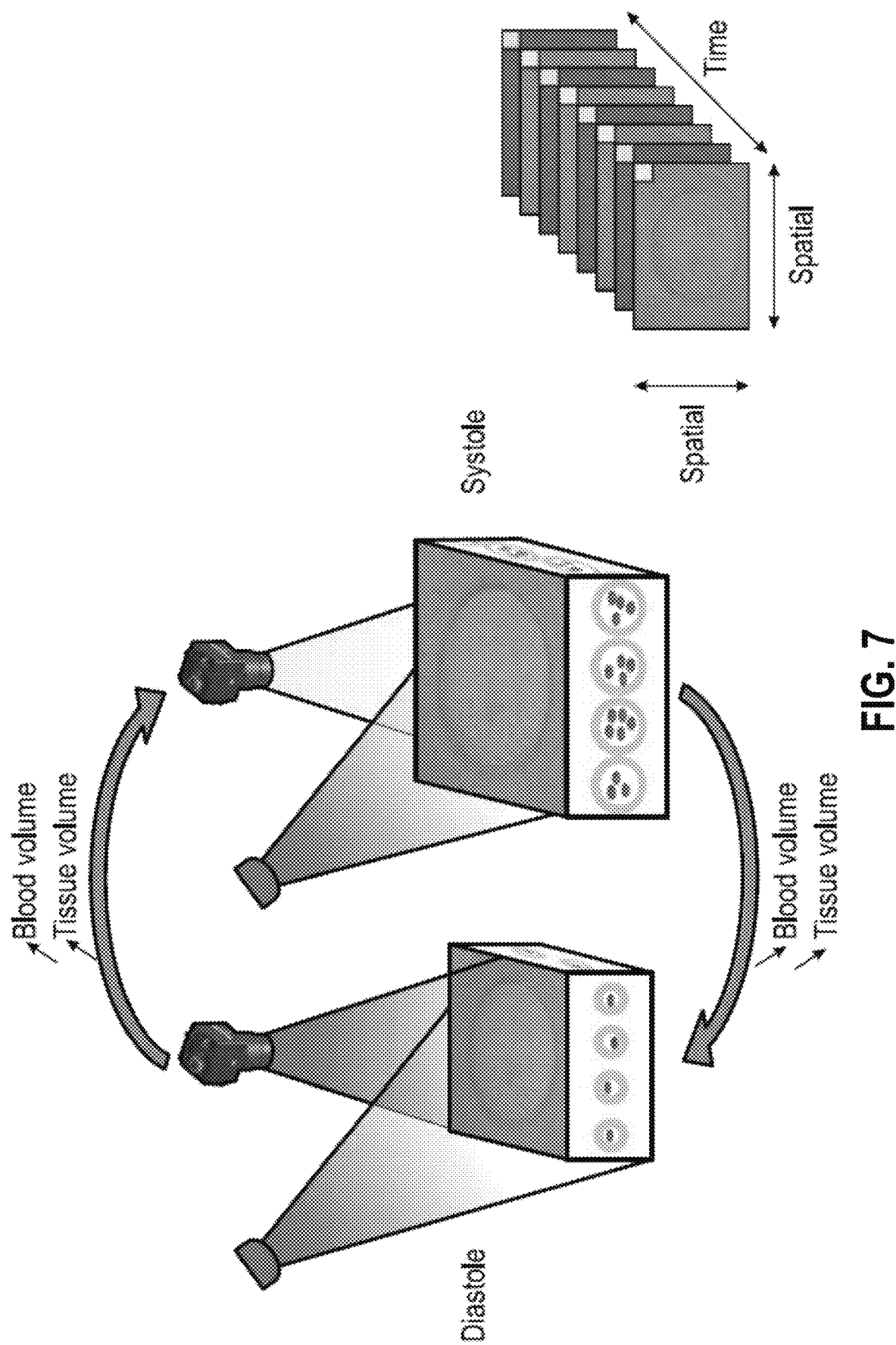
FIG. 7 illustrates components of a reflectance mode and 2-D PPG imaging system (left). Monochromatic light incident on the tissue surface scatters within the tissue as it interacts with molecular structures. A small portion of that light returns to the camera. When measured over time, the intensity changes in the back-scattered light produces a PPG waveform. Each pixel in the raw data cube contains a unique PPG waveform that may be analyzed to generate a single blood flow image of the tissue (right).
Figure 8:
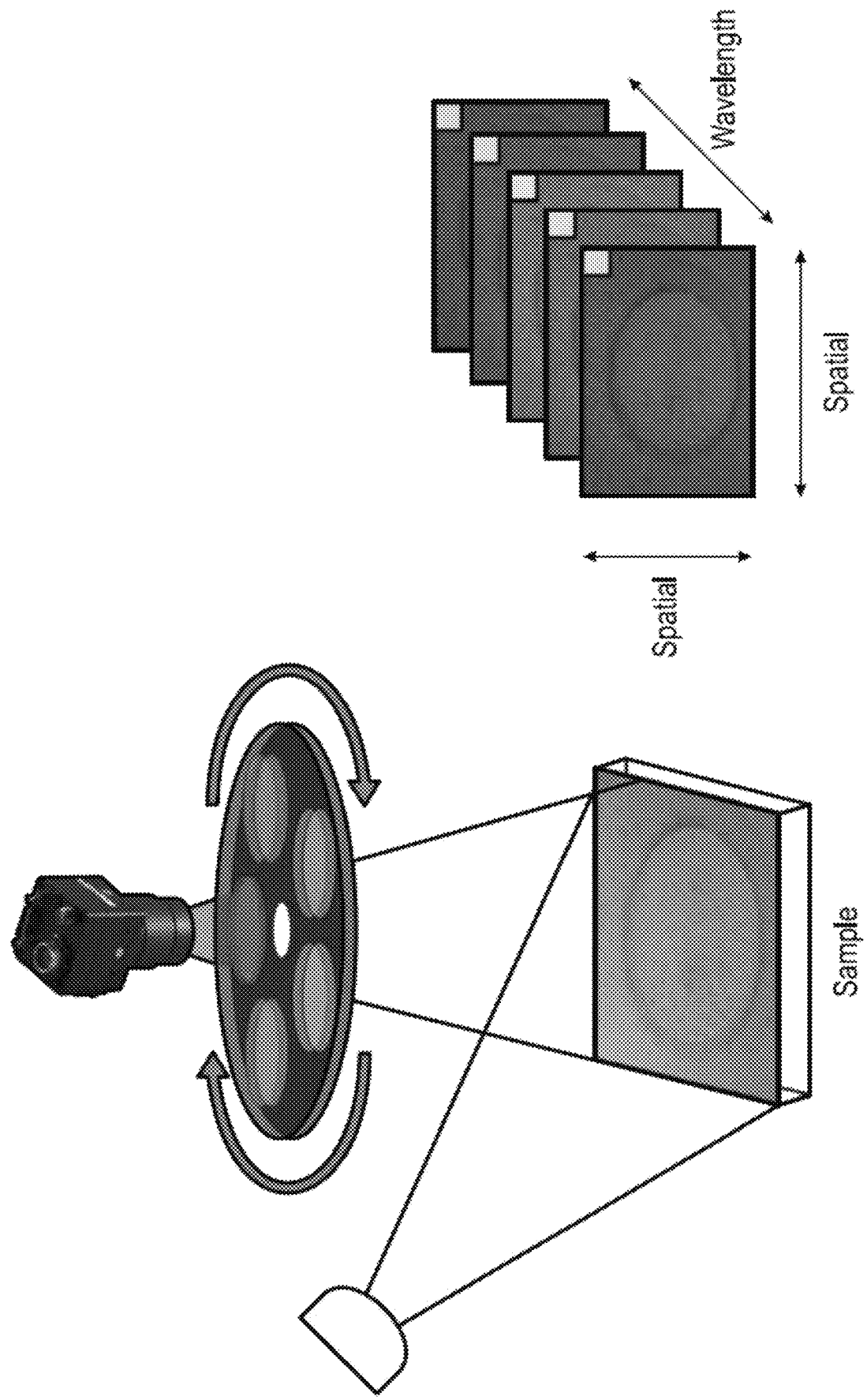
FIG. 8 illustrates components of a multispectral imager including a broad spectrum illumination source, a digital camera, and a rotating filter wheel equipped with various optical filters that isolate predetermined wavelengths of light reflected from the target's surface (left). This system quickly collects an image at each position in the filter wheel to generate a spectral data cube (right). Each pixel in the data cube represents a low spectral-resolution diffuse reflectance spectrum of the tissue.

Example components of an embodiment of a PPG imaging system are illustrated in FIG. 7, and example components of an embodiment of an MSI system are illustrated in FIG. 8. In some alternatives these can be physically separate imaging systems, while in other alternatives these can be integrated into a single, unitary imaging system.

The PPG imaging system can include a 10-bit monochromatic CMOS camera (for example Nocturn XL, Photonis USA), that provides low dark noise and high dynamic range. The 10-bit ADC resolution can offer a signal-to-noise ratio of 60 dB. The resolution of this imager can be set to 1280×1040 (aspect ratio 5:4). The camera can be mounted vertically and facing down to the object surface. A common field of view (FOV) of 20×16 cm can be controlled for inter-system comparison. The exposure time of the camera can be calibrated with a 95% reflectance reference standard (for example, Spectralon SG3151; LabSphere Inc.; North Sutton, N.H.). To illuminate the tissue, four monochromatic and high-power LED emitters (SFH 4740, OSRAM) can be positioned in a 2×2 array mounted in the same plane as the sensor. The LED emitter array can be placed with camera at 15 cm to the target surface. LED emitters can be preferred in some alternatives because they provide an even illumination of the tissue in the camera's FOV (i.e., the spatial intensity variation was less than 15%). The FOV of the camera can be controlled by the optical lens and can be slightly narrower than the illumination area.

The introduction of noise into the PPG signal by the motion of a subject during respiration can make initial analysis of PPG imaging difficult. The disclosed techniques can reduce the influence of respiratory motion using a signal processing method called envelope extraction. To each pixel in the image, the signal can be smoothed with a low pass filter to extract the envelope of the noisy signal. The noisy signal can then be divided by its envelope to remove the dramatic motion spikes in the signal. The remaining clear signal demonstrates information that can then be processed into the PPG image. The PPG image data can be generated based on a number of frames captured during a time interval of at least 10 seconds, preferably between 5 and 30 seconds.

The PPG systems can include three functional modules: illumination; sensor (a CMOS camera); and the imaging target. The illumination and the sensing modules can be placed on the same side relative to the target, for example in a reflective mode. The optical beam incident on the object scatters into the target, then the back-scattered optical signals are captured by the camera. The imaging target buried in the opaque medium varies over time (e.g., a blood vessel changing in volume owing to pulsatile blood flow), causing the back-scattered light to have a modulation in intensity. Differences in signal noise from spatially different tissue regions can be used, in some embodiments, for classification of the tissue regions as healthy tissue, vascularly diseased tissue, necrotic tissue, or other tissue classifications.

As shown in FIG. 8, in some alternatives multispectral images can be collected by the Staring method using a filter-wheel camera (for example, SpectroCam, Pixelteq; Largo, Fla.) equipped with eight unique optical band-pass filters between 400 and 1,100 nm wavelengths. Wavelength filters with the following peak transmission can be used: 581, 420, 620, 860, 601, 680, 669, and/or 972 nm (filter widths can be ±10 nm; for example Ocean Thin Films; Largo, Fla.). Other suitable wavelengths can be used in other alternatives. The system can be calibrated using a 95% square reflectance standard (for example, Spectralon SG3151; LabSphere Inc.; North Sutton, N.H.) in order to compensate for the different spectral response of the imaging sensor. The light source used can be a 250 W Tungsten-Halogen lamp (for example, LowePro) equipped with a frosted glass diffuser to create a more even illumination profile within the imager's field of view. The system of FIG. 8 can use a telescopic lens (for example, Distagon T*2.8/25 ZF-IR; Zeiss Inc.; USA).

In some embodiments, multispectral image data can be acquired using a multispectral image acquisition system designed according to the following parameters. The lighting source and the image capture module were can be placed in a reflective mode at a distance of 60 cm away from the target surface. A tungsten light (for example, ViP Pro-light, Lowel Inc.) can provide a broad spectral projection on the target surface in DC-mode. Frosted glass (for example, iP-50, Lowel Inc.) can be mounted in front of the tungsten light to diffuse the light and increased the uniformity of spatial illumination. Some incident light can penetrate through the target surface, while any back-scattered optical signal can be collected by the image capture module. The image capture module can include a high-performance IR-enhanced optical lens (example model: Distagon T*F-2.8/25 mm, Zeiss), an eight-slot filter wheel, and a 12-bit monochromatic camera (BM-141GE, JAI Inc.). The optical bandpass filters can be designed and selected to isolate a single wavelength of light for the camera. The following eight bandpass filters can be installed in the filterwheel in some embodiments: the center wavelength (CWL) and the full width at half maximum (FWHM) of the eight filters can be (CWL-FWHM, both in nm): 420-20, 542-10, 581-20, 601-13, 726-41, 800-10, 860-20, and/or 972-10. Wavelength intensity can be normalized by using a Reflectance Zenith Lite Panel (for example, SphereOptics GmbH), and the maximum value of a pixel can be 4098 (12 bits). The eight implemented wavelengths can be selected based on known skin tissue absorption behavior at these wavelengths that would allow for accurate tissue differentiation for useful classification. The camera can sequentially captured single wavelength images through each of the eight filters as the filter wheel is rotated Images can be saved on the computer in an uncompressed format. Calculations and statistics were performed using MATLAB® software (version 2014 b) or by a suitable signal processor.

In some embodiments, the light source can be any broad spectrum illumination source, or any illumination source that matches the desired wavelengths of light necessary for data analysis.

Overview of Example Embodiments Wavelength Ranges for MSI

The multispectral images described herein can be captured, in some embodiments, by a fiber optic cable as described herein having both light emitters and a light detector at the same end of a probe. The light emitters can be capable of emitting around 1000 different wavelengths of light between 400 nm and 1100 nm to provide for a smooth range of illumination of the subject at different wavelengths, in contrast to previously-used camera systems that use around eight independent wavelength options. In some embodiments the subject can be sequentially illuminated with each wavelength through a determined range of wavelengths, for example between 400 nm and 500 nm (such as, 400 nm, 425 nm, 450 nm, 475 nm, or 500 nm) and between 720 nm and 1000 nm (such as 720 nm, 750 nm, 775 nm, 800 nm, 825 nm, 850 nm, 875 nm, 900 nm, 925 nm, 950 nm, 975 nm, or 1000 nm), or within a range defined by any wavelength between any two of the aforementioned wavelengths, with one or more images captured of the subject at each wavelength.

Visible and NIR ranges can be significantly different between wound and healthy tissues, and the disclosed classification techniques carry adequate information to differentiate clinically important tissue types. In some embodiments, the highest reflectance values for a number of tissue types may occur at approximately 625 nm. There can be secondary peaks at 525 nm and 575 nm.

In some embodiments, the most different values between the injury and the healthy skin can occur between 475 nm and 525 nm; 450 nm and 500 nm; and 700 nm and 925 nm. Accordingly, for classifying wound tissue compared to healthy skin, a multispectral imaging system as described herein may use wavelengths in in a low end range and a high end rage that are discontinuous, for example between 450 nm and 525 nm and between 700 nm and 925 nm, or within a range defined by any wavelength between any two of the aforementioned wavelengths.

In some embodiments, the most different values between the necrotic or vascularly diseased tissue and the healthy skin can occur between: 400 nm and 450 nm; 525 nm and 580 nm; and 610 nm or 1,050 nm. Accordingly, for classifying wound tissue compared to healthy skin, a multispectral imaging system as described herein may use wavelengths in in a low end range and a high end rage that are discontinuous, for example between 400 nm and 450 nm or 525 nm and 580 nm or between 610 nm and 1,050 nm, or a range defined by any wavelength between any two of the aforementioned wavelengths.

In some embodiments, a multispectral imaging system used for tissue classification can use wavelengths in a low end range and a high end range that are discontinuous, for example between 400 nm and 500 nm or between 720 nm and 1000 nm, or within a range defined by any wavelength between any two of the aforementioned wavelengths. For example, a probe as shown in FIGS. 5A, 5B, and 6 can be configured to emit a number of wavelengths between 400 nm and 500 nm or between 720 nm and 1000 nm, or within a range defined by any wavelength between any two of the aforementioned wavelengths. In some embodiments, such wavelength ranges may be suitable for tissue classification across a range of skin pigmentation similar to those of the patients from whom training data is collected, and a different set of ranges offset from the disclosed ranges can be used for tissue classification of lighter or darker pigmented skin. The different set of ranges can be identified based on separation of the spectrum received from the healthy tissue versus the spectrum received from the tissue of interest (for example, necrotic tissue or vascular diseased bed tissue).

In one embodiment, a set of multispectral images for use in amputation site tissue classification can include eight images captured at different wavelengths. The set of wavelengths can include (listed as center wavelength±full-width at half-max): 420 nm±20 nm, 525 nm±35 nm, 581 nm±20 nm, 620 nm±20 nm, 660 nm±20 nm, 726 nm±41 nm, 820 nm±20 nm, or 855 nm±30 nm or within a range defined by any two of the aforementioned wavelengths.

Overview of Example PPG and/or MSI Image Processing Alternatives

Figure 9:
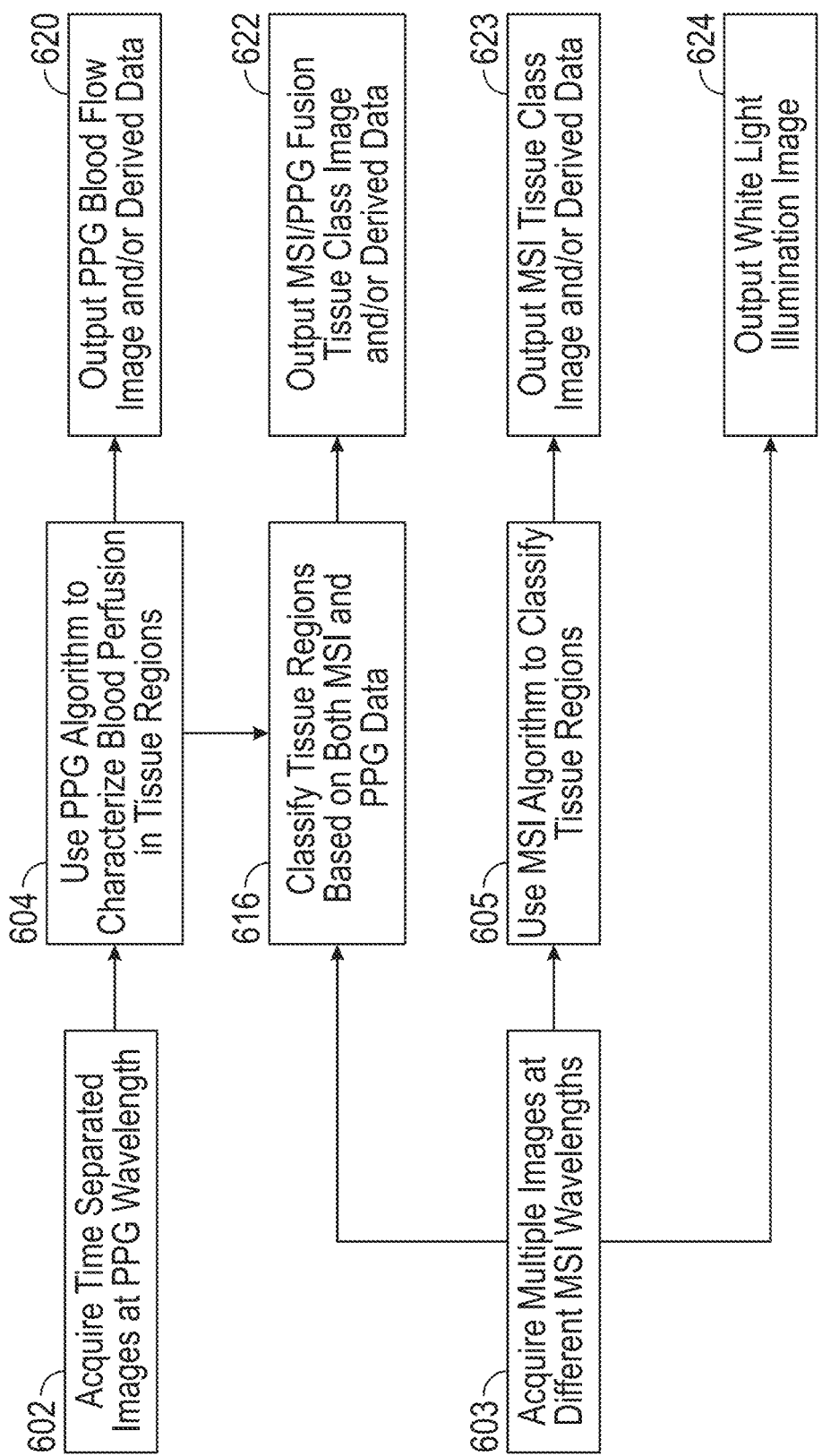
FIG. 9 is an example flow chart showing the steps used for tissue classification in certain alternatives described herein.

Additional detail regarding advantageous image acquisition and signal processing procedures are described with reference to FIG. 9, which illustrates processes that may be performed by the imaging devices described herein. FIG. 9 shows an example flow diagram 600 of the processes used by some alternatives to classify tissue. Blocks 602 and 603 show that some alternatives take multi-spectral images and multiple time separated images (e.g. videos) using, for example, the probe 408. For the time separated images, for example data subset 402, in order to obtain a signal with less overall noise and higher signal-to-noise ratios, it was found that a relatively long exposure time was desirable. In certain cases, a capture time of twenty-seven (27) seconds was used, which is longer than the seven (7) second capture time of conventional PPG imaging processes. Accordingly, capture times of at least, greater than, or any number in between 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds, or within a range defined by a capture time that is between any two of the aforementioned numbers is desired in some alternatives. During these capture times, the number of frames per second captured by the imager may be set. In some circumstances, thirty (30) frames per second (fps) or sixty (60) fps may be effective at imaging tissue. At 30 fps over 27 seconds, the imager takes about 810 images. At 60 fps over 27 seconds, the imager takes about 1620 images. In some alternatives, the number of images taken may vary depending on the resolution of data needed (e.g., to capture the human heart beat). For example, for CMOS cameras, twenty (20) to one hundred twenty (120) fps may be used. This includes sample rates of 20, 30, 40, 50, 60, 70, 80, 90, 100, 110, or 120 fps or within a range of rates defined by a sample rate that is between any two of the aforementioned rates.

Also, in certain alternatives, light source placement was important due to illumination spots, which were locations of light high intensity that saturated the signal and masked pulse waveforms. In some alternatives, this issue was resolved by using diffusers and other front-end hardware techniques. However, in cases where the illumination spots could not be eliminated by front-end techniques, signal processing was used in some alternatives to eliminate the illumination spots. Indeed, to create reliable images of tissue pathologies, the signal is desirably preserved and displayed while the noise is discarded. This process involves removing the noise associated with illumination spots and other irrelevant signals.

At block 604 the time-resolved image sequence (data subset 402 for example) is sent to the controller/classifier/processor 412 for processing, which then uses a PPG analysis to calculate the blood flow perfusion in the tissue area. This process can involve amplification, linearization, signal averaging, correlation, and/or one or more filters (for example, bandpass, highpass, or lowpass) to eliminate noise, isolate the portions of signal of interest, and boost signal-to-noise ratios. The choice of filters is important because too much filtering can cut out essential data while too little filtering can make the signal harder to analyze. Cross-correlation and auto-correlation can also be used to eliminate noise. In some alternatives, sample signals can also be used to eliminate noise, as will be described below. The signal is then transformed into the frequency domain. For example, in some alternatives, a fast Fourier transform (FFT) is used. After performing the FFT, the signal is then analyzable by frequency. The time domain variation of reflected light intensity at each pixel over the course of the multiple time separated images has signal energy at various frequencies. These frequencies, and the physiological events to which they correspond, give an indication of the impact of the occurrence and intensity of those physiological events at the tissue location imaged with the pixel. For example, the signal intensity at a pixel in a band around 1.0 Hz, which is approximately the frequency of a resting human heart beat, can be used to assess the blood flow to and around the tissue at the location of the pixel in the image.

In some alternatives, relevant signals can be identified by looking at local maxima. For example, heart rates were found by looking at the signal energy in the band around the frequency at the highest peak and assuming that the peak was part of due to heartbeat induced blood pressure changes. However, this method may not identify noise that has a peak higher than the signal from the actual heart rate. In such a case, other alternatives utilize signal processing that employs computer learning and training based on examples or on a database of references of noisy signals, white noise signals, and other example signals. The computer analyzes examples of relevant signals and noise to learn to identify the signals over the noise. For example, in the case of identifying signals related to blood flow, signals that have the same frequency content as the heart beat may be relevant. The computer learning utilizes example heart rate signals or refers to a database of heart rate signals as a reference so as to identify the heart rate from the noise. The computer learning process can also analyze white noise, false heart rate signals, and noise signals with peaks higher than a heart rate signal utilizing such reference points and databases. The computer learning can identify the signals based on characteristics such as frequency, amplitude, signal-to-noise ratio, zero crossings, typical shape, or any other characteristic of a signal.

In some circumstances, additional comparisons are utilized to identify signals. For example, in some alternatives, compilations of hand-picked clinical stage signals are created. The hand-picked clinical stage signals are then compared to the measured signals to classify the measured signal as a signal of interest or noise. Another technical advancement that was implemented was the removal of edge effects.

In some alternatives, images showed grainy noise around the edge, and in some instances, regions of interest were also less pronounced than desired. When the edge effects were removed, regions of interest showed higher signal strength. In some alternatives, edge removal was accomplished by using image processing, including averaging, dilation and erosion, and edge detection and enhancement.

Another technical advancement was the automatic removal of motion artifacts. Motion artifacts include motion associated with a patient's breathing, a patient's movements, or any general vibrations around the camera or patient that may skew an image. To remove these motion artifacts, the signal was processed with "windowing", which identifies regions of the time domain that are much larger and noisier than surrounding portions and identifies those regions as "motion." These segments are then clipped out of the time domain, allowing a modified signal without the motion artifact. Other filters and selection methods may also be used to remove noise and otherwise unwanted signal portions. After this processing, the computed signal energy at the desired frequency (e.g. generally about 1 Hz) can be classified for tissue region (e.g. for each two-dimensional pixel position) into categories defining blood perfusion at that pixel position.

At substantially the same time as the performance of blocks 602 and 604, some alternatives also perform blocks 603 and 605. Block 603 acquires the images forming the multi-spectral data cube (data subset 404 of FIG. 3 for example). The data cube comprises 2D images at every MSI spectral band. At block 605, these alternatives then apply MSI analysis to the data, and at block 614, the system assigns a category of tissue composition to each tissue region (e.g. for each two-dimensional pixel position).

Block 616 then combines the blood perfusion and MSI data from blocks 603 and 604 to create tissue classifications based on both MSI and PPG data.

For example, for illustrative purposes, eight bandpass filters may be used to produce eight reflectivity values for each pixel imaged, each one corresponding to a selected spectral band. Also, 810 images may be acquired over 27 seconds at 30 frames per second taken using a filter with center wavelength at an infrared or near infrared wavelength (e.g., near or around or at 840-880 nm, including 840, 850, 860, 870, or 880 nm wavelengths or within a range defined by any wavelength that is between any two of those wavelengths). These 810 images could be analyzed in the frequency domain as described above to produce PPG data characterizing blood perfusion at each spatial location imaged, producing a perfusion value for each pixel imaged. Thus, each pixel of an imaged tissue region would have measurements corresponding to measurements taken with each of the eight bandpass filters and a value corresponding to local blood flow. This is a total of nine (9) measurements at each pixel. Using these 9 measurements, the pixels can be segmented (e.g., categorized) into different categories. As will be appreciated by someone having ordinary skill in the art, any number of measurements (e.g., 2, 10, 20, or within a range defined by any number of measurements that is between any two of those measurements or greater than any one of those measurements), may be taken for each pixel, and the pixels may be segmented by those measurements.

Various segmentation/classification methods could be used. Generally, classifiers are trained using a "training" data set where the measured parameters are known as well as the appropriate classification. The trained classifier is then tested on a "test" data set where also the measured parameters are known as well as the appropriate classification, but which was not used to train the classifier. The classifier quality can be assessed by how well the classifier successfully classifies the test data set. In some alternatives, a predetermined number of categories could be used, and the pixels sorted into those predetermined categories relating to amputation sites as described herein.

In other alternatives, the number of categories is unknown, and the processor, such as processor 112, creates categories based on groupings of pixels and their characteristics relative to each other. For example, the processor could identify a tissue region with much poorer blood flow and much lower normalized pixel intensities at certain wavelengths as being associated with necrotic tissue by virtue of these measurements relative to surrounding measurements.

In some alternatives, the pixels are distributed based on preset ranges of values for each of the categories. For example, certain ranges of values for light reflectance may be associated with healthy skin. When data falls within those ranges, the tissue is identified as healthy skin. These preset ranges may be stored in memory on the system 412, entered by a user, or otherwise determined automatically by system learning or adaptive classifiers. In some alternatives, categories are defined by information transferred to the system by an external source, such as by a data uplink, cloud (as will be discussed later in this disclosure), or any data source. In other alternatives, present ranges of values for each category are unknown and the processor adapts categories based on comparing measurements at each pixel to each other.

In some alternatives, an adaptive classifier may be used to categorize pixels into groups with common characteristics, and identify those groups. For example, graph theory may be used to divide the pixels into categories by finding graph cuts, such as minimum cuts. Other segmentation methods could also be used, such as thresholding, clustering (e.g., k-means, hierarchical clustering, and fuzzy clustering), watershed, edge detection, region growing, statistical grouping, shape recognition, morphological image processing, computer training/computer vision, histogram-based methods, and any segmentation method known in the art of categorizing data into groups.

In some alternatives, historical data may be used to further inform the segmentation. The historical data may include data previously obtained by the patient and/or data from other patients. In certain alternatives, other data, such as skin tone, race, age, weight, gender, and other physiological factors, are considered in the segmentation process. In any case, data may be uploaded, obtained from a cloud, or otherwise inputted in the system, including using UI 114. In certain alternatives, a dynamic library of patient data is analyzed. Statistical methods, including t-tests, f-tests, z-tests, or any other statistical method for comparison, may be used to compare previously identified images to acquired images. Such comparisons, for example, might take into account measured pixel intensities, relative measurements of pixels to other pixels in an image, and pixel distributions.

In certain alternatives, the dynamic library may be updated with exemplary images of tissue conditions, such as amputation sites, to aid in the classification of tissue. In other alternatives, the images may be designated and identified by what tissue conditions they show, and how well they show them. Desirably, a full range of images at different angles should be in the dynamic library in order to account for the variations in the angles, quality, and conditions of the skin conditions imaged.

Turning back to FIG. 9, a variety of data outputs may be presented to the user. These include a PPG perfusion image 620 based on the PPG data, an MSI classification image based on the MSI data, a white light illumination image based on normal RGB data, and a MSI/PPG fusion image 622 which illustrates classification based on the combined MSI and PPG data. For example, the display outputs could be combined MSI/PPG fusion classification images 622. In such images, each tissue region (e.g. pixel) of the subject is classified into amputation site classification such as healthy, hyperemia, necrotic, potential amputation skin flap, and vascularly diseased as described above. Additionally or alternatively, data outputs such as percentage in each category could be presented to the user.

The use of both the composition and viability data in classifying tissue is a significant advancement over the prior art.

Figure 10:
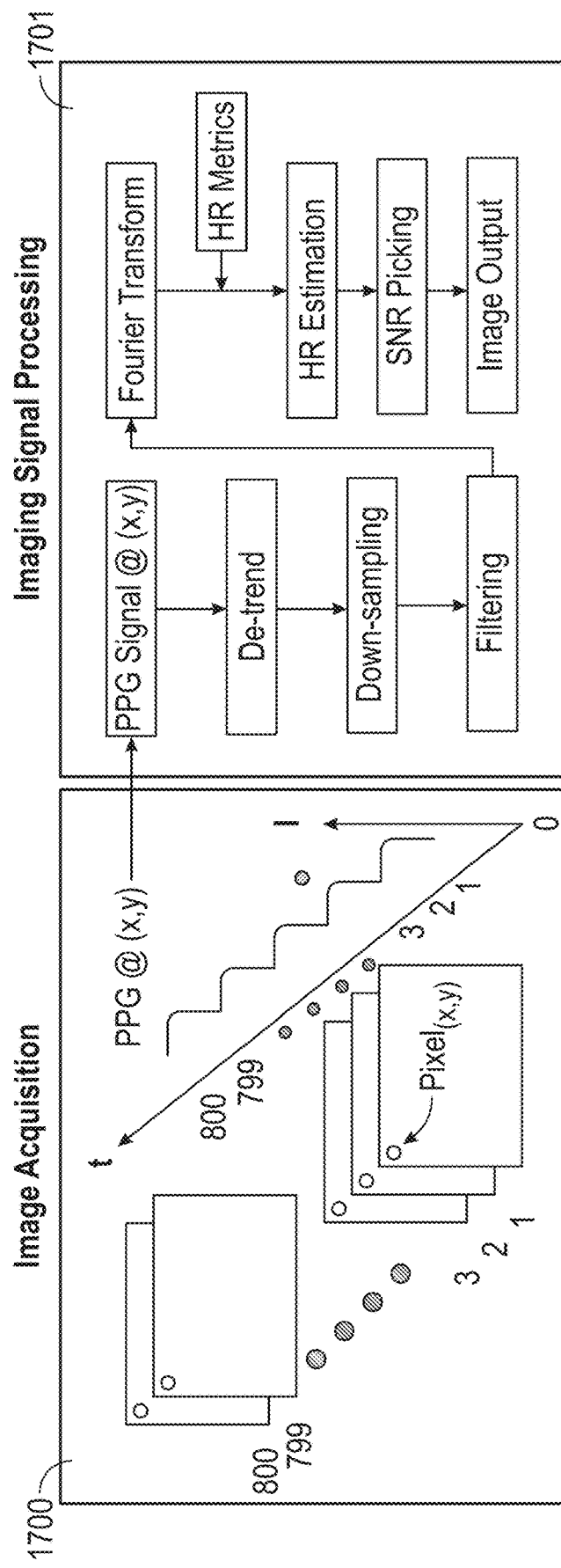
FIG. 10 illustrates a time-resolved PPG signal extraction.

FIG. 10 illustrates an example time-resolved PPG signal extraction. Diagram 1700 shows intensity at image pixel (x, y) extracted sequentially from 800 contingent frames. Diagram 1701 shows a processing method for quantifying PPG signals.

In one example, a sequence of 800 images at a frame rate of 30 frames-per-second can be and stored as uncompressed TIFF files. The PPG signal intensity can be calculated on a pixel-by-pixel basis. The steps for PPG signal and image processing can be as follows: (1) de-trending, which removes the DC wandering; (2) down-sampling in time-domain to reduce the data volume; (3) filtering of the signal; (4) fast Fourier transformation (FFT) converting time-resolved signal to frequency-domain; (5) extracting the spectral power, particularly at the frequency equivalent to the heart rate; (6) calculating the ratio of the summation of intensity in heart rate band to the summation of the intensity in higher frequency band or non-target frequency band (regarded as noise) calculated as the signal-to-noise ratio (SNR); (7) PPG image outputs use a color map to represent each pixel's PPG SNR. The colors are mapped linearly from lowest signal present to highest signal preset within a single image. Signal processing can be conducted with MATLAB or by a specialized signal processor.

Figure 11:
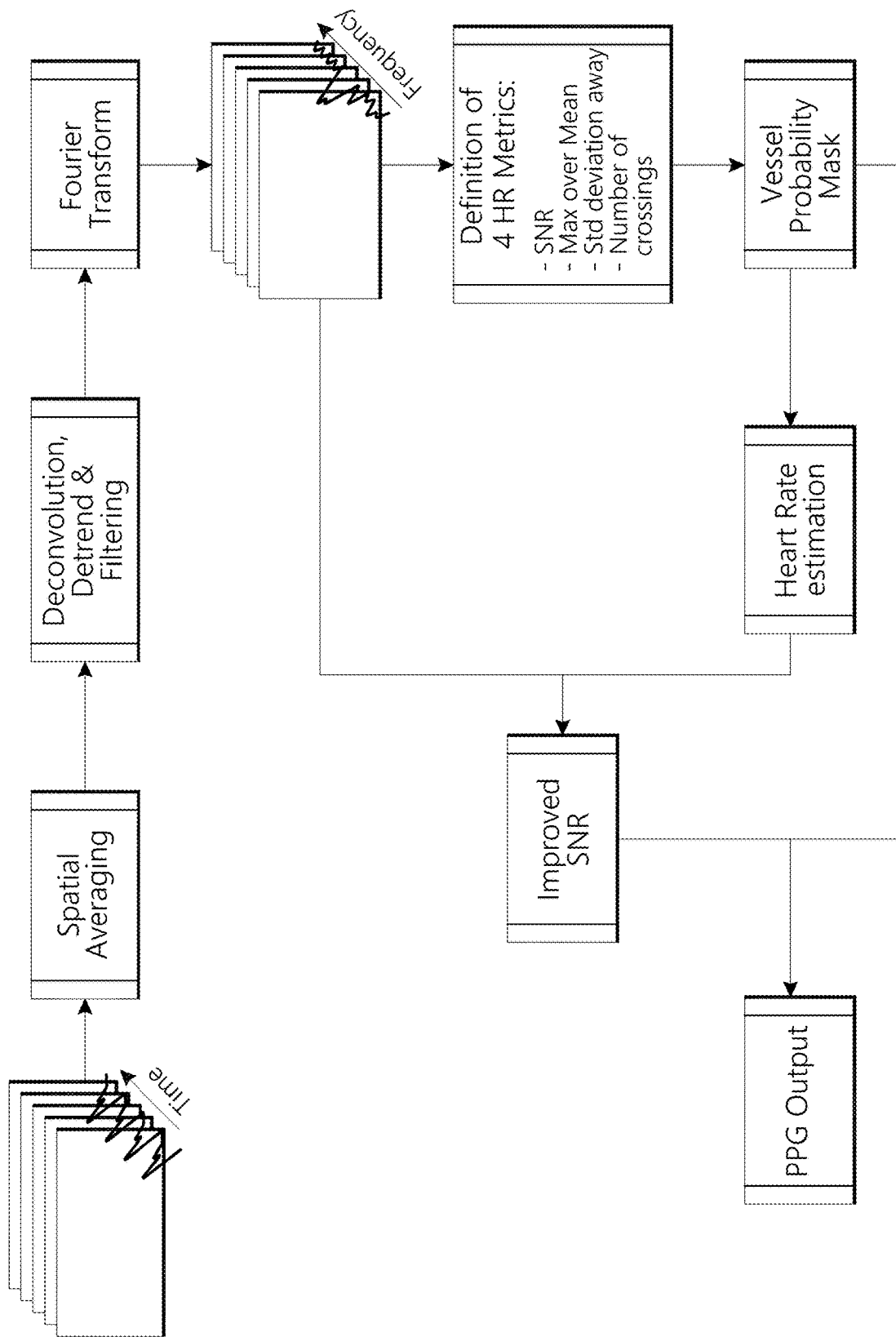
FIG. 11 illustrates an example block diagram of PPG output preprocessing.

FIG. 11 illustrates an example block diagram of PPG output preprocessing. PPG images are created according to 800 frames from a 27 second video of the amputation site are collected for each image. A PPG signal in time is defined for each pixel. The purpose of this pre-processing is to obtain some physiological information related to the heart rate of the subject, as well as some initial features for the classification step. From this time domain signal (one for each pixel), pre-processing is carried out, which is schematized in FIG. 11 and summarized as follows.

An initial spatial averaging is computed; then, a deconvolution is performed in which the high amplitude component at low frequency—corresponding to the artificial ventilation of the sedated subject—is removed. A linear detrend of the signal, as well as a band pass filtering over the range of frequencies where the heart rate is expected, is performed. A fast Fourier transform is applied to the time domain signal of each pixel in order to compute the frequency domain version.

In some embodiments, for each pixel, four metrics are obtained from these sets of frequency signals: (1) signal-to-noise ratio (SNR), (2) max-over-mean, (3) number of standard deviations away from the mean, and (4) number of times the signal crosses a threshold level. These four metrics are used for establishing a vessel probability in each pixel of the image. The vessel probability indicates how useful a pixel is for providing information about heart rate. For those pixels whose vessel probability is >0.9, the values of the heart rate corresponding to the maximum of the frequency signal are stored. The most repeated value is selected as the true heart rate of the subject for the current step. From this value, an improved SNR metric is calculated. Finally, a mask is defined setting to one (1) those pixels whose heart rate corresponds with the calculated rate, and setting a value between 0-1 to the rest of pixels, depending on their degree of difference from the true heart rate. The PPG Output metric is the result of the product between the improved SNR and that mask.

All these six (6) metrics give physiological information about the blood flow approximately 0.5 cm below the surface of the body of the subject under study for each pixel of the image.

These selected pixels can be extracted and individually processed to determine the strength of the PPG signal at the indicative points. The metric used for evaluating the strength of the PPG signal can be power spectral density (PSD), a measure of the distribution of signal power across frequencies. The power spectral density at the pulsatile frequency provide a clear logarithmic trend for which the intensity of PPG signal received constantly increases across the intensity values.

Overview of Example Amputation Site Analysis Alternatives

The above-described lack of a sufficiently accurate metric/test to determine healing potential and the multiple factors that are known to affect the body's wound healing capacity means that a multivariate approach to diagnosis is required for improved assessment. The disclosed technology is uniquely positioned to address this problem, because the disclosed devices are designed to handle information in the form of multiple independent variables to classify tissue pathological processes. The disclosed imaging devices can use machine learning to combine two optical imaging techniques, photoplethysmography imaging (PPG Imaging) and multispectral imaging (MSI), with patient health metrics, such as diabetic control or smoking, to generate prognostic information (FIG. 12).

Figure 12:
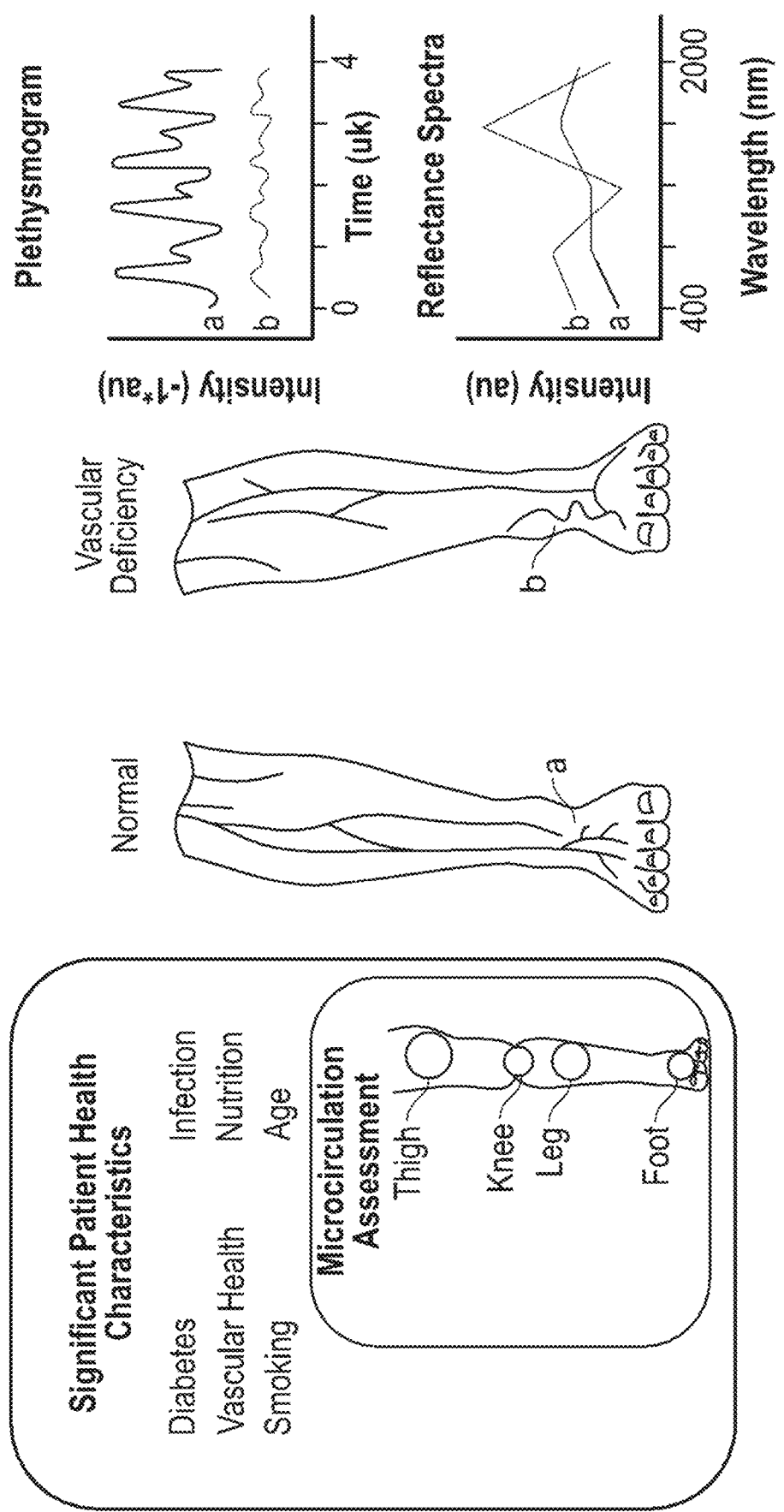
FIG. 12 illustrates a high-level graphical overview of two optical imaging techniques, photoplethysmography imaging (PPG Imaging) and multispectral imaging (MSI) that can be combined with patient health metrics to generate prognostic information according to the present disclosure.

FIG. 12 illustrates a high-level graphical overview of two optical imaging techniques, photoplethysmography imaging (PPG Imaging) and multispectral imaging (MSI) that can be combined with patient health metrics to generate prognostic information according to the present disclosure. The disclosed systems can implement these techniques for classifying patient tissue using any of the imaging technology described herein. The combination of MSI and PPG image data can maintain the high sensitivity and specificity necessary to select appropriate LOA in patients with dysvascular disease. The two optical imaging methods are designed to infer important tissue characteristics, including arterial perfusion and tissue oxygenation. These two measures are key to selecting LOA, because wound healing in patients with peripheral arterial disease (PAD) is hampered by a critical lack of arterial perfusion, resulting in low tissue oxygenation. The disclosed methods can assess perfusion at the tissue level over large areas of the leg simultaneously to identify under-perfused regions of the limb. This is in contrast to the guess work that is involved when using clinical judgment alone, during which the observer must assess for the proper LOA based on patient history and physical examination combined with vascular studies that rarely include a thorough evaluation of the patient's microcirculation. Meanwhile, the disclosed technology also assesses patient health metrics that have systemic effects on wound healing potential. By combining a local assessment of tissue microcirculation with a global assessment of systemic factors affecting wound healing, the disclosed technology accounts for the plurality of factors affecting wound healing rather than a single variable.

An amputation site analysis system as described herein can use a statistical discipline called machine learning to study multi-variate systems for predictive analysis in an applicable manner. This approach can provide key information to the patient's overall likelihood of primary wound healing by incorporating data from local microcirculatory assessment with systemic factors affecting wound healing (such as diabetes mellitus, smoking status, age, and nutritional status) that cannot be readily observed in the microcirculation with current technology. Because both local and systemic factors affect the ultimate likelihood of healing, the amputation site analysis system accuracy can be improved by considering all of these factors together.

An amputation site analysis system can have at least 95% sensitivity and 95% specificity for predicting likelihood of primary wound healing after amputation at the investigated level. If used for routine assessment of patients prior to amputation at this sensitivity and specificity, an amputation site analysis system as described herein can reduce the rate of re-amputation by 67%, resulting in 10,000 fewer re-amputations per year while improving quality of life for amputees and reducing health costs associated with their care. Currently, an ABI exam prior to amputation costs Medicare approximately $150 per patient, and most of the cost incurred is from the technician's time in performing the exam and the practitioner's time in interpreting the results. The proposed device will have no impact on the current cost of LOA assessment, because it is expected to cost the same as current vascular assessments. Unlike some current LOA tests, the disclosed imaging system does not require disposables. Its routine cleaning and servicing costs are similar to those of systems currently on the market.

Figure 13:
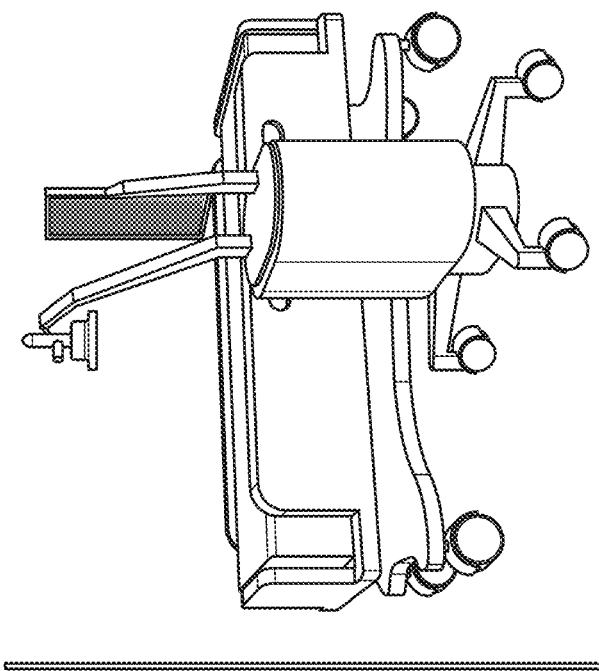
FIG. 13 illustrates example views of an apparatus designed to fuse the optical imaging techniques of photoplethysmography imaging (PPG imaging) and multispectral imaging (MSI).
Figure 13:
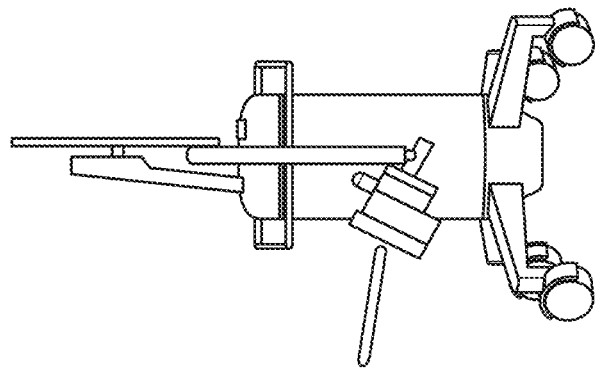
Figure 13:
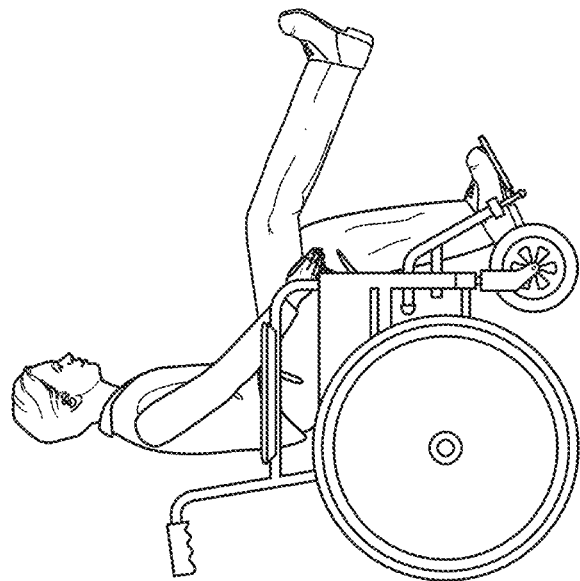

The disclosed imaging technology is designed to fuse the optical imaging techniques of photoplethysmography imaging (PPG imaging) and multispectral imaging (MSI). FIG. 13 illustrates example views of an apparatus designed to fuse the optical imaging techniques of photoplethysmography imaging (PPG imaging) and multispectral imaging (MSI). Moreover, it is capable of incorporating key patient health metrics into its assessment classifier. The disclosed technology is now capable of combining blood flow assessment (e.g., arterial pulse amplitude) with tissue characterization (e.g., spectral analysis). When these measurements are taken from the tissue together, they provide a more accurate assessment of the tissue than does either measurement alone.

Studies to determine likelihood of healing at a certain LOA have demonstrated marked differences in tissue oxygen levels between sites resulting in successful vs. unsuccessful amputations. These studies investigated tissue oxygenation using transcutaneous oxygenation measurement (TCOM). However, the use of TCOM has not surpassed clinical assessment despite the availability of this technology for decades, and no clear cutoff for tissue oxygenation at a given LOA that is prognostic for successful amputation has been determined in a large clinical trial. According to the assessment of experts, TCOM has not been adopted into clinical practice for several reasons. First of all, TCOM collects data from a very small area of interest (approximately 3 cm by 3 cm). The TCOM procedure also requires heating of the patient's skin, which can occasionally lead to skin burns, particularly in patients with PAD. For example, TCOM procedures require placement of adhesive electrodes that heat patient skin to 45° C., occasionally causing skin burns, particularly in patients with PAD. In addition, no clear cutoff for a TCOM level that is prognostic of successful amputation has been determined in a large clinical trial. Finally, results of TCOM are subject to variations in ambient temperature and localized tissue edema, limiting the intratemporal consistency of the device.

The amputation site analysis system has been designed to overcome the various limitations of TCOM and other available devices to prognosticate likelihood of healing at a selected LOA. The device captures data across a large tissue surface area, allowing the characterization and mapping of tissue oxygenation and perfusion variability across the entire surface rather than in an isolated area. The amputation site analysis system is non-invasive and non-contact and does not emit harmful radiation, so no major risk of patient harm is inherent to the device. The device is also not affected by minor variations in ambient temperature. Most importantly, however, the amputation site analysis system analyzes clinically significant patient health metrics such as diabetes mellitus history, presence of infection, smoking status, and nutritional status to provide the end-user with a comprehensive assessment of wound healing potential, whereas previous technologies have only been able to assess local tissue oxygenation.

Aspects of the proposed imaging device encompass non-invasive, non-contact, non-radiation optical imaging for a variety of tissue classification applications, including classification of tissue types at a pre-operative and/or post-operative amputation site, as well as identification of a recommended optimal LOA. The disclosed imaging system is a point of care perfusion imaging system that provides diagnostic images derived from measurements of tissue perfusion and patient health metrics. Nursing staff can be easily trained to perform the imaging test. The imaging of a limb takes approximately 10 minutes, with results stored electronically for physician review. From the patient's perspective, the test is highly acceptable because it has no harmful side effects, does not contact their skin, and causes no discomfort.

One aspect of the disclosed technology is the addition of patient health metrics to microcirculation assessment to improve the accuracy of diagnosing wound healing potential during amputation planning. As stated previously, the amputation site analysis device simultaneously performs two optical imaging methods of blood-flow assessment. The first of these, PPG imaging, is the same technology used in pulse oximetry to capture vital signs including heart rate, respiratory rate, and $SpO_2$, though the disclosed amputation site imaging devices are more advanced, because they can capture over 1 million spatially unique PPG signals across a large area of tissue. The PPG signal is generated by measuring light's interaction with dynamic changes in the vascularized tissues. Vascularized tissue expands and contracts in volume by approximately 1-2% with each incoming systolic blood pressure wave at the frequency of the cardiac cycle. This influx of blood increases the volume of the tissue and brings additional hemoglobin proteins that strongly absorb light. Therefore, the total absorbance of light within the tissue oscillates with each heartbeat. This information can be translated into the vital signs reported by pulse oximeters.

In order to generate images from the plethysmogram, the disclosed systems can take advantage of light's pathway through the tissues. A small portion of light incident on the tissue surface scatters into the tissue. A fraction of this scattered light exits the tissue from the same surface it initially entered. Using a sensitive digital camera, this backscattered light is collected across an area of tissue so that each pixel in the imager contains a unique PPG waveform determined by changes in intensity of the scattered light. To generate a 2-D visual map of relative tissue blood flow, the amplitude of each unique waveform is measured. To improve accuracy, the disclosed systems can measure the average amplitude over many heart beat samples.

The second optical measurement captured by the amputation site analysis system is MSI. This technique measures the reflectance of select wavelengths of visible and near-infrared (NIR) light (400-1,100 nm) from a tissue's surface. Spectral characterization of substances is primarily used in remote sensing (e.g., satellite or in-flight imaging) for geological exploration or the detection of military targets, but this technology is gaining ground in medical applications. This method is effective for quantifying key skin properties relevant to several pathologies, including PAD. Relevant to selecting LOA, MSI data can be used quantify the volume fraction of hemoglobin and the presence of oxygenated hemoglobin.

The wavelengths of light employed by MSI in the amputation site analysis system can be selected based on well-established characterizations of light-tissue interaction. Melanin within the stratum corneum and the epidermis mainly absorbs UV and visible wavelengths. Near infrared wavelengths (700-5000 nm) are the least absorbed by melanin and have been found to be the best at penetrating through the dermis. Hemoglobin is largely contained by vessels coursing through the dermis, and its concentration determines the degree of dermal absorption of wavelengths greater than 320 nm. Hemoglobin absorption of light also changes depending on whether the molecule is oxygenated or deoxygenated. As tissue melanin and hemoglobin concentration, as well as the oxygenated hemoglobin fraction, are altered during disease states, MSI detects changes in the resulting reflectance spectrum. Therefore, abnormal skin tissue can be identified by changes in its reflectance spectrum as compared to healthy tissue. Although MSI may use a lower number of unique wavelengths to describe the tissue as compared to newer hyperspectral imagers, MSI remains superior when the combination of spatial resolution, spectral range, image acquisition speed, and cost are considered together.

The third component of data utilized by the amputation site analysis system is the relevant patient health metrics collected during routine patient assessment. A variety of factors that affect wound healing have been identified. Many or all of these factors (including patient age, diagnosis of diabetes mellitus, history of smoking, infections, obesity, medications, nutritional status) commonly affect patients with PAD subjected to lower limb amputations. Although clinicians currently consider a gestalt of these variables when assessing potential LOA, the amputation site analysis system is capable of assessing these metrics quantitatively to predict likelihood of primary wound healing at a given LOA. The integration of patient health metrics with optical imaging data is performed by the amputation site analysis system with its machine learning tissue classification techniques. A practitioner can input relevant patient health metrics into the device at the time of imaging. In some embodiments, input of the patient health metrics can be authorized by a patient and/or physician and then such metrics can be automatically provided from a hospital information database or an electronic patient medical record. In some implementations this data can be treated as additional variable(s) by the disclosed machine learning model, no different than the optical data collected by PPG imaging and MSI. In other implementations the machine learning model can use the patient metrics to identify a specific tissue classifier suitable for classifying the patient's tissue, for example from a number of different classifiers trained from different data sets. The machine learning model can be trained to generate a quantitative output after assessing all data collected by the amputation site analysis system. The quantitative output can be translated into an image identifying areas of the scanned tissue surface that are likely or unlikely to heal following amputation, to generate a mapping of various regions of tissue classifications, and/or to recommend a LOA.

Figure 14:
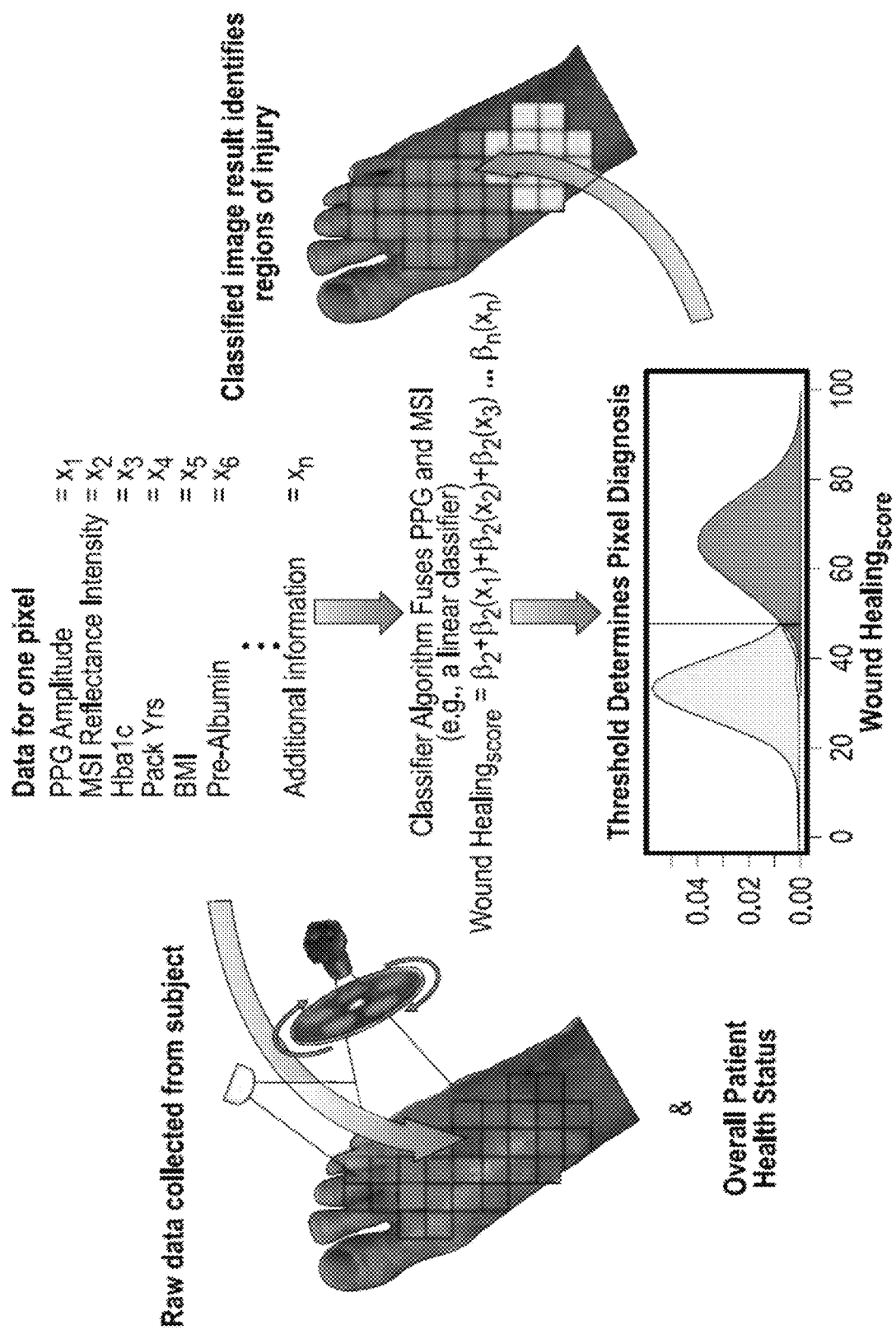
FIG. 14 illustrates an example of a combination of a PPG imager, an MSI camera, and objective patient health metric inputs.

The amputation site analysis system can include a combination of a PPG imager, an MSI camera, and objective patient health metric inputs, as illustrated in FIG. 14. By adjusting system settings and classifier parameters, the amputation site analysis system can be tuned to assess tissue characteristics under different pathological conditions. For LOA studies, the disclosed technology can have developed specific classifiers and use specific optics and filters that are tailored to measures of pulse amplitude and tissue oxygenation for prediction of wound healing following primary amputation as described in more detail below.

Figure 15A:
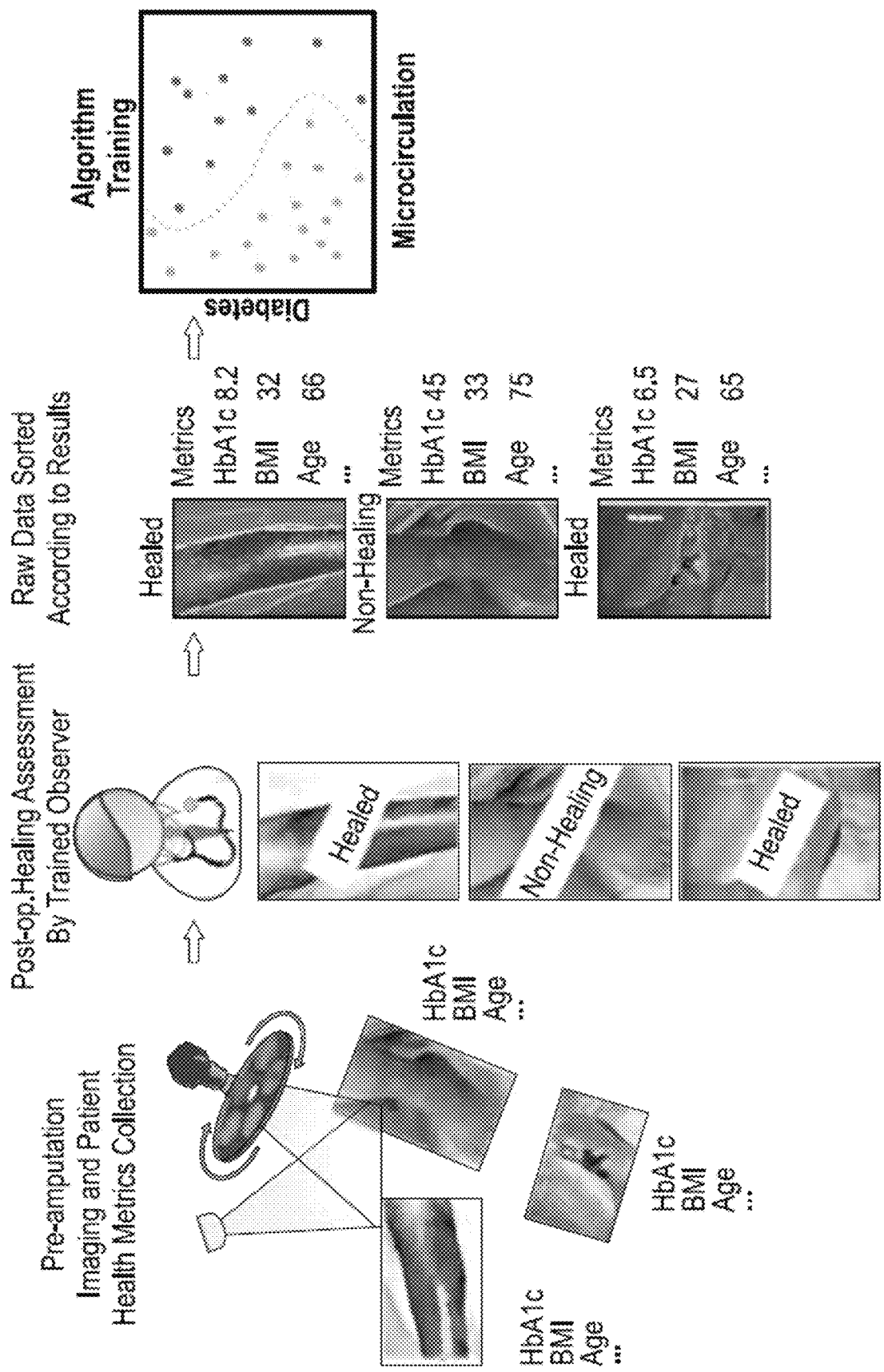
FIGS. 15A and 15B, and 15C illustrate example processes for training a machine learning diagnostic tool and generating a classifier model for a level of amputation.

FIG. 15A illustrates an example process for training a machine learning diagnostic model. Training a diagnostic classifier using a machine learning model can be done using data from the population on which it will eventually be used (FIG. 15A). The accuracy of the classifier can only be as accurate as the methods used to identify the true status of the training data, in this case the non-healing vs. healing amputation groups. To address this, the disclosed methods generated a standardized amputation healing assessment system to track and classify outcomes. The classifier development iterates from an initial determination of accuracy, conducting research to improve accuracy, and then assessing the new accuracy. This provides evidence showing that combining the microcirculation imaging (PPG and MSI) with patient health metrics can accurately classify patient tissue at an amputation site. Although certain disclosed embodiments are described as using both PPG and MSI data together, other embodiments can successfully use MSI features without PPG features to achieve suitable classification accuracies.

The pilot clinical study design included a 60-patient study investigating the disclosed system's accuracy of predicting primary healing in amputations on patients with PAD compared to the current standard of care.

The disclosed imager collected spectral and PPG signals from a large area (up to 15×20 cm of tissue) of the cutaneous blood supply using optical methods. This instrument is well suited to study large regions of the lower extremity skin microcirculation. A unique aspect of the device is that it is capable of integrating important patient health characteristic into its diagnostic classifier to increase accuracy. The pilot study has identified the promising patient health metrics and confirmed patient that health metrics included in the device's machine learning diagnostic classifier improve accuracy over the microcirculation measurements alone. The disclosed technology can determine the microcirculation at each traditional LOA combined with patient health characteristics affecting wound healing and determine how this correlates to the patient's primary wound healing potential after amputation.

The lower limb to be amputated of every patient was be examined and included in the study. Clinically relevant patient health information was be gathered by the facility's care providers. Measurements taken with the disclosed imaging device were carried out by hospital staff previously trained to perform the imaging tests.

The region of skin used for covering the stump of an amputation was graded for positive or negative healing capability with the LOA tissue classifier. The technician performing the amputation site analysis was blinded to the results of the clinical decision as to where the amputation will be performed.

To obtain true positive (+) and true negative (−) events, or non-healing and healing subjects, the disclosed techniques used a standardized primary wound healing after amputation assessment (table 2). This assessment included three categories including: successful amputation; successful amputation with prolonged healing; and failure to heal. Successful amputation is considered healing within 30 days with completed granulation and no need for additional amputation. Successful amputation with prolonged healing is considered delayed healing with granulation incomplete at 30 days, but with eventual healing within six months and no need for re-amputation to a more proximal level. Lastly, failure to heal will be characterized by development of necrosis and/or gangrene, and/or the need for re-amputation to a more proximal level. Additionally, the disclosed techniques can consider a wound requiring revascularization to heal as a failed amputation.

TABLE 2

Standardized Wound Healing Assessment

| Event | Category | Characteristics |
| --- | --- | --- |
| Negative (−) | Healing | Healing within 30 days with completed granulation and no need for additional amputation |
| | Delayed Healing | Incomplete healing with granulation at 30 days, but with eventual healing within six months and no need for re-amputation to a more proximal level |
| Positive (+) | Non-healing | Development of necrosis and/or gangrene, and/or the need for re-amputation to a more proximal level |

These healing assessments took place 30 days post operatively. For the subjects with delayed healing, the disclosed techniques can make a second healing assessment at six months following surgery. Subjects that not healed at six months and have not had a more proximal re-amputation were categorized to the non-healing group.

Figure 15B:
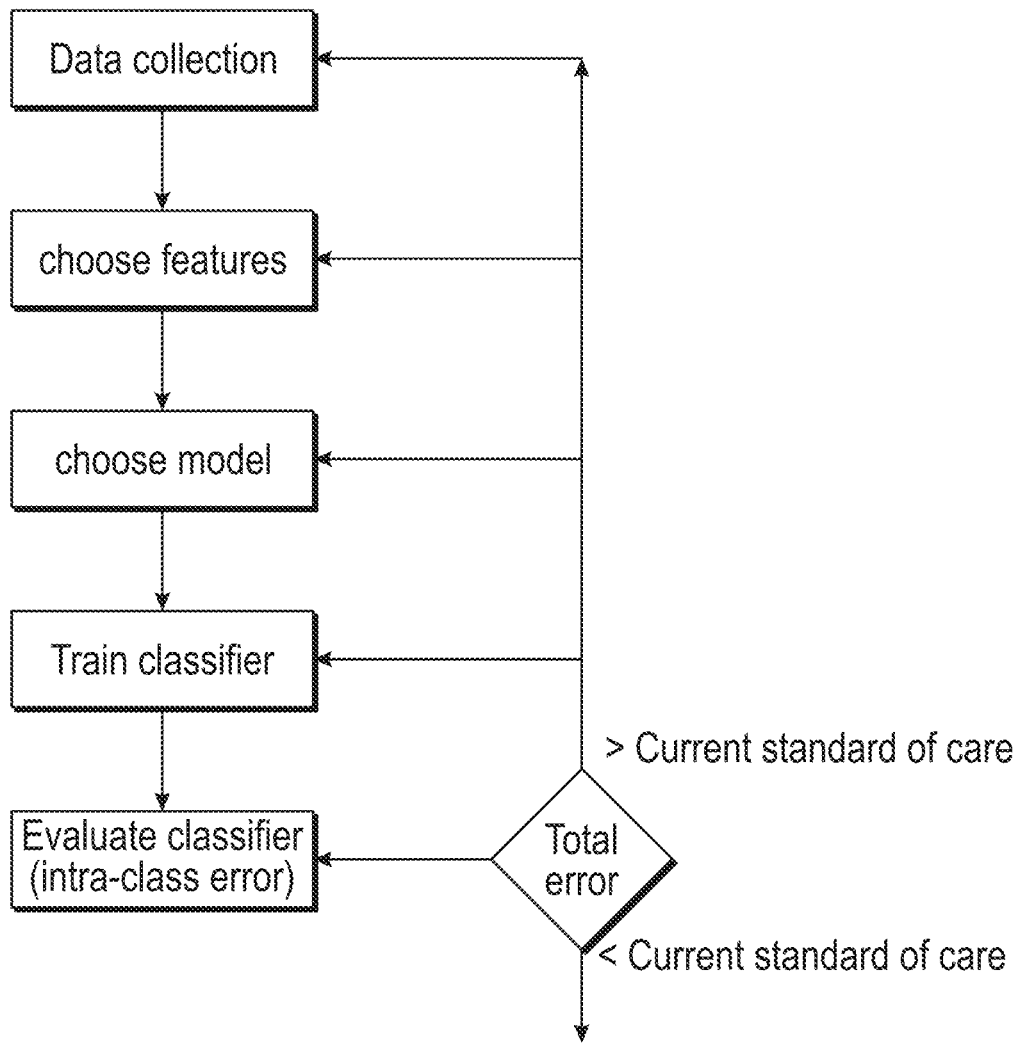

FIG. 15B illustrates example steps in generating a classifier model for a level of amputation. After the initial accuracy is established, the classifier can be developed with a standard set of methodologies for improving accuracy (FIG. 15B). One aspect of this process is addressing the bias-variance trade-off that comes with large models. In other words, the classifier may fit very well to the data in the current study cohort, but not transfer to the general population. In order to address this, the disclosed techniques can conduct feature selection to establish a combination of microcirculatory measurements and patient health data with a high accuracy but a minimum redundancy between variables (e.g., eliminate information from the model with co-variance). A range of classifier models can be implemented for sorting the data, including but not limited to linear and quadratic discriminant analyses, decision trees, clustering, and neural networks, and convolutional neural newtorks.

The disclosed techniques can predict primary healing of an amputation at a rate comparable to the current standard of care (70-90%), and increases in this accuracy can be achieved in a larger clinical study.

Revascularization procedures are sometimes performed with amputation surgery, and this additional procedure may influence the results of the diagnosis. These cases were recorded and considered in the statistical analysis to identify whether there is any interaction between these procedures and the outcome of the diagnostic decision. Another potential issue is in combining the delayed healing group with the healing group in the dichotomous device output. There can be significant differences in the delayed healing population and the healing population that can be included as a separate category in the diagnostic output. Conversely, the delayed healing group may have data that more closely agrees with the non-healing group, and they cannot be separated easily. In this case the disclosed techniques can include the data from more proximal images into the classifier. The clinical utility of the device may still be valuable in this case as a tool to identify complications in amputation rather than simply success or failure.

Skin pigmentation differences can introduce variability to the measurements collected from the subjects in this study. In order to overcome these differences the disclosed methods can include the identification of a healthy region of the patient's tissue to which the wound tissue measurement can be normalized. Other alternatives mat automatically identify a melanin index of the patient's skin, and the melanin index can be input as a patient health metric either as a variable in the classifier or as a factor in selecting a suitable classifier from a number of different classifiers.

Another issue is that normal blood-flow to the skin can be seen in patients with PAD. This could be the result of compensation by collateral vessels. However, it is shown that patients with PAD have poor response to exercise and short-term ischemia. One alteration that can be easily performed is to test the patient's imaging signal after inflation of a pressure cuff in the measured limb to create ischemia for 3 min. PAD is known to lengthen the time to reach 50% of peak reactive hyperemia response, and this can be measured by the same optical properties of the tissue that the amputation site analysis system assesses.

Figure 15C:
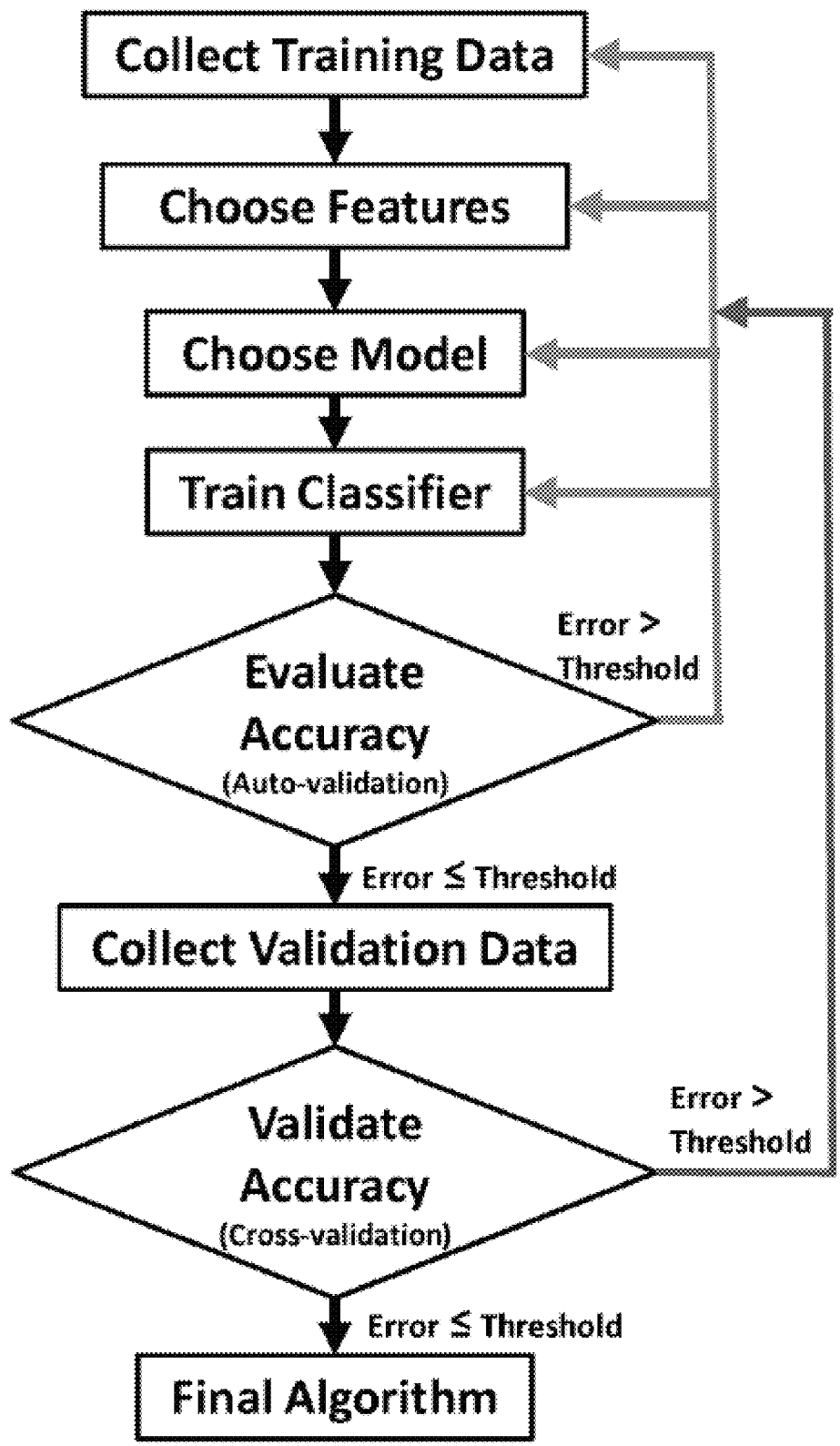

FIG. 15C illustrates example steps for generating a machine learning model according to the present disclosure. Machine learning (ML) can be a valuable tool for simultaneous analysis of multiple variables to arrive at a medical diagnosis, for example PPG information, MSI information, and patient health metric information as described herein. The method of developing a ML tissue classifier as described herein can include the following steps as shown in FIG. 15C: 1) define the clinical question 2) select variables to measure 3) collect data to train the classifier 4) measure the accuracy of the classifier 5) identify sources of error 6) revise the classifier to correct for error and improve accuracy 7) freeze and validate accuracy using an independent dataset (FIG. 3).

One consideration in development of the disclosed ML classifier is transferability of the model from a clinical study cohort to the total population. To ensure better transferability, careful consideration can be made to select training data that represents the eventual population on which the classifier will be used. To this end, the classifier can be separated in some implementations into a number of variations based on training data grouped by common values of patient health metrics, for example diabetes status, BMI, smoking status, and the other metrics described herein. Training data can be grouped based on common values of one or more patient health metrics to provide a number of refined classifiers specific to certain patient populations. Also, selection of the clinical variables implemented in the model can be rigorous. As more data is collected from a population of interest, new information can be integrated into the database and used to re-train or "smarten" the classifier(s).

ML is well suited to handle the multivariate problem of predicting healing at a selected LOA. In the diagnosis of LOA, there are many factors that provide useful information but their individual importance to the final decision currently depends on qualitative clinical judgment. In contrast, ML integrates multiple variables and assigns these variables an appropriate weight leading to a quantitative output. The tissue classifier analyzes optical data collected by PPG imaging and MSI to quantitatively predict amputation site healing. The output can be translated into an image that classifies the microcirculation health of skin tissue at a potential LOA and/or identifies a line or region corresponding to predicted optimal LOA.

As part of this assessment, the disclosed techniques can gather data from numerous amputation patients with the purpose of training a diagnostic machine learning classifier for diagnosing the healing potential in various amputation scenarios. Imaging via the disclosed devices is rapid, non-invasive, and non-contact, and as such imaging studies can be performed in routine care settings such as the bedside or pre-operatively.

Figure 16:
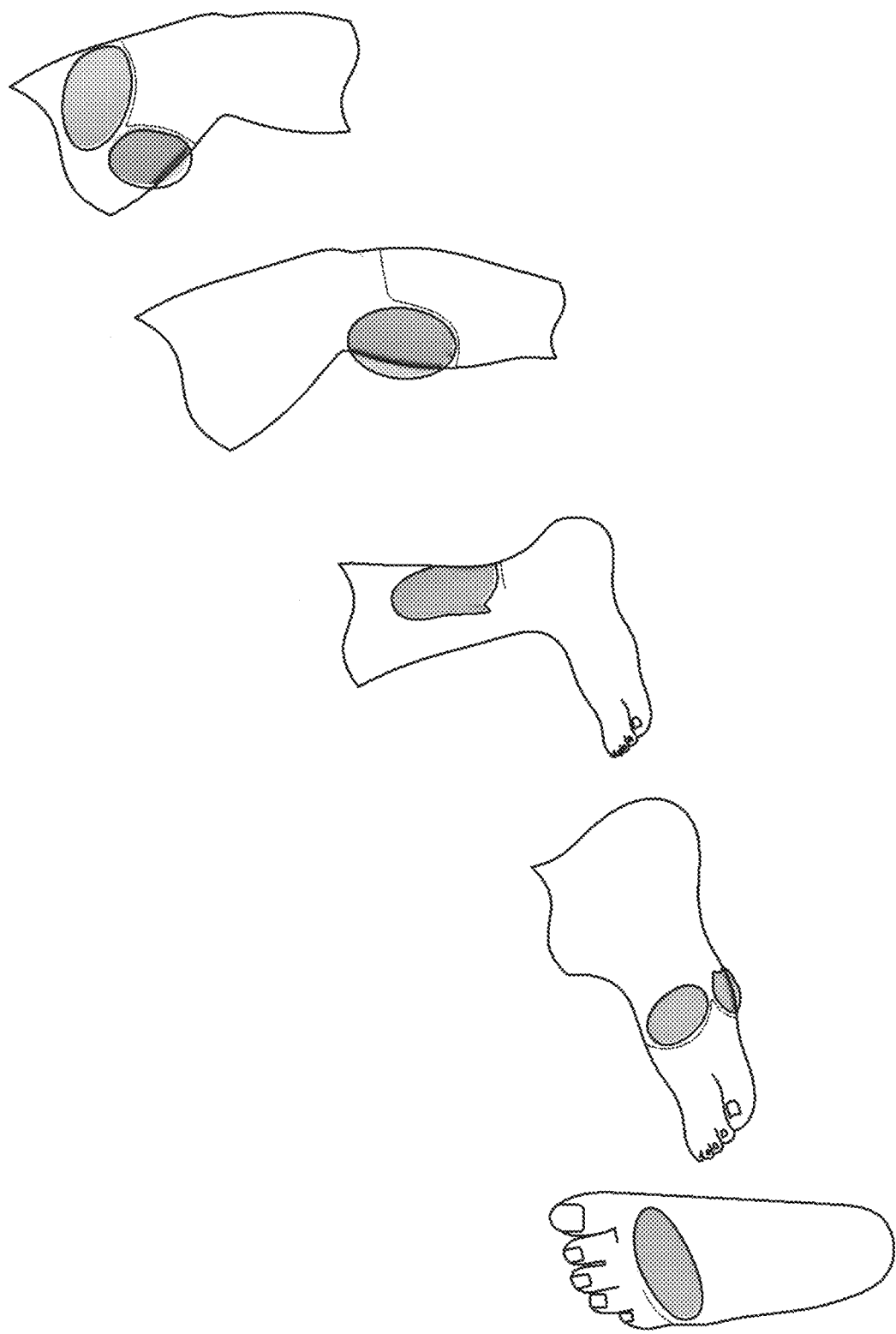
FIG. 16 illustrates a graphical example diagram of tissue involved in traditional amputation procedures.

FIG. 16 illustrates a graphical example diagram of tissue that can be involved in amputation procedures. Dotted lines indicate the location of skin incisions and red ovals indicate the location of skin that must be viable for successful primary healing of the amputation.

Significant patient health information that can be used in the diagnostic model may be collected by the clinical staff at the individual clinical sites. The disclosed techniques do not collect any data that is beyond standard-o-care. These patient health metrics can include, but are not limited to: metrics of diabetic control (e.g., HbA1c, glucose, and insulin), smoking history, obesity (e.g., BMI or waste circumference), nutrition (e.g., albumin, pre-albumin, transferrin), infection (e.g., WBC, granulocyte status, temperature, antibiotic use), age, mechanism of injury, and important medication (e.g., glucocorticoids or chemotherapy). Values of these patient health metrics (for example, a binary yes or no value, a value representing a degree of the patient health metric on a scale, and the like) can be added to the diagnostic classifier by inputting the information into the software on the amputation site analysis system.

A machine learning classifier can sort subjects into the non-healing (+ event) and healing (− event) classes based on the clinical features collected for each patient. Some implementations can include all of the features in the classifier. The classifier's accuracy can be determined by 10-fold cross-validation as follows: first generating the classifier coefficients with 60% of the subjects included at random, and then the remaining 40% of the subjects will then be sorted by the trained classifier. The classifier's accuracy in sorting the subjects in the 40% hold-out group can be calculated using standard sensitivity and specificity methods. This can be repeated 10 times to generate a robust quantification of accuracy.

Figure 17A:
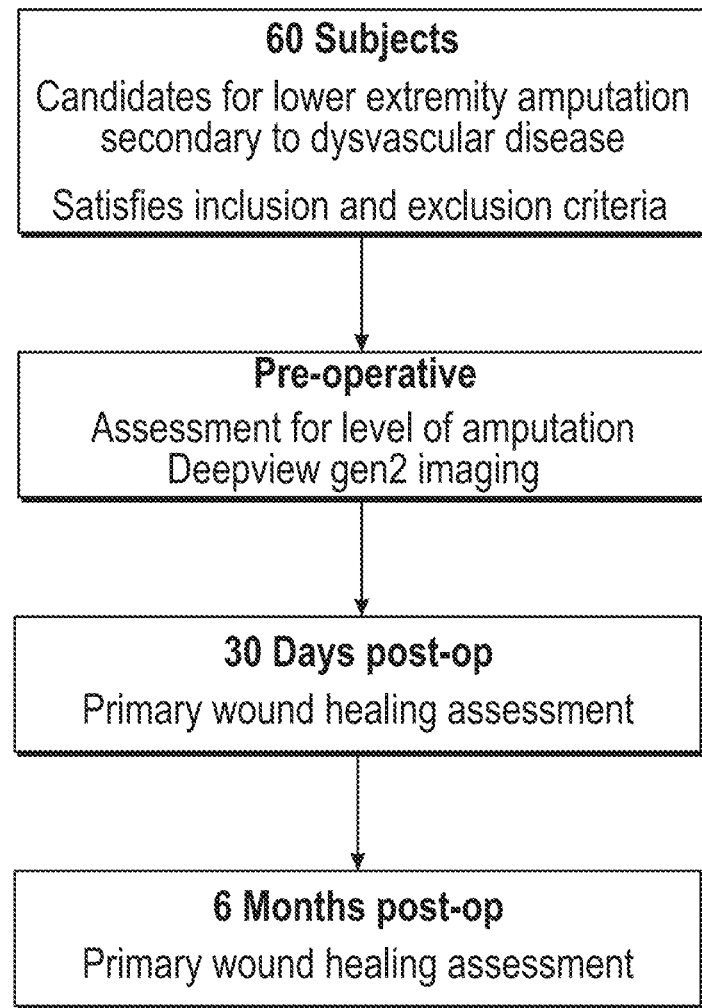
FIGS. 17A and 17B illustrate example clinical study flow diagrams.

FIG. 17A illustrates an example clinical study flow diagram for amputation site imaging evaluation. Subjects are selected for satisfying inclusion and exclusion criteria. Microcirculation data for each subject can be collected by imaging the skin using the disclosed MSI and PPG imaging device. Scans of approximately 30 sec each can be obtained from each limb awaiting amputation. The device can image regions of the ankle and foot according to the traditional surgical methods of amputation in PAD patients including: above the knee (AKA), below the knee (BKA), above the ankle (i.e., foot), transmetatarsal, or toe. The regions of skin that are used as a flap to cover the stump can be selected for analysis to identify whether the flap tissue has a required level of circulation for contributing to a successful amputation (FIG. 16). PPG and MSI images can be collected from the region of skin that would be used for the skin flap over the most distal portion of the stump at each traditional LOA. This region of tissue can be selected due to its impact upon the primary healing of the surgical site.

Figure 17B:
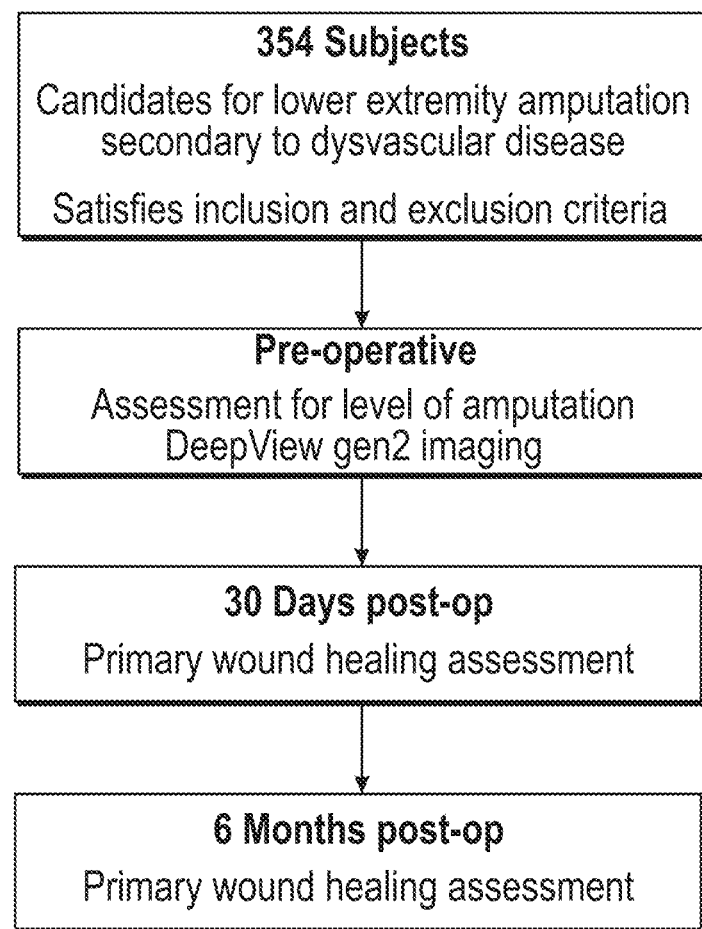

FIG. 17B illustrates an example clinical study flow diagram for amputation site imaging evaluation. Subjects are selected for satisfying inclusion and exclusion criteria. Diagnosis of amputation site healing can be made during imaging using the disclosed imaging device. Scans of approximately 30 sec each can be obtained from each leg awaiting amputation. The device can image regions of the ankle and foot according to the traditional surgical methods of amputation in PAD patients including: above the knee (AKA), below the knee (BKA), above the ankle (AAA), transmetatarsal, or toe. The regions of skin that are used as a flap to cover the stump can be selected for analysis (FIG. 16).

Significant patient health information used in the diagnostic model can be collected by the clinical staff at the individual clinical sites or authorized for automatic extraction from an electronic medical information database such as a patient electronic medical record. The disclosed techniques comply with all applicable privacy regulations and do not collect any data that is beyond standard of care. Patient health metrics can include: measures of diabetic control (e.g., HbA1c, glucose, and/or insulin), smoking history, obesity (e.g., BMI or waste circumference), nutrition (e.g., albumin, pre-albumin, or transferrin), infection (e.g., WBC, granulocyte status, temperature, or antibiotic use), age, and/or important medication (e.g., glucocorticoids or chemotherapy). This information can be added to the diagnostic classifier by inputting the information into the software on the amputation site imaging device or used to select an appropriate classifier trained based on data from patients with corresponding patient health metric values.

PPG and MSI imaging measurements from the five amputation sites of the affected limb can be evaluated to determine the wound healing potential. From each limb, the disclosed techniques can determine an overall healing score and compare these measurements to the actual amputation success in the limb to get an overall accuracy of the assessment. This can result in receiver operating characteristics (ROC), an outcome measure of sensitivity and specificity.

For one possible outcome measure of grading wound healing, the disclosed techniques can compare the automated amputation site diagnosis from the location of amputation determined by the clinician to the success of that amputation determined by the standardized wound healing assessment. This analysis can result in a receiver operator characteristic (ROC) curve for the amputation site diagnostic classifier.

This trial establishes the device's sensitivity and specificity and tests that these numbers outperform clinical judgment to select LOA. The established goal was for the amputation site analysis system to achieve 95% sensitivity and 95% specificity in diagnosing LOA to overcome the poor 70-90% accuracy of current clinical judgment. In order to establish a sample size, the disclosed techniques can first put this in terms of positive predictive value (PPV) and negative predictive value (NPV), which required that the prevalence of the disease be known. The disclosed amputation site analysis techniques can identify the prevalence of re-amputation to a more proximal level in the population to be screened (patients >18 years of age requiring initial amputation on the affected limb due dysvascular disease) to be approximately 20% (reference). Therefore, the desired positive predictive value is 97% and the desired negative predictive value is 93%.

An analysis of sample size to test the following hypotheses was performed using the methods outlined by Steinberg et al., 2008, "Sample size for positive and negative predictive value in diagnostic research using case-control designs," Biostatistics, vol. 10, no. 1, pp. 94-105, 2009. Where the significance level ($\alpha$) is 0.05 and the desired power ($\beta$) is 0.80.

| For PPV | for NPV |
|---|---|
| $H_0$: $PPV_{system}$ = $PPV_{clinical\ Judgment}$ | $H_0$: $NPV_{system}$ = $NPV_{clinical\ Judgment}$ |
| $H_1$: $PPV_{system}$ > $PPV_{clinical\ Judgment}$ | $H_1$: $NPV_{system}$ > $NPV_{clinical\ Judgment}$ |

Figure 18:
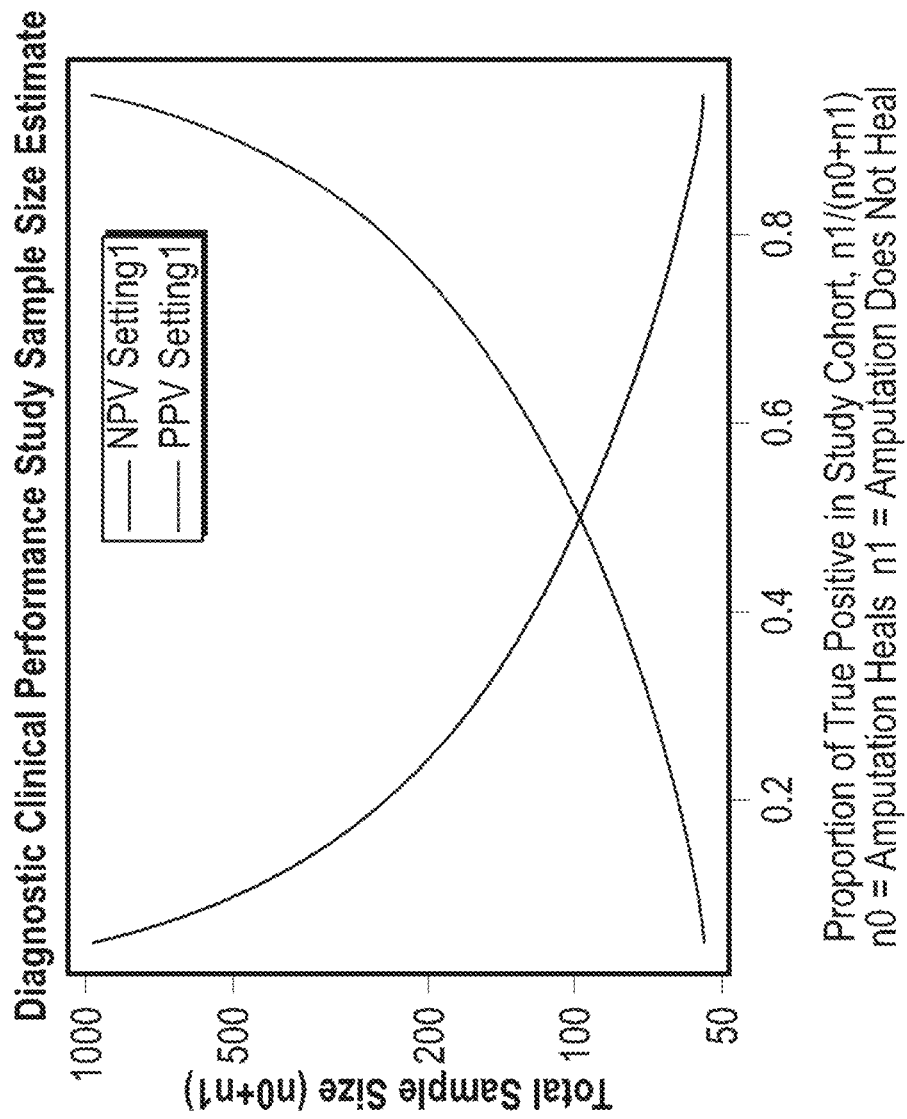
FIG. 18 illustrates example statistical sample size analysis results.

The results show to reject these null hypotheses ($H_0$) the disclosed techniques can must enroll a total number of 236 lower limbs with ⅕ of the limbs being non-healing (+ event) according to the healing assessment (FIG. 18). However, the disclosed techniques can cannot pre-select this ratio to be ⅕, because the disease state of the subjects prior to enrollment may not be known. Therefore, this ratio may differ. If the ratio is much lower, ¹⁄₁₀ of the limbs being non-healing (+), the disclosed techniques can require approx. 450 total limbs and if much higher, ⅗ non-healing (+) limbs, the disclosed techniques can require only 124 total limbs.

Figure 17C:
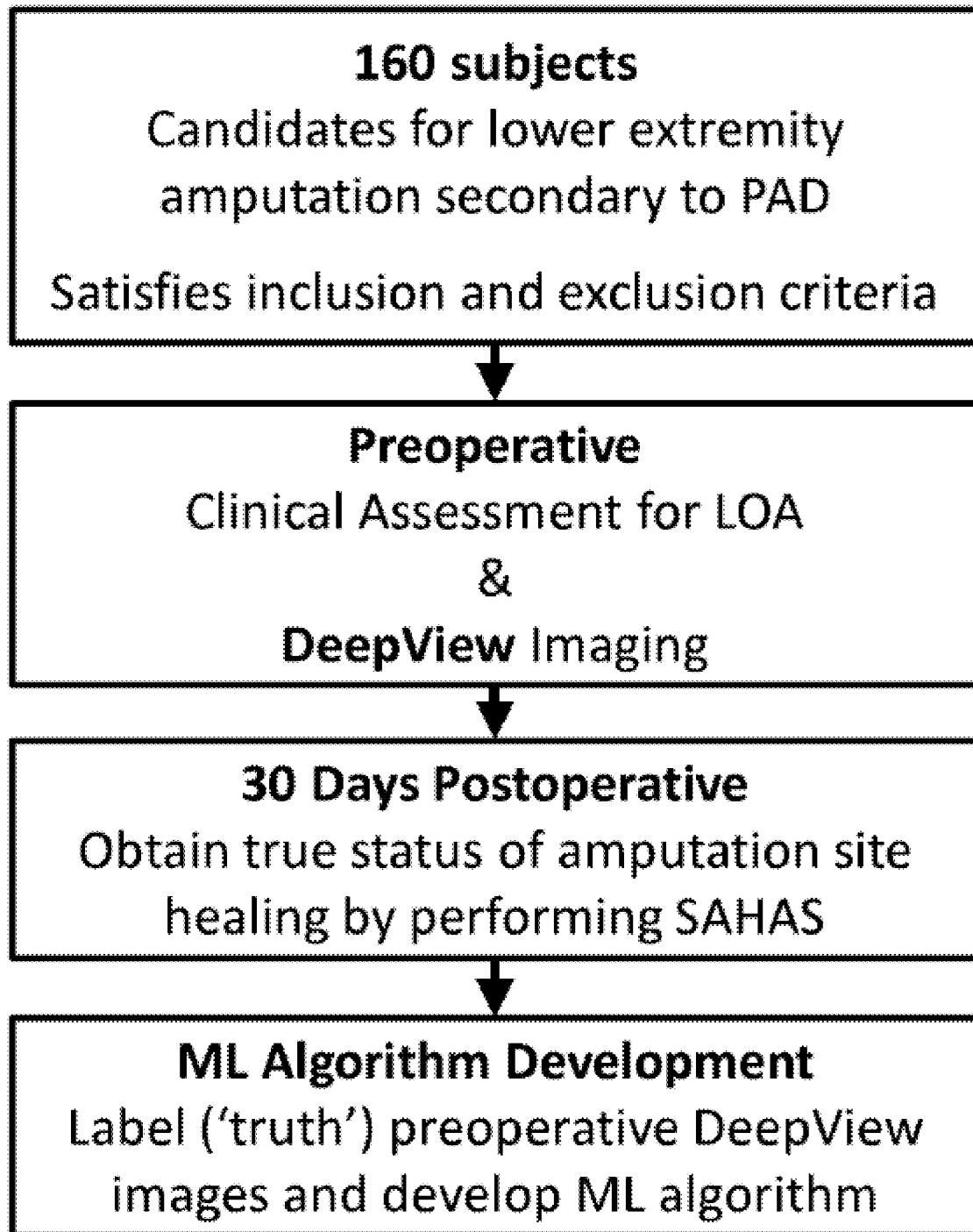
FIG. 17C illustrates an example training study flow diagram.

FIG. 17C illustrates an example training study flow diagram for training a machine learning classifier as described herein. In Phase I, the disclosed imaging devices will be used to gather data to finalize training of the classifier in a clinical study enrolling a cohort of amputation patients (FIG. 17C). Imaging studies will be performed prior to amputation in routine care settings as part of a nonsignificant risk study.

During this training study, a large dataset of training images will be obtained on which testing of variables in specific classifier components will be evaluated with the goal of being able to achieve a sensitivity and specificity of 90% sensitivity and specificity. Standardized Amputation Healing can be determined based on the ultimate outcome of the amputation (healing or non-healing). Training can be performed via collection of data that accurately represents a population on which the classifier will eventually be used. Importantly, the classifier can only be as accurate as the methods used to identify the true status of the training data, in this case the healing or non-healing of the amputation site selected by a clinician. Thus, the disclosed techniques involved generating a Standardized Amputation Healing Assessment System (SAHAS) to classify outcomes (Table 3 below). Additionally, skin tone is expected to impact at least the MSI optical measurements. Therefore, the amputation site analysis system can categorize subject skin tone according to their melanin indices, for example using data from a portable colorimeter, and utilize this data in classifier development.

TABLE 3

| Category | Characteristics |
|---|---|
| Healing | Healing within 30 days and no need for revision or revasculariztion. |
| Non-healing | Incomplete healing at 30 days or development of necrosis and/or gangrene, and/or the re-amputation to a more proximal level, and/or subsequent revascularization |

Training data will be gathered from 49 hospitals and 8 wound care centers, having one of the busiest vascular surgery groups. Subjects will be evaluated for inclusion and exclusion criteria. Inclusion criteria include that the patient requires initial amputation on a limb secondary to PAD, is able to give informed consent, and is at least 18 years of age. PAD is defined as arterial insufficiency due to atherosclerosis based on one or more of the following assessments: ABI 0.9; duplex ultrasonography showing clinically significant occlusion; arteriography; or assessment demonstrating median arterial calcification. Exclusion criteria include no diagnosis of PAD, prior amputation on the affected limb, or life expectancy less than 6 months.

Patients will be assessed 30 days postoperatively to determine whether the primary wound at the clinician-selected LOA has successfully healed according to the SAHAS so that the classifier can be trained.

The lower limb to be amputated will be imaged by hospital staff trained to use the disclosed imaging devices. Research coordinators will document the subjects' melanin index and at 30-days the SAHAS data obtained by the attending vascular surgeon.

One hundred sixty (160) subjects will be enrolled and imaged according to a standardized protocol prior to amputation (FIG. 17C) Imaging will be performed during the same clinical encounter at which LOA has been determined by the clinician, who will be blinded to the amputation analysis results. Thirty days following amputation, subjects will be assessed for postoperative wound healing using the SAHAS (Table 3). The pre-amputation image data can be "truthed" based upon the results of the clinical healing assessment (healed versus non-healed) and used to train the classifier.

The classifier to classify the non-healing and healing categories can be trained from collected data. To train the classifier's ability to correctly identify the microcirculation zones in an amputation site, the disclosed techniques can "truth" the captured images to the true status (for example, ground truth mask; FIG. 20B) of the amputation site's microcirculation zones and train the classifier based on the truthed data. To obtain the true status of the amputation site's microcirculation zones, subjects will be clinically assessed at 30 days to categorize the amputation site according to the SAHAS. Results of the clinical healing assessment will serve to aid the physician in labeling the true zones of amputation site microcirculation on the captured images. Ground truth plus raw image data can be included as inputs to the classifier training protocol.

The classifier can initially include all the proposed tissue measurements (PPG and MSI). These measurements, as well as patient health metric information, can be used in training the fully convolutional neural network that was used to generate the preliminary data. Additionally, pre and post-processing methods and other classifiers can be tested to improve accuracy. Using the A 10-fold cross-validation procedure can determine classifier accuracy: 1) generate classifier coefficients using training samples consisting of 60% of the subjects selected at random without replacement (training group); 2) classify the remaining 40% of subjects (test group) with the trained classifier; 3) quantify the classifier's accuracy; 4) repeat 10 times to generate a robust measurement of sensitivity and specificity. Selection of the most accurate classifier architecture(s) can then be made. Further analysis of these top performers can involve generating receiver operator characteristic (ROC) curves.

To address the potential effect of skin tone, the disclosed techniques can evaluate the effect of skin tone on the raw optical measurements from the different microcirculation classes. If this effect is significant, the disclosed techniques can incorporate each subjects' melanin index measurement into the classifier, re-train, and evaluate classifier accuracy. The melanin index can be identified automatically in some implementations using the disclosed imaging systems, can be input by a clinician, and/or can be provided from an electronic record. In some embodiments this can provide a significant improvement in classifier performance, and can be used for developing methods to obtain a subject's melanin index during imaging with the disclosed imaging device (for example, by developing a classifier to obtain a melanin index directly from a MSI measurement).

After the initial sensitivity and specificity are established, the disclosed techniques can improve the classifier with a standard set of methodologies. One issue in this process is to address a trade-off inherent to complex classifiers. Complex classifiers fit very well to the data from which they were derived, but they may not transfer to another population due to their complexity. In order to address this, the disclosed techniques can conduct variable selection to establish a combination of PPG and MSI measurements that deliver high accuracy with minimal redundancy between measurements. Variable selection simultaneously ranks the importance of each measurement in the model to highlight which optical signals are most critical to the diagnostic accuracy of the disclosed technology. The resulting refinements to the classifier can allow for successful generalization to subsequent amputation patients. Additionally, the disclosed method to study a variety of ML techniques can enable obtaining models of various complexity to validate in Phase II, described below with respect to FIG. 17D.

A cohort size of 160 was determined by estimating the subject number needed to reach the maximum classifier accuracy. Currently, there are no standardized methods for predicting the training size for machine learning classifier development. However, studies show that as the number of observations in the set of training data increases, a machine learning classifier's accuracy converges to its maximum and the addition of more training data will not improve performance. In order to identify the most likely convergence point for the disclosed amputation site tissue classifier, the described training techniques can simulate the optical data from viable and diseased microcirculation tissue using data from the preliminary study section. With this data, the disclosed techniques can train four different machine learning classifiers and identify the sample size at which these classifiers would converge to their maximum accuracy. Multiple classifiers to can be used to obtain a more thorough assessment of the convergence point. These can differ from the classifier that was used in the preliminary data section in that these four common classifiers can be less complex and thus expected to provide a more conservative estimate of sample size as opposed to the complex convolutional neural network used in the preliminary data examples.

Sufficient data can be collected and cross-referenced to post-amputation clinical wound healing assessment using SAHAS for training of a robust classifier for predicting amputation site healing. Phase I (Preliminary testing) of the classifier can demonstrate an accuracy greater than the desired 90% sensitivity and specificity in order to have a high probability of success in Phase II. Based upon pre-clinical testing amputation subjects, a sample of 160 subjects can be sufficient to train a robust classifier with 90% accuracy, which exceeds the current standard of care.

The classifier is expected to perform very well on the training data, as is the case with many predictive models. However, an issue is addressing the generalizability of the classifier to the data not contained in the training dataset. "Overfitting" is the term used for machine learning models that are highly accurate in the training dataset, but perform poorly on the general population. The purpose of the Phase II validation study is to assess overfitting. The probability of success in Phase II can be increased with two methods. Method one is to utilize a machine learning technique called regularization to reduce the complexity of the classifier as well as the potential for overfitting to be a significant issue. A second method can be to generate multiple classifier variations by employing a variety of machine learning techniques for sorting data, for example by grouping training data into subsets based on commonalities in patient data. Each technique can be tested on the validation data in Phase II.

If skin tone is determined to be a cofounding variable to the classifier's predictions, this can be addressed in one of two ways: 1) incorporate this variable into the ML classifier and determine if the presence of this feature improves performance; or 2) subgroup training data by the levels of this variable and identify the levels where classifier performance is insufficient. Once these levels are identified, the disclosed techniques can split the data and generate a separate classifier at each level. This may involve the collection of more training data from certain subgroups within a melanin index scale.

In rare instances, non-healing amputation sites could be the result of processes other than lack of microcirculatory blood flow to the wound. For example, surgical site infections, poor nutritional status, or subject non-compliance with wound management may prevent healing of the amputation site independently from factors that the classifier measures. In these cases, the subject can be reviewed with their physician to determine whether their data should be included for classifier training.

Figure 17D:
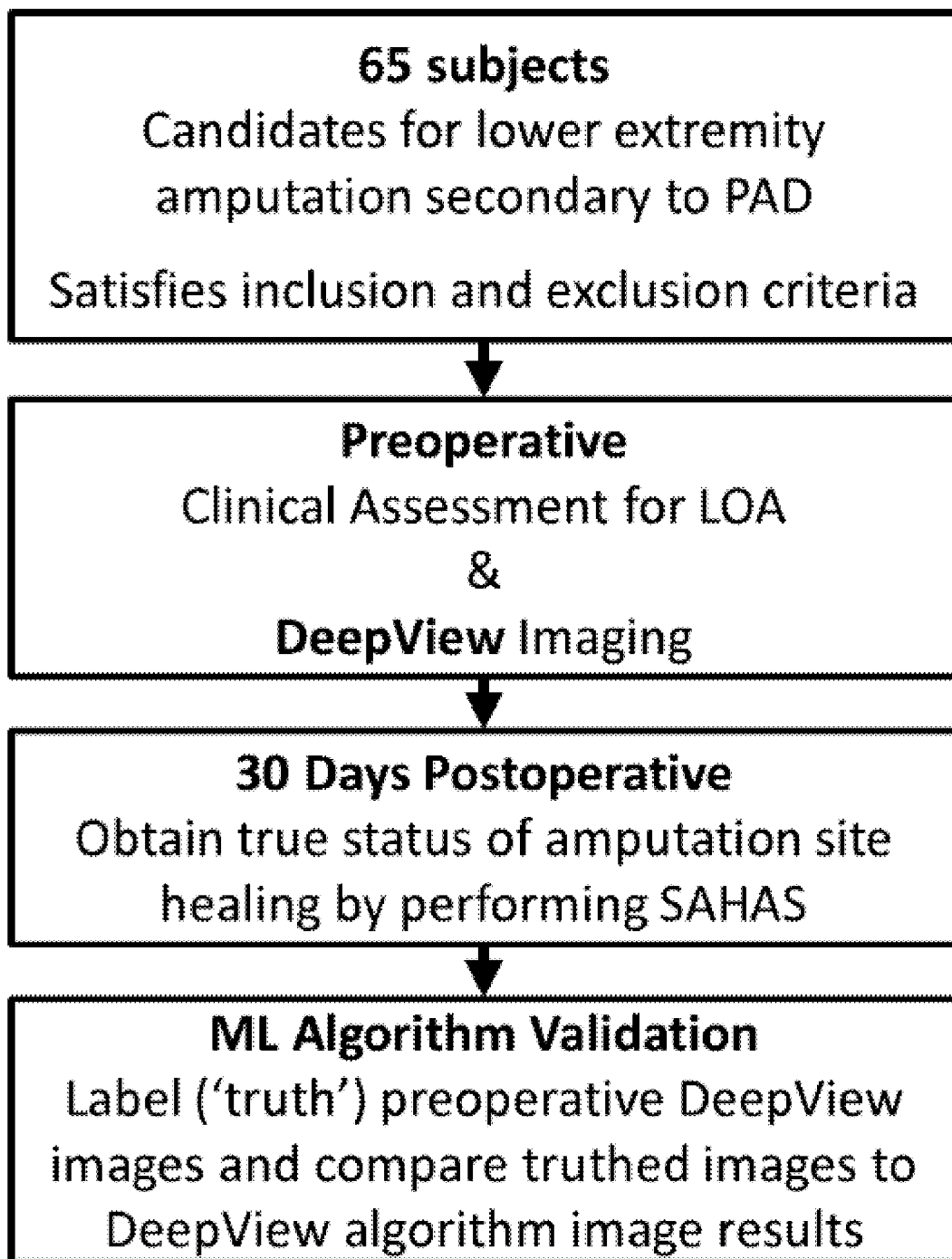
FIG. 17D illustrates an example validation study flow diagram.

FIG. 17D illustrates an example validation study flow diagram for Phase II, which includes validating results of a trained machine learning model as described herein. Phase II can be a validation study to further evaluate the sensitivity and specificity of the disclosed machine learning model for selection of LOA. At the completion of this phase, the disclosed classifier can be confirmed have 90% sensitivity and specificity for detecting the microcirculation health of skin tissue at potential LOAs. In addition to validation of the accuracy of the classifier, the classifier's assessment of the amputation site can be compared to the clinical assessment to demonstrate the potential impact of the device in a clinical setting.

Location, patient recruitment, consent, inclusion & exclusion Criteria, and data collection can be identical to Phase I.

The previously trained and frozen classifier can be validated using data from the Phase II Study (FIG. 17D). Validation can entail proving that the classifier meets the predetermined sensitivity and specificity goals when applied to a new study population, confirming the generalizability of the classifier to patients outside the original training cohort. The goal can be 90% sensitivity and specificity of the disclosed classifier's ability to correctly identify the microcirculation zones in an amputation site.

The clinician's assessment of the healing potential of tissue at the amputation site can be recorded and compared to the disclosed classifier's determination of healing potential. Following the identification of the true healing status of the amputation, the validation techniques can determine how many correct amputation assessments were made by physicians in comparison to those made by the classifier to demonstrate the potential impact of the device in a clinical setting.

The clinical trial workflow for the Phase II Validation Study reflects the Phase I Training Study workflow, allowing for validation of the data collected during the Phase I Training Study. The validation study design can include 65 subjects depending on the incidence of non-healing amputation sites in the Phase I Training Study.

To validate the classifier's ability to correctly identify the microcirculation zones in an amputation site, the validation techniques can compare the ML image result to the true status of the amputation site's microcirculation zones. The ground truth mask of the amputation site's microcirculation zones can be obtained in the manner used in the Phase I training study. The ground truth mask can be compared to the image of microcirculation zones produced by the classifier. This comparison can validate the sensitivity and specificity of the machine learning classifier in identifying the microcirculation status of the amputation site.

Comparison of the clinician assessment of healing potential to the classifier's assessment can include the following analysis: obtaining the physician's success rate can be done by reviewing the 30-day healing status of the amputation using the previously collected SAHAS data; where successful amputations will be equivalent to the physician's success in selecting the appropriate site. To determine the classifier's successes and failures, an area of tissue can be identified in the pre-amputation output image, where the identified area could be used to cover the amputation site (FIG. 16). The percentage of this identified area, or region of interest (ROI), classified by the system as non-healing can be calculated. FROC analysis can be used to identify a threshold percent of non-viable tissue in the ROI that most accurately predicts a non-healing amputation. This analysis can provide a single 'healing' or 'non-healing' prediction for each amputation site assessment. The classifier's decision to amputate based on this ROI analysis can be compared to the physician's amputation healing results using a McNemar's test of repeated proportions.

This Phase II study is designed to validate the sensitivity and specificity of the disclosed technology in determining the skin's microcirculatory status at potential LOAs, and compare the accuracy of the classifier to the true microcirculation status. A well-established method of collecting a validation data set that is 30% as large as the training set of 160 subjects can be used for validation. Given the potential for confounding circumstances that will affect the healing of amputations, an additional 10% more subjects can be included, resulting in a total of 64 subjects.

The results of the power analysis for the secondary outcome is 65 total subjects. The secondary outcome is to compare the classifier's determination of healing potential based on an ROI analysis to the physician's amputation healing results using a McNemar's test of paired proportions. The following contingency table (Table 4) represents how the validation study can pair the results of amputation site selection from both clinicians and the disclosed classifier:

TABLE 4

| | | Clinician's Success in Predicting | |
|---|---|---|---|
| | | Success | Failure |
| Classifier's Success in Predicting Amputation Healing | Success | $\Pi_{11}$ Agreement | $\Pi_{12}$ Disagreement |
| | Failure | $\Pi_{21}$ Disagreement | $\Pi_{22}$ Agreement |

Hypotheses for this test are: $H_0$: $\Pi_{12} \neq \Pi_{21}$ and $H_1$: $\Pi_{12} \neq \Pi_{21}$; where $\Pi_{12}$ is the expected proportion of automated amputation site analysis failures when clinicians are successful, and $\Pi_{21}$ being the expected proportion of clinician failures when automated amputation site analysis is successful. Using the formula:

$$N = \left\lceil \left( \frac{z_{1-\alpha}\sqrt{\pi_d} + z_{1-\beta}\sqrt{\pi_d - (\pi_{12} - \pi_{21})^2}}{\pi_{12} - \pi_{21}} \right)^2 \right\rceil \text{ Where } \pi_d = \pi_{12} + \pi_{21}$$

To perform this calculation, the disclosed techniques can estimate 1112 as 0.27 and $\Pi_{21}$ as 0.07. These numbers were based on the prevalence of failed amputations, approximately 30%, and the desired 90% sensitivity and 90% specificity of the disclosed techniques for predicting LOA. The validation can use a 2-sided test with power set to 0.80 and alpha 0.05. Hence the sample size of 65 subjects will provide 80% power to test this secondary outcome.

The Phase II study can validate that the classifier meets the stated goal of 90% sensitivity and specificity in determining the microcirculation status of the potential amputation site at multiple LOAs. In addition, this study can indicate that this technology represents a significant improvement over the current standard of care for patients undergoing amputation secondary to PAD.

This study design is predicated on the Phase I study represented by FIG. 17C.

The described training and validation techniques set a high bar for the application of the disclosed technology for the selection of appropriate LOA. However, amputation failure is a significant clinical problem which lacks a user friendly, quantitative, and safe solution; and any incremental improvement in the delineation of the proper LOA should result in significant improved patient outcomes and cost savings.

FIG. 18 illustrates example statistical sample size analysis results. Total sample size according to the ratio of non-healing (+) to healing (−) amputations in the study cohort. Significance level ($\alpha$) is 0.05 and the desired power ($\beta$) is 0.80.

To account for the possible variations in the ratio of positive to negative subjects, the disclosed techniques can include approx. 50% more subjects to the original estimate of 236. Therefore, the total sample size can be established at 354 total subjects. The disclosed techniques monitored the study data as it was taken and calculated the total number of limbs studied and the ratio of unsuccessful (+ event) to successfully amputated (− event) limbs, and stopped the study once an appropriate ratio and total sample size was obtained.

To determine how well the automated amputation site analysis output correlates to primary wound healing, the disclosed techniques compared the automated results to the standardized healing assessment that sorts subjects into healing or non-healing groups. From this comparison, a correlation was discovered that supports a high sensitivity and specificity for predicting primary healing after amputation. The ROC contained a decision threshold value that results in a sensitivity and specificity greater than the required values established by the current standard of care (70-90% accuracy).

Large enough sample size for machine learning training data can power the importance of all non-imaging data (patient health metrics) used in the diagnostic model. For instance, diabetes can be an important clinical feature, but in small sample sizes all the patients may have diabetes or diabetes may not occur at a ratio that allows for sufficient power to study its effects. Therefore, the presence of this comorbidity in the disclosed diagnostic classifier may not be interpreted without sufficient sample size. A patient cohort can have many similarities in their overall health status, but some of these variables can be measured at various levels and not simply dealt with as dichotomous. For instance, diabetic subjects may have a range of control as measured by the HbA1c and blood-glucose testing. For the case where this is not possible, the disclosed techniques can consider the continued collection of this data by looking at a much larger amputation population. In some embodiments, as additional data is collected from the disclosed imaging devices in a centralized database and the machine learning classifier(s) are refined by training from such additional data (for example, using similar techniques as described above), a refined classifier or set of classifiers based on different subsets of training data can be provided to diagnostic machines in the field.

Figure 19:
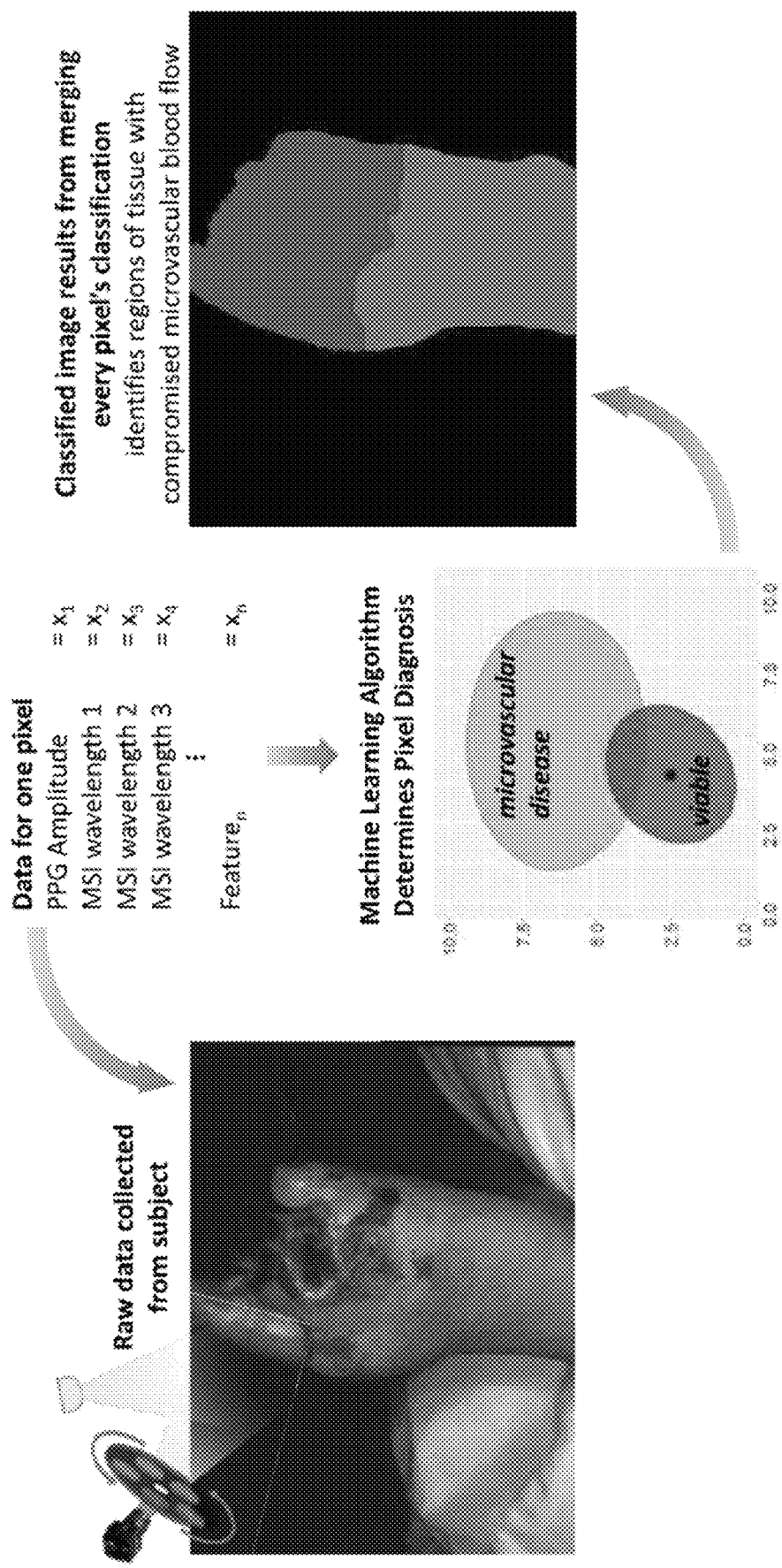
FIG. 19 illustrates an example graphical representation of an amputation site tissue classification process as described herein.

FIG. 19 illustrates an example graphical representation of an amputation site tissue classification process as described herein. PPG and MSI data can be collected simultaneously or sequentially from an amputation site. From each of the image's pixels, which can in some examples be around one million pixels, multiple independent measurements can be calculated including the values of the PPG pulse amplitude and the intensity at each MSI wavelength. Data from each pixel can be individually fed into the classifier previously trained with known patient data. The classifier can return one value for each pixel that represents the health of the microvasculature and potential for successful post amputation healing. These can be presented to the physician in the form of an image. For example, the classifications can be displayed by associating specific values or ranges of values with one of a number of tissue categories, generating a visual representation of the category for display (for example, a color or pattern fill), and displaying pixels with the visual representation of the category in which they were classified. As such, a mapping of different tissue health categories can be overlaid onto an image of the patient's amputation site. In some embodiments, a recommended LOA or region of possible LOAs can additionally or alternatively be overlaid onto the image based on analysis of the classified tissue regions.

Figure 20A:
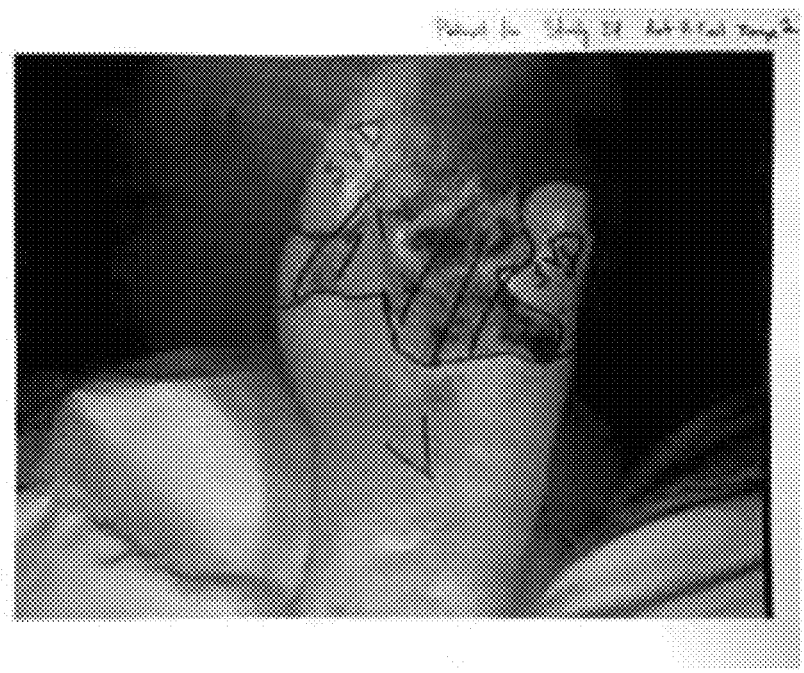
FIG. 20A illustrates an example image of an amputation site marked by a physician.
Figure 20B:
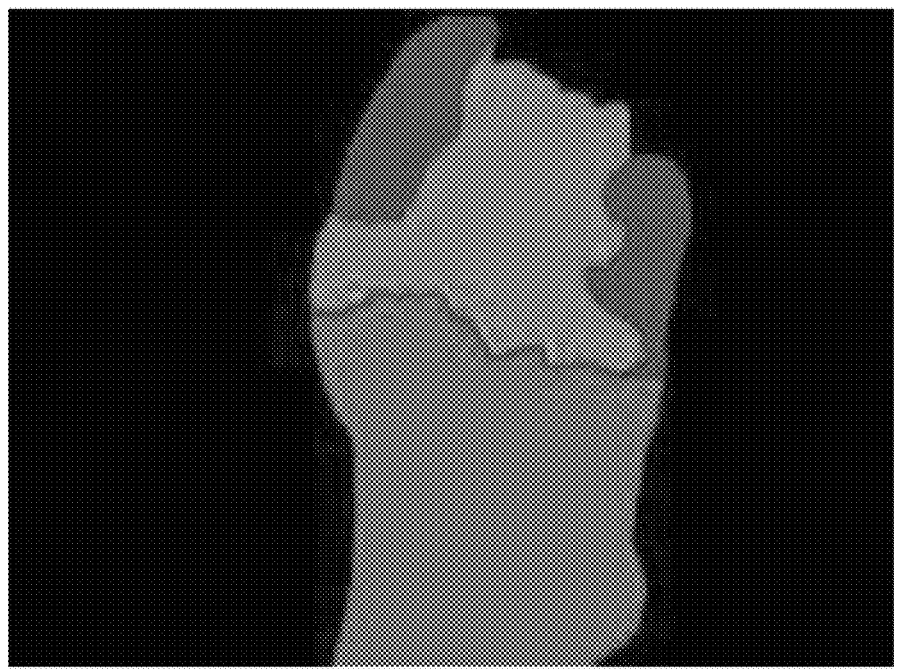
FIG. 20B illustrates an example image of a tissue classification mapping generated based on the image of FIG. 20A.
Figure 20B:
Figure 20B:
Figure 20B:

FIG. 20A illustrates an example image of an amputation site marked by a physician, and FIG. 20B illustrates an example image of a tissue classification mapping generated based on the image of FIG. 20A.

To determine that the classifier accurately identified the microcirculation health of tissue on the lower extremity during the amputation assessment of a subject with PAD, images were collected from a number of subjects prior to amputation. These subjects were followed for approximately 30 days to determine whether the collected images correlated to the eventual amputation site healing status. The subjects had severe PAD and were scheduled for an amputation on one lower extremity.

On the day of their scheduled amputation, just prior to being prepared for surgery, images were collected from the subject from regions of the extremity on which the amputation would take place Images included the area being assessed for amputation, the feet in several cases, as well as other regions of the extremity more proximal to the amputation site. A set of images was obtained from each imaging location. The set included eight MSI images captured at different wavelengths of light including (listed as center wavelength±full-width at half-max): 420 nm±20 nm, 525 nm±35 nm, 581 nm±20 nm, 620 nm±20 nm, 660 nm±20 nm, 726 nm±41 nm, 820 nm±20 nm, and 855 nm±30 nm. These images were captured using the respective wavelength bandpass filters and taken at a frame rate of approximately 4-6 fps. The set also included 400 time-resolved images captured using an 855 nm bandpass filter taken sequentially at a frame rate of 30 fps. When such images are taken back-to-back imaging takes approximately 15 seconds, with around 4-6 fps lapsing between capture of successive MSI images using some systems while other systems can capture all eight MSI images simultaneously. The orientation of the camera can be varied between each image, and in some embodiments the healing classification scores at each pixel can be registered after calculation. The distance between the imaging system and the tissue site was 40 cm, and the field of view of the imaging system was 15×20 cm. The healing or non-healing of the amputation site was evaluated at 30 days postoperatively.

The machine learning classifier was trained to detect three microvascular blood flow regions in the imaged tissue including (1) viable skin (tissue unaffected by PAD), (2) small vessel disease (SVD) (skin with compromised vascularity affected by PAD), and (3) necrosis (skin and underlying tissue that is no longer viable).

To train the machine learning classifier, first the subjects' surgeon 'truthed' the captured MSI/PPG images by demarcating, on an image depicting the imaged regions, the three microcirculation classes. To improve the accuracy of the surgeon's labeling of these images, the surgeon demarcated the image after having obtained knowledge of the 30-day amputation healing evaluation. These demarcated images were translated into digital images used to label each pixel in the subjects' MSI/PPG images (FIG. 20A). Once each pixel was labeled, the machine learning model classifier was trained to classify the categories of tissue microcirculation. The machine learning model used was a fully convolutional neural network, and the data input into this model included MSI and PPG images. The image matrix has the following dimensions: 1408 pixels×2048 pixels×9 features.

The classifier was trained with 72 images from three subjects. Prior to training, one image per subject was held-out of the training set to be used as a test image. Once training was complete, the accuracy of the classifier was tested on this held-out image to obtain the within-the-image classifier accuracy.

Separate from the training images, the system obtained images post-amputation from one subject to determine whether the classifier could make accurate predictions on images not used for training.

Figure 21:
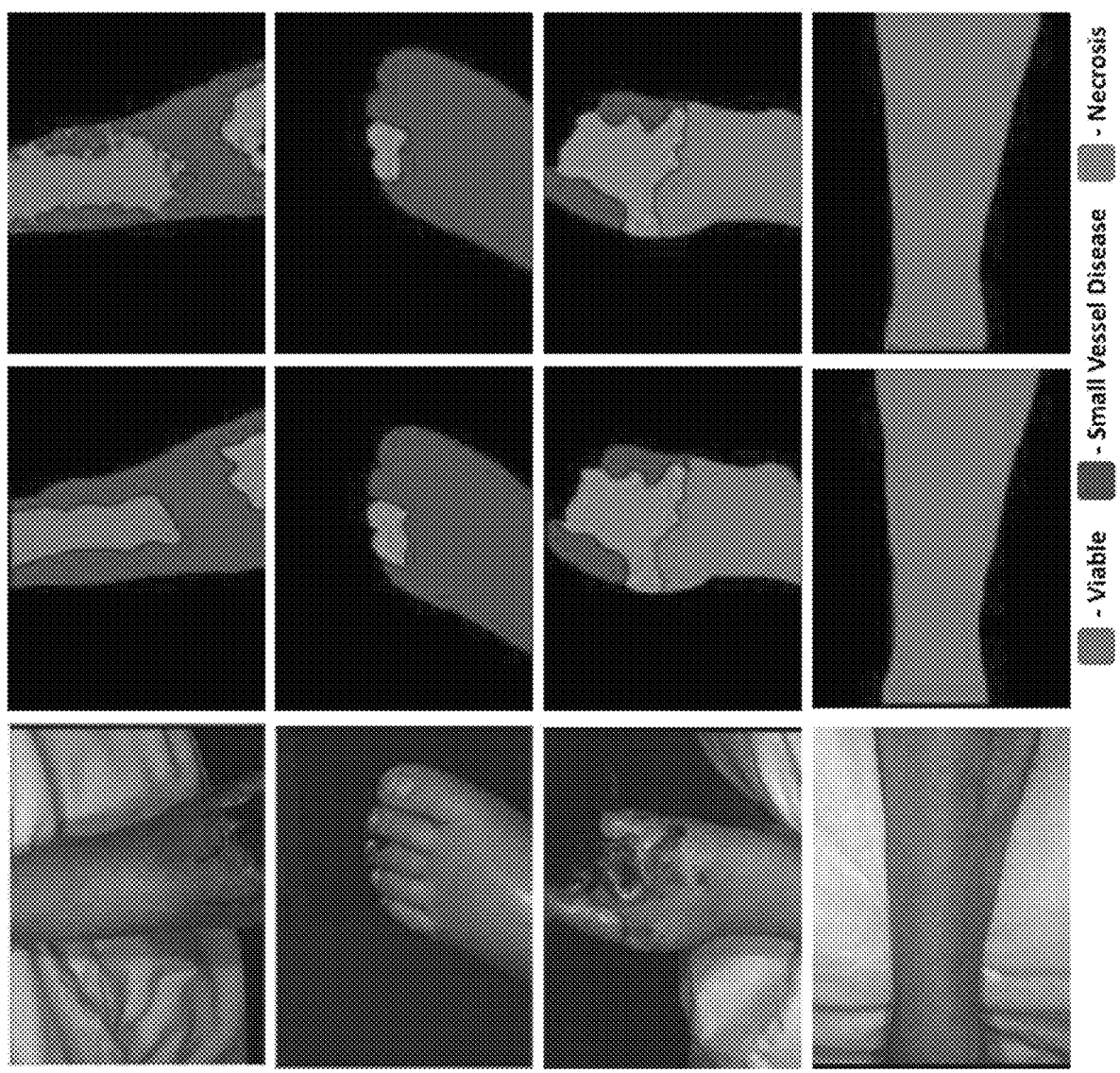
FIG. 21 illustrates cross-validation results for the disclosed amputation machine learning techniques.

FIG. 21 illustrates cross-validation results for the disclosed amputation machine learning techniques. The left column illustrates the color images of amputation sites just prior to surgery; the center column illustrates ground truth data as determined by the surgeons 30 days postoperative; the right column illustrates automated amputation site analysis output results following training of the classifier. This showed that the classified optical data was strongly correlated, 97.5% accuracy, with the surgeon's clinical determination of the three microvascular blood flow regions of the potential amputation sites as shown in Table 5 below. Table 4 illustrates a confusion matrix and average effectiveness of the disclosed amputation healing assessment techniques. The average effectiveness was computed as 97.5% plus or minus 3.4%.

TABLE 5

| Tissue Classifier | True Status or Microcirculation | | | | |
| --- | --- | --- | --- | --- | --- |
| | SVD | Background | Necrotic | Viable | Total |
| SVD | 12.6% | 0.0% | 0.1% | 0.2% | 12.9% |
| Background | 0.1% | 63.9% | 0.1% | 0.1% | 64.2% |
| Necrotic | 0.4% | 0.1% | 3.6% | 0.0% | 4.1% |
| Viable | 1.1% | 0.1% | 0.2% | 17.4% | 18.0% |
| d | 14.2% | 64.1% | 4.0% | 17.7% | 100.0% |

Figure 22:
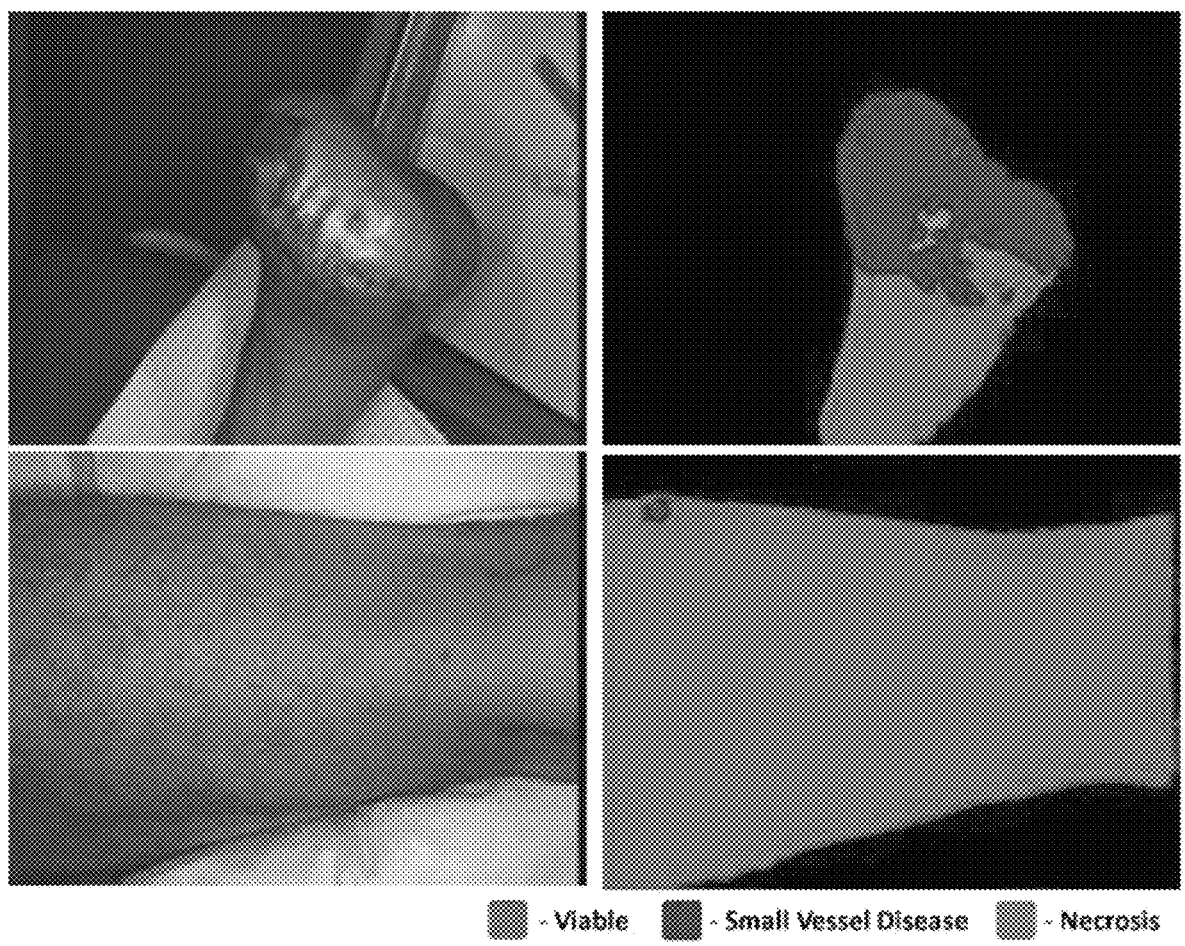
FIG. 22 illustrates example images classified after training of the disclosed amputation machine learning model.

FIG. 22 illustrates example images classified after training of the disclosed amputation machine learning classifier. The top left image depicts a postoperative site of a transmetatarsal amputation where the stump did not heal and required re-operation. This is the same foot depicted in the top row of FIG. 6. The ML classifier output in the top right image shows small vessel disease and necrosis on the skin used to cover the stump, consistent with the clinical outcome. A control image of a subject's healthy thigh, not used in classifier training, (lower left) and ML classifier output of the control image (lower right) demonstrates that the classifier can identify viable tissue with high accuracy In conclusion, the disclosed classifier was trained and tested using images from a preliminary group of subjects with PAD requiring amputations. It will be appreciated that the disclosed techniques could be applied to amputation patients without PAD. The classifier demonstrated excellent correlation with the actual state of the tissue microcirculation in the extremity, approximately 98%. Also impressive is that the classifier can process a new unknown image and accurately identify the microvascular status of the tissue, which means a pre-amputation image can be used to predict a subject's non-healing amputation site.

One embodiment of using the amputation site classifier to classify patient tissue can be implemented using the following steps. A diagnostic system as described herein can capture PPG and/or MSI image data of a wound site, for example a tissue region including a potential amputation site. The system can generate a map of the wound site from image data, for example by rectifying a set of captured images so the same pixel location across the set represents approximately the same physical location of the imaged tissue region. In some embodiments the map can be segmented into pixels depicting the wound site and background pixels not depicting tissue of the patient. The system can determine, for each pixel depicting the wound site, PPG amplitude value and MSI reflectance intensity value. Prior to, during, or after capturing the image data, the system can receive input of patient health metrics, for example as inputs from a physician or as data automatically provided by an electronic medical record.

Based on the patient health metrics, one embodiment of the system can input patient health metric values as variables into classifier together with PPG and MSI values. The classifier can be generated using machine learning techniques as described herein. The system can use the classifier and classify each pixel of the wound site as one of necrotic, viable, or small vessel diseased based on a weighted combination of the PPG value, MSI value, and patient health metric values. The system can generate a mask image visually representing each pixel classification of wound site and output the mask image for display to clinician.

Based on the patient health metrics, another embodiment of the system can select one classifier of multiple classifier variations, where each variation is based on a subgroup of training data, each subgroup representing patients with different combinations of patient health metric values. The selected classifier can be generated from training data having matching patient health metrics to those of the patient of interest. The system can input the determined PPG and MSI values into the selected classifier. The system can use the selected classifier and classify each pixel of the wound site as one of necrotic, viable, or small vessel diseased based on a weighted combination of the PPG value and MSI value at the pixel. The system can generate a mask image visually representing each pixel classification of wound site and output the mask image for display to clinician.

It will be appreciated that some embodiments can implement a combination of the above classification techniques, for example by performing classifier selection based on certain patient health metrics and by inputting the same or other patient health metrics into the classification model. In addition to the mask image, some embodiments can output an automatically determined LOA or zone of potential LOA locations overlaying the mapping of the wound site.

Given a large database of training data that includes information such as sex, diabetes status, age, smoking history, etc., the disclosed ML training techniques can subset the database based upon those parameters that match the values of these metrics for the patient of interest, train a classifier based on this subset of the overall training database, and then provide a more customized classifier for more accurate tissue classification and/or LOA prediction. Alternatively, those parameters can be input in the classifier as variables (for example, coded as 1 or 0 for smoker, 1 or 0 for diabetic, etc.) and then the level of that variable would impact the device's perdition. Such features are referred to herein as "patient health metrics". According to one embodiment, the disclosed classification techniques can select training data that represents the eventual population on which the classifier will be used. This can be done in real time and automatically prior to imaging a specific patient, for example based on known information about the patient, so that each patient's results are gleaned from an individualized pool of training data.

As illustrated in the figures, the output of the classifier can be an image including a mapping of different regions of tissue classifications. Such a mapping can aid the physician in selecting the appropriate LOA by indicating the disease status of the tissue that the physician would be using to construct the amputation. Other embodiments can alternatively or additionally provide a visual representation of a recommended LOA or zone of possible LOA locations, for example determined based on the mapping of the different regions of tissue classifications and a machine learning model associating the boundaries, locations, and extent of the classified tissue regions with a LOA that is likely to provide suitable healing results for the patient. The disclosed systems could automate the process of selecting the appropriate site, for example by providing a larger field of view for the imager or by capturing image data using a system that could image an entire extremity, such as a leg from toes to hip.

Overview of Example Classifier

Figure 23A:
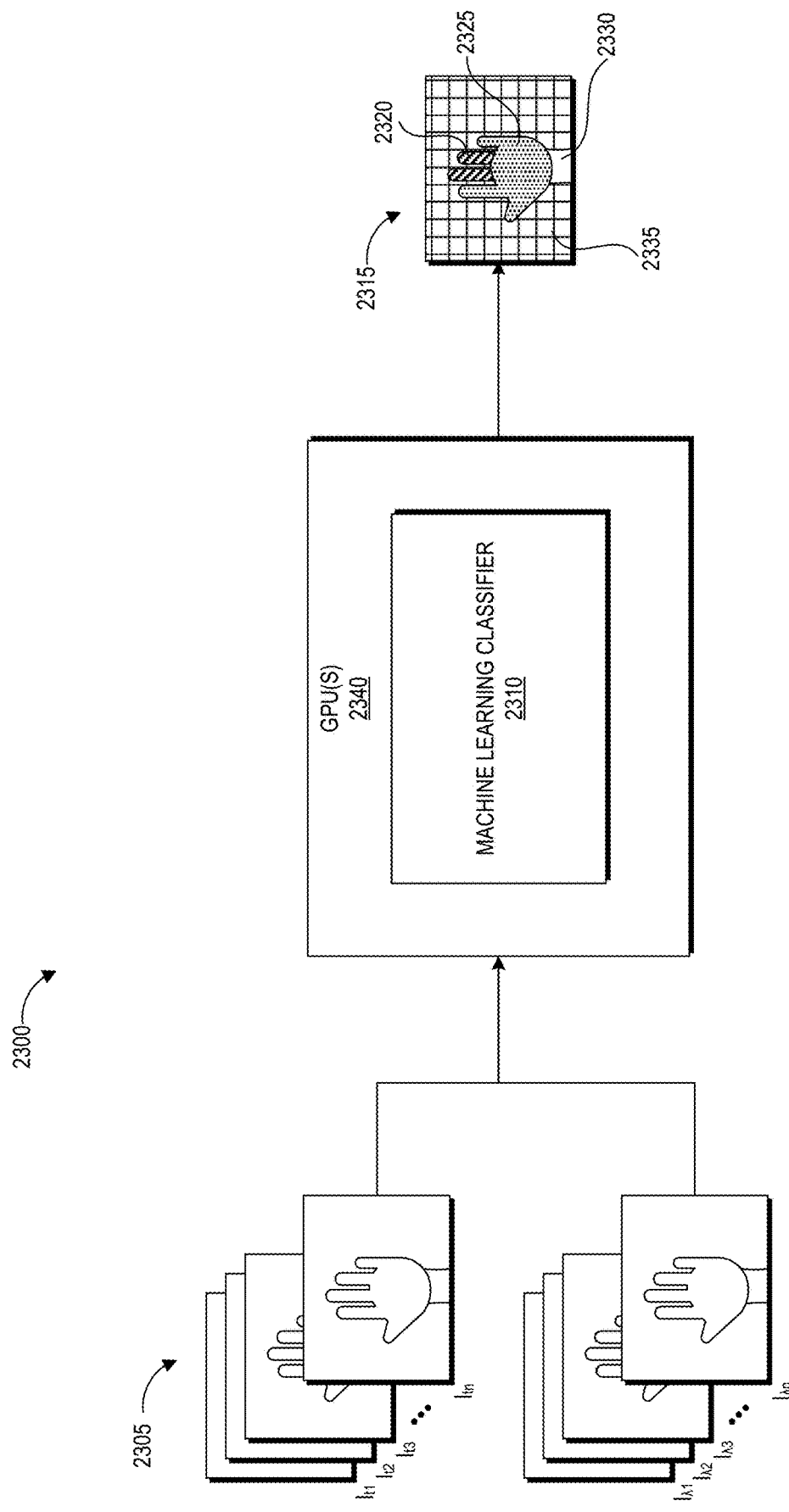
FIGS. 23A and 23B illustrate an example classification data flow and classifier structure for generating a tissue map as described herein.

FIG. 23A illustrates an example classification data flow 2300 for generating a classified tissue map 2315 as described herein. An input 2305 including a number of time-resolved images $I_{t1}$-$I_{tm}$ and a number of multispectral images $I_{\lambda 1}$-$I_{\lambda n}$, can be provided into a machine learning classifier 2310. As described above, a sequence of time-resolved images $I_{t1}$-$I_{tm}$ can include photoplethysmographic information representing pulsatile blood flow in patient tissue. In some embodiments, the sequence of time-resolved images $I_{t1}$-$I_{tm}$ can include hundreds of images, for example 400 time-resolved images captured using an 855 nm band-pass filter (or another filter passing suitable wavelength(s)) taken sequentially at a frame rate of 30 fps as described above with respect to the training. As described above, the sequence of time-resolved images $I_{t1}$-$I_{tm}$ can be omitted from some embodiments, which may beneficially reduce the amount of time required to capture the images in the input data 2305.

The multispectral images $I_{\lambda 1}$-$I_{\lambda n}$ include images captured at each of a number of different wavelengths of light. In some embodiments, the multispectral images $I_{\lambda 1}$-$I_{\lambda n}$ can include eight images captured at different wavelengths of light. As one example, the wavelengths can include (listed as center wavelength±full-width at half-max): 420 nm±20 nm, 525 nm±35 nm, 581 nm±20 nm, 620 nm±20 nm, 660 nm±20 nm, 726 nm±41 nm, 820 nm±20 nm, and/or 855 nm±30 nm. These images can be captured using the respective wavelength bandpass filters and taken at a frame rate of approximately 4-6 fps. The time-resolved images $I_{t1}$-$I_{tm}$ and multispectral images $I_{\lambda 1}$-$I_{\lambda n}$ can each be of the same x by y pixel dimensions, and in some embodiments can have approximately the same object positioning across the image set. Other embodiments can be captured from varied viewpoints, and the images can be registered prior to input into the machine learning classifier 2310. Further embodiments can be captured from varied viewpoints and separately provided to the classifier 2310, with mappings of output pixel classification scores registered after calculation.

In one implementation, the set of images of the input 2305 can be two-dimensional images of the imaged tissue site. In some embodiments, the images can all be captured from a single viewpoint. In other embodiments, the set of images can include multiple subsets of MSI and PPG images with each subset captured from a different viewpoint around the entire circumference of the potential amputation site. Such images can be stitched together in some embodiments to form a set of panoramic images of the tissue site. Other embodiments can generate a set of panoramic images via an imaging system including multiple cameras that can cooperatively capture some or all of the circumference around the tissue site in one scan. In another implementation, image information from around the tissue site can be used to construct a 3D model of the tissue site, and the disclosed classifier can operate on a set of 3D models including both time-resolved data and multispectral data.

Figure 23B:
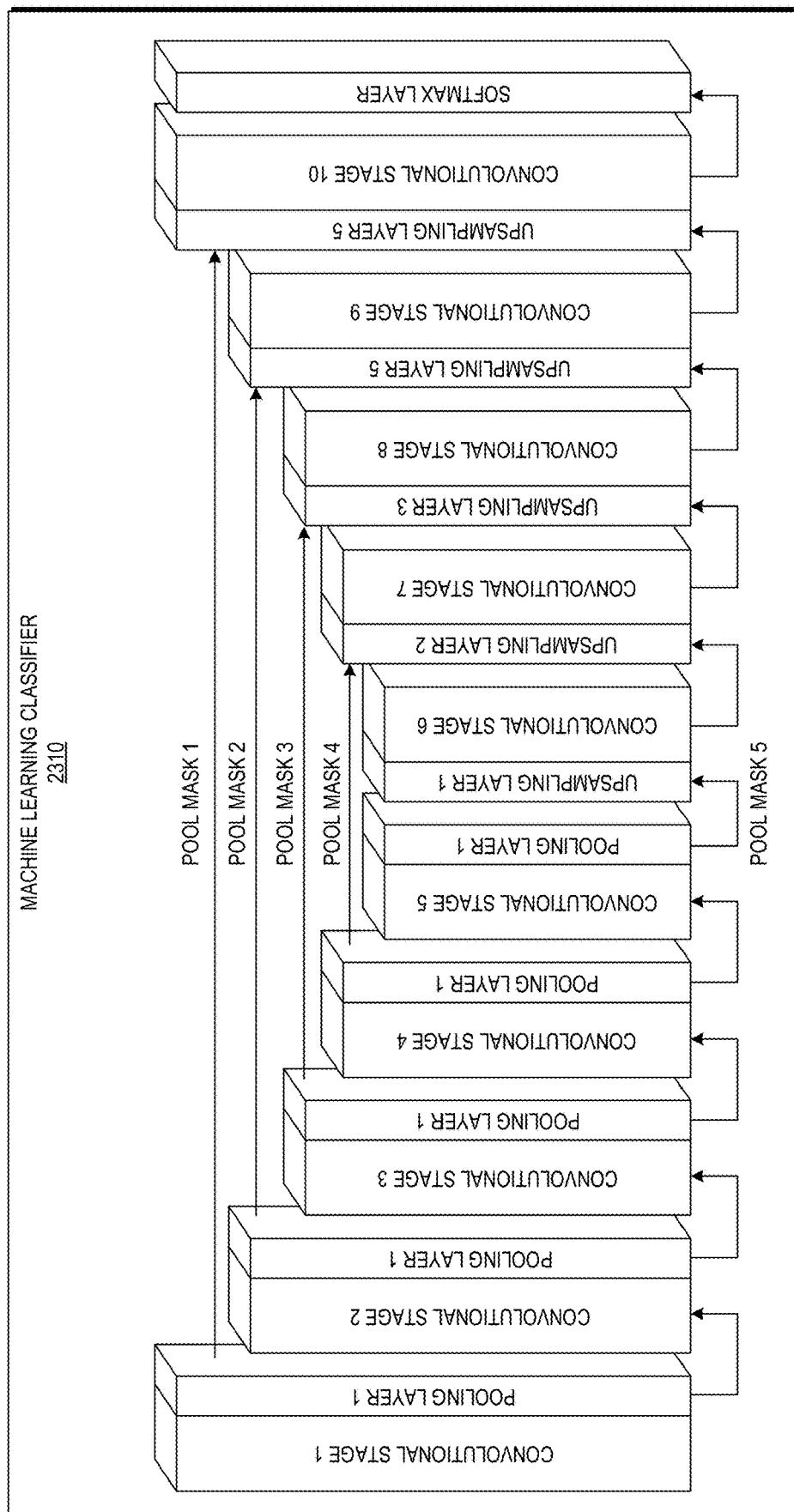

In some embodiments the machine learning classifier 2310 can be an artificial neural network, for example a convolutional neural network (CNN), as discussed in more detail with respect to FIG. 23B. In other embodiments, the machine learning classifier 2310 can be another type of neural network or other machine learning classifier suitable for predicting pixel-wise classifications from supervised learning. Artificial neural networks are artificial in the sense that they are computational entities, analogous to biological neural networks in animals, but implemented by computing devices. A neural network typically includes an input layer, one or more intermediate layers, and an output layer, with each layer including a number of nodes. The nodes in each layer connect to some or all nodes in the subsequent layer and the weights of these interconnections are typically learnt from data during the training process. Each individual node may have a summation function which combines the values of all its inputs together. Specifically, nodes of adjacent layers may be logically connected to each other, and each logical connection between the various nodes of adjacent layers may be associated with a respective weight. A node may be thought of as a computational unit that computes an output value as a function of a plurality of different input values. Nodes may be considered to be "connected" when the input values to the function associated with a current node include the output of functions associated with nodes in a previous layer, multiplied by weights associated with the individual "connections" between the current node and the nodes in the previous layer.

A CNN is a type of feed-forward artificial neural network. The layers of a CNN have nodes arranged in 3 dimensions: width, height and depth. The nodes inside a layer are only connected to a small region of the width and height layer before it, called a receptive field. In some embodiments, the convolutional filters can be two-dimensional and thus convolutions can be repeated for each image (or convolved transformation of an image) in the input volume or a designated subset of the images. In other embodiments, the convolutional filters can be three-dimensional and thus extend through the full depth of nodes of the input volume. Distinct types of layers, both locally and completely connected, are stacked to form a CNN architecture. The nodes in each convolutional layer of a CNN can share weights such that the convolutional filter of a given layer is replicated across the entire width and height of the input volume, reducing the overall number of trainable weights and increasing applicability of the CNN to data sets outside of the training data.

The parameters of a CNN can be set in a process referred to as training. For example, a CNN can be trained using training data that includes input data and the correct or preferred output of the model for the corresponding input data. Sets of individual input vectors ("mini-batches") may be processed at the same time by using an input matrix instead of a single input vector. The CNN can repeatedly process the input data, and the convolutional filters (e.g., the weight matrices) can be modified in what amounts to a trial-and-error process until the CNN produces (or "converges" on) the correct or preferred output. The modification of weight values may be performed through a process referred to as "back propagation." Back propagation includes determining the difference between the expected model output and the obtained model output, and then determining how to modify the values of some or all parameters of the model to reduce the difference between the expected model output and the obtained model output.

The machine learning classifier 2310 can be implemented as computer-executable instructions representing the computational structure of the machine learning classifier 2310 by one or more processors, for example one or more graphics processing units (GPUs) 2340. In some implementations, the input 2305 can be processed in mini-batches including a subset of images from the total input image set 2305 based on the size of each image and on the capacity of the GPU(s) 2340, for example eight images per mini-batch. In such implementations, training can involve batch back-propagation to back-propagate the averaged error across the images in the mini-batch through the CNN.

The machine learning classifier 2310 generates per-pixel classification wherein the output includes a classification value for each [x,y] pixel location. During training of the machine learning classifier 2310, these output classification values can be compared to a pre-generated tissue map 2315 and identified error rates can be fed back into the machine learning classifier 2310. As described above, a pre-generated tissue map 2315 can include a ground truth mask generated by a physician after analysis and/or treatment of the imaged tissue site. The weights of the various node connections, for example convolutional filters in a number of convolutional layers, can be learnt by the machine learning classifier 2310 through this back propagation.

During implementation of the machine learning classifier 2310, the output classification values can be used to generate tissue map 2315 to indicate pixels corresponding to tissue of various designated categories of tissue health. As described above, the tissue map 2315 can include a number of visually distinct colors or patterns to indicate different pixel classifications, for example background 2335, healthy 2330, diseased 2325, and necrotic 2320.

FIG. 23B illustrates an example classifier architecture for a CNN implementation of the machine learning classifier 2310. The input 2305 can be provided to the CNN as a three-dimensional volume of [x, y, z] storing the raw pixel values of each spectral and/or photoplethysmographic image in the input image set. Each pixel value of the input data set can be considered as a node in the input layer of the CNN. As described above, each pixel can have an intensity value representing the brightness of the pixel. In some embodiments, this number is stored as an 8-bit integer giving a range of possible values from 0 to 255, where a value of zero represents a "dark" pixel from a photodiode having no detected light and value of 255 represents a "light" pixel from a photodiode fully saturated with light. The width (x) of the input volume can be equal to the number of pixels along the x axis of the images, and the height (y) of the input volume can be equal to the number of pixels along the y axis of the images. The input volume depth (z) can be equal to the number of multispectral images and time-resolved images in the data set.

As illustrated, the CNN can include a symmetrical convolutional encoder-decoder architecture including a number of convolutional stages followed by a softmax layer. Each convolutional stage can include one or more convolutional layers followed by a rectified linear unit layer ("ReLu layer"). A convolutional layer will compute the output of nodes that are connected to local regions in the input (based on kernel size), with each node computing a dot product between their weights and the values of a small region in which they are connected to in the input volume. As described above, the kernels of each convolutional layer (for example, a 3×3 block of weights learnt during training) can be convolved across 3×3 blocks of the width and height of the input volume and through some or all of the values along the depth (z) of the input volume. After convolution at each convolutional layer, a ReLu layer can apply an elementwise activation function before the output volume is provided to a next layer. For example, the function of a ReLu layer can be a function that replaces any negative numbers in the output of a convolutional layer with a zero and multiplies all positive numbers in the output by a slope of one.

The convolutional stages include a number of encoder convolutional stages (convolutional stages 1-5) followed by a corresponding number of decoder convolutional stages (convolutional stages 6-10). Each encoder convolutional stage corresponds to one of the decoder convolutional stages as indicated by the arrows representing transfer of the pool masks. The encoder convolutional stages (convolutional stages 1-5) are each followed by a pooling layer (pooling layers 1-5), which in turn provides a downsampled data set to the subsequent convolutional stage as well as provides a pool mask (pool masks 1-5) to the upsampling layer (upsampling layers 1-5) of a corresponding decoder convolutional stage (convolutional stages 6-10). Each pooling layer 1-5 will perform a downsampling operation along the spatial dimensions (x, y) of the input volume and output the downsampled volume to the subsequent stage. The pool mask carries information regarding the downsampled data to the corresponding decoder convolutional stage. The function of the pooling layer is to progressively reduce the spatial size of the representation to reduce the amount of parameters and computation in the CNN, and also to control overfitting. The function of the pool mask is to help maintain spatial information that is discarded while allowing computation to be reduced.

To illustrate, the pooling layers 1-5 can implement max-pooling. Max-pooling can include, for example, identifying the values of a 2×2 matrix along the spatial dimensions of the output volume, finding the maximum of the four values in the 2×2 matrix, and outputting the maximum value as the single value for that block. No downsampling is performed along the depth of the input in some embodiments. As such, each pooling layer reduces the spatial dimensions of the output volume by 25% for subsequent convolutional layers. The pool mask output from a layer stores the other three (i.e., non-maximum) pixel values and provides these to the upsampling layer of the corresponding decoder convolutional layer. Thus, during upsampling, rather than using zeros in the matrix of values, the actual values of the corresponding encoder convolutional layer are used.

The softmax layer can receive the output of the final convolutional layer of convolutional stage 10 and produce class probabilities for each [x,y] pixel location of the input images. The softmax layer can apply the softmax function, which is a normalized exponential function that "squashes" a K-dimensional vector of arbitrary real values to a K-dimensional vector of real values in the range of (0,1) that add up to 1. The output of the softmax layer can be a matrix of classification scores for each pixel location or an N-channel image of probabilities, where N is the number of classification classes. In some embodiments, a pixel can be assigned to a class corresponding to the maximum probability at the pixel.

In one example implementation of the CNN, encoder convolutional stage 1 and corresponding decoder convolutional stage 10 each have two convolutional layers, encoder convolutional stage 2 and corresponding decoder convolutional stage 9 each have two convolutional layers, encoder convolutional stage 3 and corresponding decoder convolutional stage 8 each have three convolutional layers, encoder convolutional stage 4 and corresponding decoder convolutional stage 7 each have three convolutional layers, and encoder convolutional stage 5 and corresponding decoder convolutional stage 6 each have three convolutional layers. In some embodiments, each convolutional layer can implement a 3×3 kernel having a padding of 1 and stride of 1. The weights (values in the 3×3 matrix) in a kernel can be applied to each node in the input volume. Some or all kernel weights can vary between the convolutional layers or be the same, depending upon the determinations made during training.

In other examples of the CNN, the encoder and decoder convolutional stages can have greater or fewer numbers of convolutional layers each followed by a ReLu layer. Other implementations of the CNN can have greater or fewer convolutional stages, such that the CNN has corresponding encoder and decoder convolutional stages. Other CNN implementations may not use encoder and decoder convolutional stages but rather may have several convolutional layers without the use of pool masks. The convolutional filters can have other sizes, for example a kernel size of 4 or 5, and may be the same size across the various convolutional layers of the CNN or may be of varying sizes.

Overview of Feature Set Examples

Experimental data indicates example benefits of fusing PPG and MSI features into one classifier, as discussed below.

In the following discussion, feature sets include photoplethysmography (PPG), multispectral imaging (MSI), and "real image" (RI; i.e., textural and geometric information from the spatial domain) features. Example methodology includes drawing ground truth, training a classifier with all three feature sets both separately and also together, classifying images, and reporting error in order to compare classifiers with different feature set compositions. Currently, features have been developed and can be used for classification. These features are broken into three categories of feature sets: PPG, MSI, and RI. For the following examples a classifier, QDA (Quadratic Discriminant Analysis), was trained with a variety of feature sets. The feature sets were combined until all 33 features were included in the model. Each classifier developed (i.e., each classifier with distinct feature sets) were compared based on their classification error.

The PPG classifier features can include the following 14 features:
1. Image Output
2. Maximum over mean
3. Standard deviations away from mean
4. Number of crossings
5. SNR a small neighborhood
6. Improved SNR
7. Lighting normalized
8. Image Normalized
9. Standard deviation
10. Skewness
11. Kurtosis
12. X-gradient
13. Y-gradient
14. Standard deviation of the gradients The Real Image classifier features can include the following 11 features:
1. Real image
2. Real image normalized
3. Skewness
4. Kurtosis
5. X-gradient
6. Y-gradient
7. Standard deviation within X-gradient
8. Range within a small neighborhood
9. Range within a small neighborhood normalized
10. Range within a big neighborhood
11. Range within a big neighborhood normalized.

The MSI classifier features can include the following 8 features:
1. MSI $\lambda_1$
2. MSI $\lambda2$
3. MSI $\lambda_3$
4. MSI $\lambda_4$
5. MSI $\lambda_5$
6. MSI $\lambda_6$
7. MSI $\lambda_7$
8. MSI $\lambda_8$ Error reduction can increase as more features are added. Groups of features can be ranked in order of importance, and in one example can be ranked as: (1) MSI, (2) RI, (3) PPG. Some embodiments of the classifier can be transferable, meaning that the classifier can be trained on a first subject and then used to classify injuries on a second subject.

Overview of Outliers Detection and Removal

The disclosed techniques can incorporate outlier detection and removal for the data used to train the machine learning tissue classification models. Outlier detection and removal is an important area in statistic and pattern recognition area, which has been used widely in different areas, such as, credit card fraud, interesting sensor events, medical diagnosis, network security etc. Outlier detection may have other names, like anomaly detection, novelty detection, etc. Most outlier detection is model-based and proximity-based direction. For model-based classifiers, the disclosed techniques can use statistical tests to estimate the parameters of the sample distribution, for example it may be considered as Gaussian distribution based on the central limit theorem (CLT). For Gaussian distributions, two parameters can be considered: the mean; and standard deviation. The disclosed techniques can obtain these parameters from the maximum likelihood or maximum a posteriori estimation. In the model-based approach, outliers will be the points that have low probability of occurrence, which can be estimated by calculating the Z-score (standard score). As a rule-of-thumb, if the probability of an observation is greater than 0.95, or less than 0.05, these observations may be considered as outliers. This is based on univariate analysis. If it is a multivariate normal distribution:

$$N(x) = \frac{1}{(2\pi)^d |\Sigma|} e^{-\frac{(x-\mu)^T \Sigma^{-1}(x-\mu)}{2}}$$

$\mu$ is the mean value of all points, $\Sigma$ is the covariance matrix from the mean. The disclosed techniques can calculate the Mahalanobis distance of point x to $\mu$. The Mahalanobis distance follows a $\chi^2$ distribution with d degrees of freedom. (d is the dimension of the data). Finally, for a point x, if the Mahalanobis distance is greater than $\chi^2$ (0.975), then the point can be considered an outlier. The methodology of this statistical approach works in most cases, however, the parameters (e.g., mean and variance) can be sensitive to the outliers when estimating the parameter. Additionally, with Mahalanobis distance, the minimum distance of an observation to the mean is a function of the dimension which becomes higher with increasing dimensionality. Depth-based approaches search for outliers at the border of the data space and deviation-based approaches minimize the variance when removing the outliers.

In proximity-based outlier detection, the nearest neighbor idea can be used to generate an approximation of inclusion or exclusion. At first, the concept of distance is important. If there are N samples and M variables, the size of matrix is N*M, and for example by using Euclidean distance, the disclosed techniques can calculate the distance among sample space by defined distance by: $d(q, p) = \sqrt{(q_1-p_1)^2+(q_2-p_2)^2+...+(q_m-p_m)^2}$. Clustering methods are a common methods that employs this concept of distance. In clustering, the disclosed techniques can define a radius $\omega$, for any group of points from which a center has be identified (centroid). If the points is less than or equal to this radius, it could be considered a good point, from which the centroid is updated based on the inclusion of this new data point. For the k-nearest neighbors approach, the sum of the distance to the k-nearest neighbors of the points. However, this method is also not robust in datasets of high dimensionality.

There are other methods still based on other definitions of central tendency. For instance, the local outlier factor (LOF) is based on density. Density can be estimated from clusters of points. If a certain cluster or grouping of points has a lower density than its neighbors, the points within this cluster may be potential outliers. Again, if the datasets are high order dimensional data, these techniques may not work. Angle based outlier degree (ABOD) and grid-based subspace outliers detection have been proposed to handle high dimensional datasets.

Ultimately, outlier detection and removal can significantly improve the accuracy of the MSI application for skin tissue classification. The removal of outliers can successfully reduce the variance in the sample space for each of the tissue classes. By restricting the variance in this fashion, the overlap in spectral characteristics can be reduced in a corresponding manner With reduced overlap, the training of classification models can be improved with a discernable increase in classification accuracy. This model has the potential to aid decision-making for physicians treating amputation patients using quantitative data.

Overview of Other Example Alternatives

Another clinical application of the devices described herein is to classify decubitus ulcers, also known as pressure ulcers or bed sores. These wounds develop because of pressure applied to tissue resulting in the obstruction of blood flow to that tissue. As a result of the obstruction, tissue necrosis and tissue loss occurs. In many cases, in later stages, this leads to visible alterations in the color of the tissue. Decubitus ulcers may be categorized in stages one through four, which relate to the amount of tissue loss that has occurred.

Part of the difficulty of identifying decubitus ulcers is that early obstruction can cause changes in the tissue that are not readily observable on the tissue's surface. Devices described herein are effective in identifying decubitus ulcers at early stages of development, which facilitates early and preventative treatment. A device manufactured as described herein made the classifications by reading light reflectance in both different times and in different frequency bands, which allowed the detection of a difference in the composition of the tissue and a difference in blood flow to the tissue.

In contrast to decubitus ulcers where blood to tissue is obstructed, tissue may also suffer from too much blood. In hyperaemia, which can manifest as erythema, there is an increase in blood flow to tissue. This can lead to swelling, discoloration, and necrosis. It may also be accompanied by engorged capillaries and veins, excessive hemosiderin in the tissue, and fibrosis. Alternatives of the present invention may be effective in identifying and assessing tissue suffering from hyperaemia at its early stages. Again, the combination of being able to detect the changes in the nature and quality of the tissue, along with the blood flow to the tissue, allows these alternatives to readily identify and assess the severity of tissue suffering from hyperaemia.

Alternative devices described herein have numerous other applications in the medical field where tissue needs to be classified and assessed. Like necrotic tissue, low-perfusion tissue, and hyperaemia, there are other types of wounds that these alternatives can classify and assess, including: abrasions; lacerations; hemorrhaging; rupture injuries; punctures; penetrating wounds; chronic wounds; or, any type of wound where the nature and quality of the tissue changes along with a change in blood flow to the tissue. The alternatives presented herein provide physiological information relating to tissue viability in a simple image format to medical practitioners. Information such as blood perfusion and oxygenation at the wound site are important indicators of wound healing. By imaging these hemodynamic characteristics hidden beneath the skin, physicians can be better informed about the progress of wound healing and make better educated and timely patient-care decisions. At the same time, some devices described herein can give information about the composition of the skin, which is indicative of the skin's condition.

Moreover, the use of some of the devices described herein are not limited to applications where there has been damaged tissue. Indeed, some alternatives may also detect healthy tissue and differentiate the healthy tissue form necrotic tissue or tissue that is soon to be necrotic.

One natural place healthy tissue may be classified and assessed is in comparison to a wound or skin condition. For example, along with low perfusion tissue, there may be regions of healthy tissue associated with or juxtaposed to the low perfusion tissue. It can be helpful to both level of amputation identification and amputation site treatment to be able to identify where the margin of healthy tissue exists with respect to necrotic tissue or tissue that has a predestination to become necrotic tissue. The healthy tissue may be identified by imaging the skin in both different times and different frequency bands to assess the composition of the skin, as well as, blood perfusion and oxygenation at the tissue site.

Alternatives described herein may also classify tissue based on its likely success as an amputation site flap, as graft tissue, or as a regenerative cell implant. This classification can take into account the quality and nature of the recipient tissue, as well as, the recipient tissue's ability to accept a new blood supply. Alternatives may also classify the receiving tissue based on how likely the tissue will be able to form a new blood supply for the flap or graft or regenerative cell implant, and how healthy the skin is generally. In both classifying the flap tissue, graft tissue, or the receiving tissue, some devices described herein can analyze a plurality of images corresponding to different times and different frequency bands.

In addition to merely classifying the health of tissue, alternatives as described herein may also measure various aspects of the tissue, such as, the thickness of a region of skin and skin granulation tissue may also be assessed. In another example, the health of tissue around a suture, and the healing of a suture can be monitored and assessed with the devices described herein.

Another application of some of the devices described herein is to monitor tissue healing. The devices described herein can also obtain several images at numerous points in time to monitor how a wound changes, or how healthy tissue forms. In some cases, a therapeutic agent, such as a steroid, hepatocyte growth factor (HGF), fibroblast growth factor (FGF), an antibiotic, an isolated or concentrated cell population that comprises stem cells and/or endothelia cells, or a tissue graft may be used to treat a wound or other ailment and such treatments can be monitored using a device as described herein. Some alternatives can monitor the effectiveness of therapeutic agents by evaluating the healing of tissue before, during, or after application of a particular treatment. Some alternatives do so by taking a plurality of images at both different times and different frequency bands. According to these images, the light reflected from the skin can be used to assess the nature and quality of the tissue, as well as the blood flow to the tissue. As a result, the devices as described herein can give valuable information about how a tissue is healing, and the effectiveness and speed at which a therapeutic agent facilitates the healing process.

Some alternatives may be used to monitor the introduction of a left ventricular assist device (LVAD) and the healing process after such an implant. As LVAD flow increases, the diastolic pressure rises, the systolic pressure remains constant, and the pulse pressure decreases. The pulse pressure, which is the difference in systolic and diastolic pressures, is influenced by the contractility of the left ventricle, intravascular volume, pre-load and after-load pressure, and pump speed. Therefore, assessment of the arterial blood pressure values and waveforms gives valuable information about the physiologic interaction between the LVAD and the cardiovascular system. For instance, poor left ventricle function is related to arterial waveforms that do not show pulsatility. Alternatives described herein can be used to monitor the return of pulsatile flow in patients after LVAD implantation and provide a powerful tool in monitoring and aiding patients' recovery.

Certain alternatives may also be used in providing intraoperative management of plastic surgery tissue transfer and reconstructive procedures. For example, in the case of breast cancer patients, treatment may involve a total mastectomy followed by breast reconstruction. Complications for breast reconstruction have been reported to be as high as 50%. The devices described herein can facilitate evaluation of both tissue that is ready to receive the graft, and the graft tissue itself. The evaluation in these alternatives looks at the health and quality of the tissue and the blood perfusion and oxygenation using the methodologies discussed above.

Certain alternatives may also be used to facilitate the analysis of the treatment of chronic wounds. Chronic wound patients often receive expensive advanced treatment modalities with no measure of their efficacy. Alternatives described herein can image the chronic wound and give quantitative data to its status, including the size of the wound, the depth of the wound, the presence of wounded tissue, and the presence of healthy tissue using the aforementioned imaging techniques.

Certain alternatives described herein may also be used in identifying limb deterioration. In these applications, the images identify the peripheral perfusion in limbs. This can be used to monitor the health of normal limbs, as well as, to detect peripheral blood flow insufficiency in limbs (e.g., regions of limb ischemia or peripheral vascular disease) that may require specialized treatments, such as the introduction of growth factors (FGF, HGF, or VEGF) and/or regenerative cells including, but not limited to, stem cells, endothelial precursor cells, endothelial progenitor cells, or concentrated or isolated populations of cells comprising these cell types. In some cases, this allows for early treatment that could save a limb from amputation. In other, more severe cases, it may give medical professionals the data needed to make informed decisions of whether a limb needs to be amputated.

Another application of the devices described herein concerns the treatment of Raynaud's Phenomenon, which occurs when a patient experiences brief episodes of vasospasm (i.e., the narrowing of blood vessels). The vasospasm typically occurs in the digital arteries that supply blood to the fingers, but has also been seen to occur in the feet, nose, ears, and lips. Some alternative devices can accurately and precisely identify when a patient is suffering from Raynaud's Phenomenon, which can aid in its diagnosis at any stage.

Some alternative devices may also be used to identify, classify, or evaluate the presence of cancer cells, cancer cell proliferation, metastasis, tumor burden, or cancer stage, and after treatment, a reduction in the presence of cancer cells, cancer cell proliferation, metastasis, tumor burden, or a cancer stage. These alternatives measure the light reflected off tissue to determine the composition of the skin, which can reflect an abnormal composition associated with cancer cells. Alternatives also can measure the blood flow to the cancer cells by evaluating images at different times. The blood flow can indicate abnormal blood flow to tissue associated with the presence of cancer cells, cancer cell proliferation, metastasis, tumor burden, or a cancer stage. After the removal of cancer cells, alternatives of the present invention may also be used to monitor the recovery, including the growth of healthy tissue and any return of cancer cells.

Aspects of the aforementioned alternatives have been successfully tested in a laboratory setting, as well as, in the clinic. For example, in an experiment using optical tissue phantoms that mechanically mimicked the dynamic changes in tissue owing to pulsatile blood flow, the devices described herein had greater optical penetration than laser Doppler imaging, and also correctly detected the pulsing fluid flow under the tissue phantom material. The experiment tested pulsatile flows in the range of 40 to 200 bpm (0.67 Hz to 3.33 Hz) to test a full range of human heart rates from rest to high rates during exercise or exertion.

Another aspect of some alternatives described herein is that the devices may be coupled with a dynamic library containing one or more reference points of tissue conditions. In some cases, the dynamic library may contain base point images that contain information about healthy skin tissue. The dynamic library may also contain various images of wounds or skin conditions as points of comparison to see the evolution and/or healing of the wound or skin condition. The dynamic library may also contain sample signals of relevant signals, such as samples of normal heart rates, abnormal heart rates, noise signals, signals corresponding to healthy tissue, and signals corresponding to unhealthy tissue. The dynamic library can be stored in a centralized database in some embodiments, for example a server-based database, and can receive information via one or more networks from a number of devices as described herein. The dynamic library can be used to provide training data for the disclosed machine learning classifiers, and updated classifiers can be provided to devices in the field for enhanced tissue classification and amputation location recommendations.

In some alternatives the images in the dynamic library are other images or data taken by the devices described herein. In some alternatives, the dynamic library contains images and/or data taken by apparatuses that are not aspects of the present invention. These images can be used to assess or otherwise treat a subject.

Summary

The above disclosure has demonstrated the feasibility of identifying tissue lacking in blood flow and oxygen content in a wound model and patient case study using the disclosed instruments with PPG and MSI capabilities. As shown above, using both PPG and MSI in the disclosed technology allows for a more accurate investigation of the epidermal microvasculature and pathologies caused by reduced blood perfusion. The disclosed technology can be able to predict healing potential at a given LOA; the addition of important patient health metrics that affect wound healing outcomes can further increase the accuracy of the automated amputation site analysis system.

Additional Alternatives

Several preferred alternatives of the invention described herein are provided below.

1. A tissue classification system comprising:
   at least one light emitter configured to emit light at each of a plurality of wavelengths to illuminate a tissue region, each of the at least one light emitter being configured to emit spatially-even light;
   at least one light detection element configured to collect the light after being emitted from the at least one light emitter and reflected from the tissue region;
   one or more processors in communication with the at least one light emitter and the at least one light detection element and configured to:
   identify at least one patient health metric value corresponding to a patient having the tissue region,
   use the at least one patient health metric value select a classifier from among a plurality of classifiers, each of the plurality of classifiers trained from a different subset of a set of training data, wherein the classifier is selected based on having been trained with a subset of the set of the training data including data from other patients having the at least one patient health metric value;
   control the at least one light emitter to sequentially emit each of the plurality of wavelengths of light;
   receive a plurality of signals from the at least one light detection element, a first subset of the plurality of signals representing light emitted at the plurality of wavelengths and reflected from the tissue region;
   generate, based on at least some of the plurality of signals, an image having a plurality of pixels depicting the tissue region;
   for each pixel of the plurality of pixels depicting the tissue region:
   determine, based on the first subset of the plurality of signals, a reflectance intensity value at the pixel at each of the plurality of wavelengths, and
   determine a classification of the pixel by inputting the reflectance intensity value into the classifier, the classification associating the pixel with one of a plurality of tissue categories; and
   generate, based on the classification of each pixel, a mapping of the plurality of tissue categories over the plurality of pixels depicting the tissue region.

2. The system of alternative 1, wherein a second subset of the plurality of signals represent light of a same wavelength reflected from the tissue region at a plurality of different times, and wherein the one or more processors are configured to, for each pixel of the plurality of pixels depicting the tissue region:
   determine, based on the second subset of the plurality of signals, a PPG amplitude value at the pixel; and
   determine the classification of the pixel based additionally on inputting the PPG amplitude value into the classifier.

3. The system of any one of alternatives 1 and 2, wherein the one or more processors are configured to output a visual representation of the mapping for display to a user.

4. The system of alternative 3, wherein the visual representation comprises the image having each pixel displayed with a particular visual representation selected based on the classification of the pixel, wherein pixels associated with each of the plurality of tissue categories are displayed in different visual representations.

5. The system of any one of alternatives 1-4, wherein the plurality of tissue categories comprise a viable tissue category, a necrotic tissue category, and a tissue having small vessel disease category.

6. The system of alternative 5, wherein generating the mapping comprises identifying regions of the plurality of pixels depicting tissue associated with at least one tissue category of the viable tissue category, the necrotic tissue category, and the tissue having small vessel disease category.

7. The system of alternative 6, wherein the one or more processors are configured to output the image for display, wherein the plurality of pixels depicting the tissue regions are displayed in different colors according to the associated tissue category.

8. The system of alternative 7, wherein the one or more processors are configured to determine, based on the identified regions, a recommended location of an amputation.

9. The system of any one of alternatives 1-8, wherein the one or more processors are configured to determine, based on the plurality of signals, a melanin index of the tissue region.

10. The system of alternative 9, wherein the one or more processors are configured to select the classifier based on at least the melanin index.

11. A tissue classification method comprising:
    selecting, based on at least one patient health metric value, a classifier from among a plurality of classifiers, each of the plurality of classifiers trained from a different subset of a set of training data, wherein the classifier is selected based on having been trained with a subset of the set of the training data including data from other patients having the at least one patient health metric value;
    receiving a plurality of signals from at least one light detection element positioned to receive light reflected from a tissue region, a first subset of the plurality of signals representing light emitted at a plurality of wavelengths reflected from the tissue region;
    generating, based on at least a portion of the plurality of signals, an image having a plurality of pixels depicting the tissue region;
    for each pixel of the plurality of pixels depicting the tissue region:
    determining, based on the first subset of the plurality of signals, a reflectance intensity value at the pixel at each of the plurality of wavelengths, and
    determining a classification of the pixel by inputting the reflectance intensity value into the selected classifier, the classification associating the pixel with one of a plurality of tissue categories; and
    generating, based on the classification of each pixel, a mapping of the plurality of tissue categories over the plurality of pixels depicting the tissue region.

12. The method of alternative 11, wherein a second subset of the plurality of signals represent light of a same wavelength reflected from the tissue region at a plurality of different times, the method further comprising, for each pixel of the plurality of pixels depicting the tissue region:
    determining, based on the second subset of the plurality of signals, a PPG amplitude value at the pixel; and
    determining the classification of the pixel based additionally on inputting the PPG amplitude value into the classifier.

13. The method of any one of alternatives 11-12, further comprising determining, based on the plurality of signals, a melanin index of the tissue region.

14. The method of alternative 13, further comprising selecting the classifier based on at least the melanin index.

15. The method of any one of alternatives 11-14, wherein generating the mapping comprises identifying regions of the plurality of pixels depicting tissue associated with at least one tissue category of the viable tissue category, the necrotic tissue category, and the tissue having small vessel disease category.

16. The method of alternative 15, further comprising outputting the image for display, wherein the plurality of pixels depicting the tissue regions are displayed in different colors according to the associated tissue category.

17. A method of identifying a recommended location of an amputation, the method comprising:
selecting a patient having a tissue region in need of amputation;
programmatically controlling, via one or more hardware processors, an imaging system to capture data representing a plurality of images of the tissue region, the data representing the plurality of images including a first subset each captured using light of a different one of a number of different wavelengths reflected from the tissue region;
generating, based on at least one of the plurality of images, an image having a plurality of pixels depicting the tissue region;
for each pixel of the plurality of pixels depicting the tissue region:
determining, based on the first subset of the data representing the plurality of images, a reflectance intensity value at the pixel at each of the plurality of wavelengths, and
determining a classification of the pixel by at least inputting the reflectance intensity value into a classifier, the classification associating the pixel with one of a plurality of tissue categories; and
identifying, based on the classification of each pixel, the recommended location of the amputation within the tissue region.

18. The method of alternative 17, wherein the plurality of images include a second subset sequentially captured at a number of times, the method further comprising, for each pixel of the plurality of pixels depicting the tissue region:
determining, based on the second subset of the data representing the plurality of images, a PPG amplitude value at the pixel; and
determining the classification of the pixel based additionally on inputting the PPG amplitude value into the classifier.

19. The method of any one of alternatives 17-18, further comprising identifying a value of at least one patient health metric of the patient.

20. The method of alternative 19, further comprising inputting the value of the at least one patient health metric into the classifier to determine the classification of each pixel.

21. The method of any one of alternatives 19-20, further comprising selecting, based on at least one patient health metric value, a classifier from among a plurality of classifiers, each of the plurality of classifiers trained from a different subset of a set of training data, wherein the classifier is selected based on having been trained with a subset of the set of the training data including data from other patients having the at least one patient health metric value.

22. The method of any one of alternatives 17-21, further comprising generating, based on the classification of each pixel, a mapping of the plurality of tissue categories over the plurality of pixels depicting the tissue region.

23. The method of alternative 22, further comprising outputting a visual representation of the mapping to a user, wherein the visual representation includes a visual identification of the recommended location for the amputation.

24. The method of any one of alternatives 17-23, wherein identifying the recommended location for the amputation is performed programmatically by the one or more hardware processors.

25. A method of training a convolutional neural network to classify tissue regions of an amputation site, the method comprising:
receiving training data representing a plurality of images of the amputation site, the data representing the plurality of images including a first subset each captured using light of a different one of a number of different wavelengths reflected from the amputation site;
providing the training data as a three-dimensional volume to an input layer of the convolutional neural network, the three-dimensional volume having a height and width corresponding to a number of pixels of a height and a width of each of the plurality of images and having a depth corresponding to a number of the plurality of images;
performing a plurality of convolutions at plurality of encoder convolutional stages and a plurality of decoder convolutional stages of the convolutional neural network, wherein a first encoder convolutional stage of the plurality of encoder convolutional stages includes the input layer as a first convolutional layer;
providing an output of a last decoder convolutional stage of the plurality of decoder convolutional stages to a softmax layer of the convolutional neural network;
based on an output of the softmax layer, generating a classification value for each pixel across the height and width of the plurality of images;
comparing the classification value to each pixel to a ground truth classification of the pixel in a ground truth image, wherein the ground truth classification is based on physician analysis of the amputation site;
based on results of the comparing, identifying any errors in the classification values of the pixels; and
adjusting at least one weight of the plurality of convolutions based at least partly on back propagating the errors through the convolutional neural network.

26. The method of alternative 25, wherein the plurality of images include a second subset sequentially captured at a number of different times at a same wavelength as one another.

27. The method of any one of alternatives 25-26, wherein generating the classification comprises classifying each pixel as one of background, healthy tissue, diseased tissue, or necrotic tissue.

28. The method of any one of alternatives 25-27, wherein the first subset of the plurality of images includes eight images each captured using light of a different one of eight different wavelengths, and wherein the second subset of the plurality of images includes hundreds of images captured sequentially at the same wavelength at a rate of 30 frames per second.

29. The method of any one of alternatives 25-28, wherein each of the plurality of encoder convolutional stages and each of the plurality of decoder convolutional stages comprises at least two convolutional layers each followed by a rectified linear unit layer.

30. The method of any one of alternatives 25-29, wherein performing the plurality of convolutions comprises:
at each encoder convolutional stage of the plurality of encoder convolutional stages:
performing at least a first encoder convolution,
providing an output of the first encoder convolution to a rectified linear unit layer, and
downsampling an output of the rectified linear unit layer using a max pooling layer; and at each decoder convolutional stage of the plurality of decoder convolutional stages:
 receiving a pool mask from the max pooling layer of a corresponding one of the plurality of encoder convolutional stages, and
 performing at least a first decoder convolution based at least partly on the pool mask.

31. A method of using a convolutional neural network to classify tissue regions of a potential amputation site, the method comprising:
 receiving data representing a plurality of images of the potential amputation site, the data representing the plurality of images including a first subset each captured using light of a different one of a number of different wavelengths reflected from the potential amputation site;
 providing the data as a three-dimensional volume to an input layer of the convolutional neural network, the three-dimensional volume having a height and width corresponding to a number of pixels of a height and a width of each of the plurality of images and having a depth corresponding to a number of the plurality of images;
 performing at least one convolution on the three-dimensional volume;
 providing an output of the at least one convolution to a softmax layer of the convolutional neural network;
 based on an output of the softmax layer, generating a classification value for each pixel across the height and width of the plurality of images; and
 based on the classification value for each pixel, generating a mapping of a plurality of tissue classifications of tissue at the potential amputation site.

32. The method of alternative 31, wherein the plurality of images further include a second subset sequentially captured at a number of different times at a same wavelength as one another.

33. The method of any one of alternatives 31-32, wherein generating the classification comprises classifying each pixel as one of background, healthy tissue, diseased tissue, or necrotic tissue.

34. The method of any one of alternatives 31-33, wherein the first subset of the plurality of images includes eight images each captured using light of a different one of eight different wavelengths, and wherein the second subset of the plurality of images includes hundreds of images captured sequentially at the same wavelength at a rate of 30 frames per second.

35. The method of any one of alternatives 31-34, wherein performing the at least one convolution comprises performing a plurality of convolutions at plurality of encoder convolutional stages and a plurality of decoder convolutional stages of the convolutional neural network, wherein a first encoder convolutional stage of the plurality of encoder convolutional stages includes the input layer as a first convolutional layer.

36. The method of alternative 35, wherein performing the plurality of convolutions comprises:
 at each encoder convolutional stage of the plurality of encoder convolutional stages:
  performing at least a first encoder convolution,
  providing an output of the first encoder convolution to a rectified linear unit layer, and
  downsampling an output of the rectified linear unit layer using a max pooling layer; and
 at each decoder convolutional stage of the plurality of decoder convolutional stages:
  receiving a pool mask from the max pooling layer of a corresponding one of the plurality of encoder convolutional stages, and
  performing at least a first decoder convolution based at least partly on the pool mask.

37. The method of any one of alternatives 35-36, wherein each of the plurality of encoder convolutional stages and each of the plurality of decoder convolutional stages comprises at least two convolutional layers each followed by a rectified linear unit layer.

38. The method of any one of alternatives 31-37, wherein the convolutional neural network is trained using the method of alternative 25.

Implementing Systems and Terminology

Implementations disclosed herein provide systems, methods and apparatus for identifying, evaluating, and/or classifying a subject's tissue. One skilled in the art will recognize that these alternatives may be implemented in hardware, software, firmware, or any combination thereof.

In all of the above described experiments, the features, materials, characteristics, or groups described in conjunction with a particular aspect, alternative, or example are to be understood to be applicable to any other aspect, alternative or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing alternatives. The protection extends to any novel one, or any novel combination, of the features disclosed in this specification (including any accompanying claims, abstract and drawings), or to any novel one, or any novel combination, of the steps of any method or process so disclosed.

While certain alternatives have been described, these alternatives have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some alternatives, the actual steps taken in the processes illustrated and/or disclosed may differ from those shown in the figures. Depending on the alternative, certain of the steps described above may be removed, others may be added. Furthermore, the features and attributes of the specific alternatives disclosed above may be combined in different ways to form additional alternatives, all of which fall within the scope of the present disclosure.

It should be understood that any reference to an element herein using a designation such as "first," "second," and so forth does not generally limit the quantity or order of those elements. Rather, these designations may be used herein as a convenient way of distinguishing between two or more elements or instances of an element. Thus, a reference to first and second elements does not mean that only two elements may be employed there or that the first element must precede the second element in some manner. Also, unless stated otherwise a set of elements may include one or more elements.

A person having ordinary skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

A person having ordinary skill in the art would further appreciate that any of the various examples, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various example logic, components, modules, and circuits described in connection with the aspects disclosed herein and in connection with the figures may be implemented within or performed by an integrated circuit (IC), an access terminal, or an access point. The IC may include a general purpose processor, a digital signal processor (DSP), an application specific integrated circuit (ASIC), a field programmable gate array (FPGA) or other programmable logic device, discrete gate or transistor logic, discrete hardware components, electrical components, optical components, mechanical components, or any combination thereof designed to perform the functions described herein, and may execute codes or instructions that reside within the IC, outside of the IC, or both. The logical blocks, modules, and circuits may include antennas and/or transceivers to communicate with various components within the network or within the device. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The functionality of the modules may be implemented in some other manner as taught herein. The functionality described herein (e.g., with regard to one or more of the accompanying figures) may correspond in some aspects to similarly designated "means for" functionality in the appended claims.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

It is understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

Although the present disclosure includes certain alternatives, examples and applications, it will be understood by those skilled in the art that the present disclosure extends beyond the specifically disclosed alternatives to other alternative alternatives and/or uses and obvious modifications and equivalents thereof, including alternatives which do not provide all of the features and advantages set forth herein.

Accordingly, the scope of the present disclosure is not intended to be limited by the specific disclosures of preferred alternatives herein, and may be defined by claims as presented herein or as presented in the future. For example, in addition to any claims presented herein, the following alternatives are also intended to be encompassed within the scope of the present disclosure.

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A tissue classification system comprising:
   at least one light detection element configured to collect light reflected from a tissue region;
   one or more processors in communication with the at least one light detection element and configured to:
   identify at least one patient health metric value corresponding to a patient having the tissue region,
   use the at least one patient health metric value to select a classifier from among a plurality of classifiers, each of the plurality of classifiers trained from a different subset of a set of training data, wherein the classifier is selected based on having been trained with a subset of the set of the training data including data from other patients having the at least one patient health metric value;
   receive a plurality of signals from the at least one light detection element, a first subset of the plurality of signals representing non-laser light emitted at a plurality of wavelengths and reflected from the tissue region;
   generate, based on at least some of the plurality of signals, an image having a plurality of pixels depicting the tissue region;
   for each pixel of the plurality of pixels depicting the tissue region:
      determine, based on the first subset of the plurality of signals, a reflectance intensity value at the pixel at each of the plurality of wavelengths, and
      determine a classification score of the pixel associated with tissue healing potential by inputting the reflectance intensity value into the classifier; and
   generate, based on the classification score of each pixel, an overall score associated with tissue healing potential for the plurality of pixels depicting the tissue region.

2. The system of claim 1, wherein the one or more processors are further configured to determine, based on the classification score of each pixel, a recommended location of an amputation within the tissue region.

3. The system of claim 1, wherein the one or more processors are further configured to associate each pixel of the plurality of pixels into one of a plurality of tissue categories comprising a healthy tissue category, a necrotic tissue category, or a vascularly diseased tissue category, and to generate, based on the association of each pixel, a mapping of the plurality of tissue categories over the plurality of pixels depicting the tissue region.

4. The system of claim 3, wherein generating the mapping comprises identifying regions of the plurality of pixels depicting tissue associated with at least one tissue category of the healthy tissue category, the necrotic tissue category, or the vascularly diseased tissue category.

5. The system of claim 4, wherein the one or more processors are configured to output the image for display, wherein the plurality of pixels depicting the tissue regions are displayed in different colors according to the associated tissue category.

6. The system of claim 1, wherein the one or more processors are further configured to associate each pixel of the plurality of pixels into one of a plurality of tissue categories comprising viable tissue, necrotic tissue category, or tissue having small vessel disease, based on the classification score of each pixel.

7. The system of claim 1, wherein the one or more processors are further configured to identify at least one second patient health metric value corresponding to the patient, and wherein the classification score of each pixel is determined by inputting the reflectance intensity value and the at least one second patient health metric value into the classifier.

8. The system of claim 1, wherein the one or more processors are configured to determine, based on the plurality of signals, a melanin index of the tissue region.

9. The system of claim 8, wherein the one or more processors are configured to select the classifier based on at least the melanin index.

10. The system of claim 1, wherein the plurality of signals includes a second subset sequentially captured at a number of times, the one or more processors further configured, for each pixel of the plurality of pixels depicting the tissue region, to:
    determine, based on the second subset of the plurality of signals, a photoplethysmography (PPG) amplitude value at the pixel; and
    determine the classification score of the pixel based additionally on inputting the PPG amplitude value into the classifier.

11. A system for identifying a recommended location of an amputation, the system comprising:
    at least one light detection element configured to collect light reflected from a tissue region in need of amputation; and
    one or more processors in communication with the at least one light detection element and configured to:
    control the at least one light detection element to capture data representing a plurality of images of the tissue region, the data representing the plurality of images including a first subset each captured using light of a different one of a number of different wavelengths emitted as non-laser light and reflected from the tissue region;
    generate, based on at least one of the plurality of images, an image having a plurality of pixels depicting the tissue region;
    for each pixel of the plurality of pixels depicting the tissue region:

determine, based on the first subset of the data representing the plurality of images, a reflectance intensity value at the pixel at each of the plurality of wavelengths, and determine a classification score of the pixel associated with tissue healing potential by at least inputting the reflectance intensity value into a classifier; and identify, based on the classification score of each pixel, the recommended location of the amputation within the tissue region.

12. The system of claim 11, wherein the one or more processors are further configured to generate, based on the classification score of each pixel, a mapping of a plurality of tissue categories over the plurality of pixels depicting the tissue region.

13. The system of claim 12, wherein the plurality of tissue categories includes at least a healthy tissue category, a necrotic tissue category, or a vascularly diseased tissue category.

14. The system of claim 12, wherein the one or more processors are further configured to output a visual representation of the mapping to a user, wherein the visual representation includes a visual identification of the recommended location for the amputation.

15. The system of claim 11, wherein the one or more processors are further configured to generate, based on the classification score of each pixel, an overall score associated with tissue healing potential for the plurality of pixels depicting the tissue region.

16. The system of claim 11, wherein the one or more processors are further configured to associate each pixel of the plurality of pixels into one of a plurality of tissue categories comprising viable tissue, necrotic tissue category, or tissue having small vessel disease, based on the classification score of each pixel.

17. The system of claim 11, wherein the one or more processors are further configured to identify at least one patient health metric value corresponding to a patient having the tissue region.

18. The system of claim 17, wherein the one or more processors are further configured to use the at least one patient health metric value to select the classifier from among a plurality of classifiers.

19. The system of claim 18, wherein the one or more processors are further configured to identify at least one second patient health metric value corresponding to a patient having the tissue region, wherein the classification score of each pixel is determined by inputting the reflectance intensity value and the at least one second patient health metric value into the classifier.

20. The system of claim 11, wherein the data representing the plurality of images includes a second subset sequentially captured at a number of times, the method further comprising, for each pixel of the plurality of pixels depicting the tissue region:

determining, based on the second subset of the data representing the plurality of images, a photoplethysmography (PPG) amplitude value at the pixel; and determining the classification score of the pixel based additionally on inputting the PPG amplitude value into the classifier.

* * * * *